US012754184B2

(12) United States Patent
Kahl et al.

(10) Patent No.: US 12,754,184 B2
(45) Date of Patent: Oct. 6, 2026

(54) BINDING PROTEIN SPECIFIC FOR THE SPIKE PROTEIN OF SEVERE ACUTE RESPIRATORY SYNDROME CORONA VIRUS 2 (SARS-CoV-2)

(71) Applicant: Navigo Proteins GmbH, Halle/Saale (DE)

(72) Inventors: Mathias Kahl, Halle/Saale (DE); Erik Fiedler, Halle/Saale (DE); Eva Bosse-Doenecke, Halle/Saale (DE); Anja Katzschmann, Halle/Saale (DE); Hanna Bobolowski, Halle/Saale (DE); Jonathan Lotze, Halle/Saale (DE); Maren Meysing, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 785 days.

(21) Appl. No.: 18/012,281

(22) PCT Filed: Jun. 23, 2021

(86) PCT No.: PCT/EP2021/067257

§ 371 (c)(1),
(2) Date: Dec. 22, 2022

(87) PCT Pub. No.: WO2021/260075

PCT Pub. Date: Dec. 30, 2021

(65) Prior Publication Data

US 2023/0272050 A1 Aug. 31, 2023

(30) Foreign Application Priority Data

| | | |
|---|---|---|
| Jun. 23, 2020 | (EP) | 20181725 |
| Jul. 17, 2020 | (EP) | 20186603 |
| Jul. 31, 2020 | (EP) | 20188821 |
| Oct. 12, 2020 | (EP) | 20201357 |

(51) Int. Cl.

| | |
|---|---|
| ***G01N 33/543*** | (2006.01) |
| ***C07K 1/22*** | (2006.01) |
| ***C07K 14/005*** | (2006.01) |
| ***C07K 16/102*** | (2026.01) |
| ***C07K 16/104*** | (2026.01) |
| ***G01N 33/569*** | (2006.01) |

(52) U.S. Cl.

CPC ......... *G01N 33/54373* (2013.01); *C07K 1/22* (2013.01); *C07K 14/005* (2013.01); *C07K 16/102* (2026.01); *C07K 16/104* (2026.01); *G01N 33/56983* (2013.01); *C07K 2317/92* (2013.01); *C12N 2770/20051* (2013.01); *G01N 2333/165* (2013.01)

(58) Field of Classification Search

CPC ....... G01N 33/54373; G01N 33/56983; G01N 2333/165; C07K 1/22; C07K 14/005; C07K 16/102; C07K 16/104; C07K 2317/92; C07K 2318/20; C07K 14/31; C12N 2770/20051

See application file for complete search history.

(56) References Cited

U.S. PATENT DOCUMENTS

| | | | | |
|---|---|---|---|---|
| 2019/0300568 | A1* | 10/2019 | Knick | C07K 1/22 |
| 2024/0117010 | A1 | 4/2024 | Kahl et al. | |

FOREIGN PATENT DOCUMENTS

| | | | | |
|---|---|---|---|---|
| EP | 3 650 465 | | 5/2020 | |
| EP | 3650465 | A1 * | 5/2020 | C40B 40/00 |
| EP | 3880692 | B1 * | 1/2024 | C07K 14/31 |
| WO | WO 2015/179535 | | 11/2015 | |
| WO | WO-2015179535 | A1 * | 11/2015 | A61P 31/12 |
| WO | WO 2019/152318 | | 8/2019 | |
| WO | WO-2019152318 | A1 * | 8/2019 | C07K 14/31 |
| WO | WO 2020/099442 | | 5/2020 | |
| WO | WO-2020099442 | A1 * | 5/2020 | C07K 14/31 |
| WO | WO 2021/260052 | | 12/2021 | |

OTHER PUBLICATIONS

Yi, C., Sun, X., Ye, J. et al. Key residues of the receptor binding motif in the spike protein of SARS-CoV-2 that interact with ACE2 and neutralizing antibodies. Cell Mol Immunol 17, 621-630 (2020). (Year: 2020).*

Rudikoff S, Giusti AM, Cook WD, Scharff MD. Single amino acid substitution altering antigen-binding specificity. Proc Natl Acad Sci USA. Mar. 1982;79(6):1979-83. (Year: 1982).*

Hober S, Lindbo S, Nilvebrant J. Bispecific applications of non-immunoglobulin scaffold binders. Methods. Feb. 1, 2019;154:143-152. (Year: 2019).*

Lan, J., Ge, J., Yu, J. et al. Structure of the SARS-CoV-2 spike receptor-binding domain bound to the ACE2 receptor. Nature 581, 215-220 (2020). (Year: 2020).*

(Continued)

*Primary Examiner* — Bennett M Celsa

*Assistant Examiner* — Samadhan Jaising Jadhao

(74) *Attorney, Agent, or Firm* — Jenkins, Taylor & Hunt, P.A.

(57) ABSTRACT

The present invention relates to novel proteins that specifically bind to the spike protein or domains thereof of the severe acute respiratory syndrome corona vims 2 (SARS-Cov-2) or variants of SARS-Cov-2. The proteins of the present invention represent advanced and powerful tools, for example for the purification of the virus or a vaccine for the virus, by virtue of said binding affinity for spike protein or domains of the spike protein of SARS-Cov-2 or variants thereof. Thus, the novel proteins of the present invention are particularly advantageous because they allow precise capturing of proteins or particles comprising spike proteins, S1 domain, and/or RBD in affinity chromatography. Further, the novel proteins of the present invention can be used in medical applications caused by or related to SARS-Cov-2 or variants thereof.

19 Claims, 6 Drawing Sheets

Specification includes a Sequence Listing.

(56) References Cited

OTHER PUBLICATIONS

Esparza, T.J., Martin, N.P., Anderson, G.P. et al. High affinity nanobodies block SARS-CoV-2 spike receptor binding domain interaction with human angiotensin converting enzyme. Sci Rep 10, 22370 (2020). (Year: 2020).*

Konwarh R. Nanobodies: Prospects of Expanding the Gamut of Neutralizing Antibodies Against the Novel Coronavirus, SARS-CoV-2. Front Immunol. Jun. 23, 2020;11:1531. (Year: 2020).*

Hollingsworth, S.A., Noland, C.L., Vroom, K. et al. Discovery and multimerization of cross-reactive single-domain antibodies against SARS-like viruses to enhance potency and address emerging SARS-CoV-2 variants. Sci Rep 13, 13668 (2023) (Year: 2023).*

International Search Report corresponding to International Application No. PCT/EP2021/067225 dated Oct. 12, 2021.

International Search Report corresponding to International Application No. PCT/EP2021/067257 dated Sep. 28, 2021.

Lucchese et al. (2012) "How a single amino acid change may alter the immunological information of a peptide," Frontiers in Bioscience, vol. E4, pp. 1843-1852.

Office Action corresponding to U.S. Appl. No. 18/012,284 dated Mar. 18, 2026.

Written Opinion corresponding to International Application No. PCT/EP2021/067225 dated Oct. 12, 2021.

Written Opinion corresponding to International Application No. PCT/EP2021/067257 dated Sep. 28, 2021.

* cited by examiner

FIGURE 1. Amino acid sequences of binding proteins for SARS-Cov-2 spike protein or domains thereof

FIGURE 1A: Amino acid sequences of monomers

| SEQ ID | amino acid sequences |
|---|---|
| 1 | NAAVLDIAQHSATEEIWWLPNLTKQQKVWFIMSLTQDPSVSKEVLGEAQKLNDSQAPK |
| 2 | IAAKFDEAQQYAFYKILHLWNLTEEQRNAFIQSLRDDPSVSLEVLGEARKLNTSQAPK |
| 4 | IAAKFDEAQYAAFLEIXHLPNLTEEQRXAFIXSLXDDPSVSLEVLGEAQKLNDSQAPK |
| 5 | IAAKFDEAQYAAFLEIVHLPNLTEEQRQAFIASLWDDPSVSLEVLGEAQKLNDSQAPK |
| 6 | IAAKFDEAQYAAFLEIHHLPNLTEEQRHAFILSLYDDPSVSLEVLGEAQKLNDSQAPK |
| 23 | IAAKFDEAQYAAFLEIQHLPNLTEEQRQAFIVSLADDPSVSLEVLGEAQKLNDSQAPK |
| 20 | IAAKFDEAQLAAFXEIRHLPNLTEEQREAFITSLYDDPSVSLEVLGEAQKLNDSQAPK |
| 21 | IAAKFDEAQLAAFEEIRHLPNLTEEQREAFITSLYDDPSVSLEVLGEAQKLNDSQAPK |
| 3 | IAAKFDEAQLAAFQEIRHLPNLTEEQREAFITSLYDDPSVSLEVLGEAQKLNDSQAPK |
| 22 | IAAKFDEAQQAAFYEILHLPNPTEWQRNYFIQQLRDDPSVSLAVLGRAQVLNDSQAPK |
| 24 | IAAKFDEAQQAAFYEILHLPNLTELQRNWFIQLLRDDPSVSLQVLGHAQYLNDSQAPK |
| 25 | IAAKFDEAQQYAFYQILHLHNLTEEQRNAFIQSLRDDPSVSHEVLGEAKKLNESQAPK |
| 26 | IAAKFDEAQQWAFYEILHLENLTEEQRNAFIQSLRDDPSVSREVLGEATKLNTSQAPK |
| 28 | IAAVLDIDQHAATEEIWWLPNLTKQQKVWFIMSLTQDPSVSLEILAEAKKLNDAQAPK |
| 37 | IAAKFDEAQQLAFYLILHLINLTEEQRNAFIQSLRDDPSVSLEVLGEAYKLNLSQAPK |

FIGURE 1B: Amino acid sequences of dimers

| SEQ ID | Amino acid sequences |
|---|---|
| 7 | IAAKFDEAQQYAFYKILHLWNLTEEQRNAFIQSLRDDPSVSLEVLGEARKLNTSQAPK<br>IAAKFDEAQYAAFLEIVHLPNLTEEQRQAFIASLWDDPSVSLEVLGEAQKLNDSQAPK |
| 8 | IAAKFDEAQQYAFYKILHLWNLTEEQRNAFIQSLRDDPSVSLEVLGEARKLNTSQAPK<br>IAAKFDEAQYAAFLEIHHLPNLTEEQRHAFILSLYDDPSVSLEVLGEAQKLNDSQAPK |
| 9 | IAAKFDEAQQWAFYEILHLENLTEEQRNAFIQSLRDDPSVSREVLGEATKLNTSQAPK<br>IAAKFDEAQLAAFQEIRHLPNLTEEQREAFITSLYDDPSVSLEVLGEAQKLNDSQAPK |
| 17 | IAAKFDEAQQYAFYKILHLWNLTEEQRNAFIQSLRDDPSVSLEVLGEARKLNTSQAPK<br>IAAKFDEAQYAAFLEIQHLPNLTEEQRQAFIVSLADDPSVSLEVLGEAQKLNDSQAPK |
| 18 | IAAKFDEAQLAAFEEIRHLPNLTEEQREAFITSLYDDPSVSLEVLGEAQKLNDSQAPK<br>IAAKFDEAQQAAFYEILHLPNPTEWQRNYFIQQLRDDPSVSLAVLGRAQVLNDSQAPK |
| 19 | IAAKFDEAQQAAFYEILHLPNLTELQRNWFIQLLRDDPSVSLQVLGHAQYLNDSQAPK<br>IAAKFDEAQQYAFYQILHLHNLTEEQRNAFIQSLRDDPSVSHEVLGEAKKLNESQAPK |
| 36 | IAAKFDEAQQLAFYLILHLINLTEEQRNAFIQSLRDDPSVSLEVLGEAYKLNLSQAPK<br>IAAKFDEAQLAAFQEIRHLPNLTEEQREAFITSLYDDPSVSLEVLGEAQKLNDSQAPK |

FIGURE 2.
FIGURE 2A. Pool-ELISA after Phage Display Selection
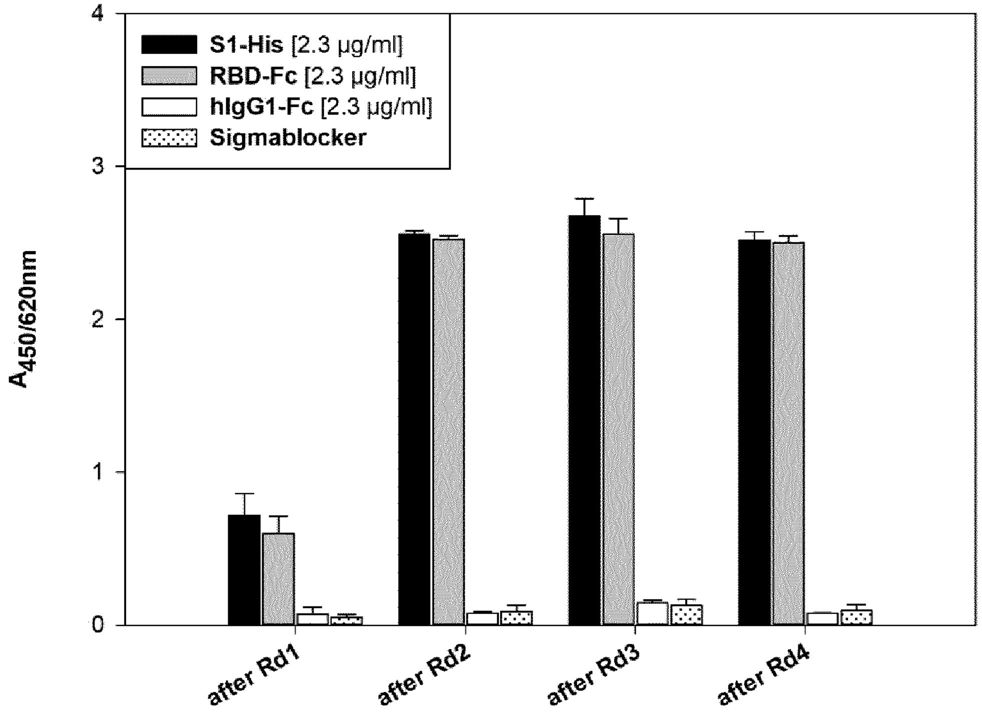
FIGURE 2B: Octet Analysis of μ-scale purified binding proteins
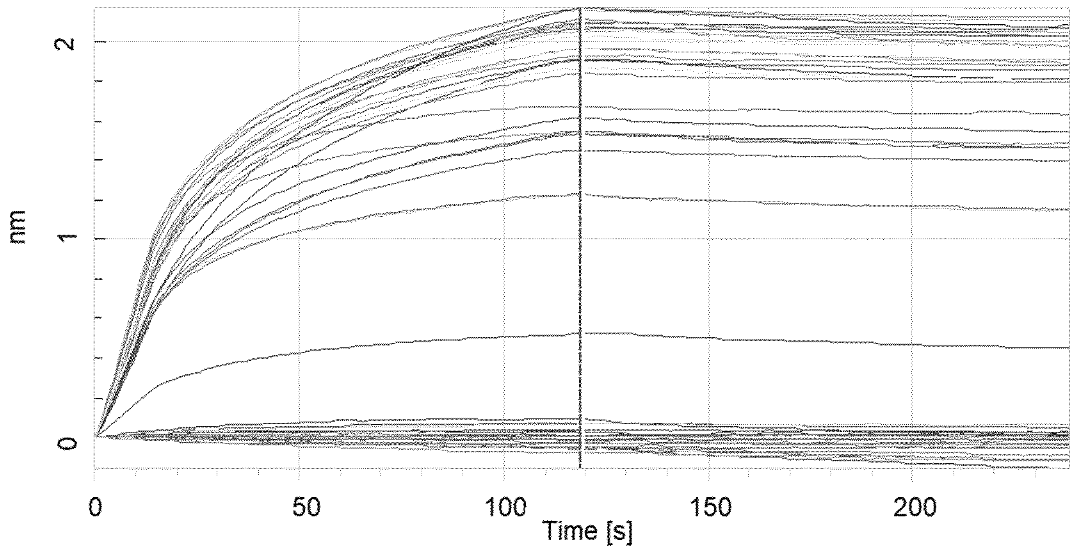

FIGURE 3. Analysis of simultaneous binding of S1-His or RBD and ACE2 to spike-binding proteins - SEQ ID NO: 1 (212434) is binding to an overlapping epitope for S1 or RBD and ACE.
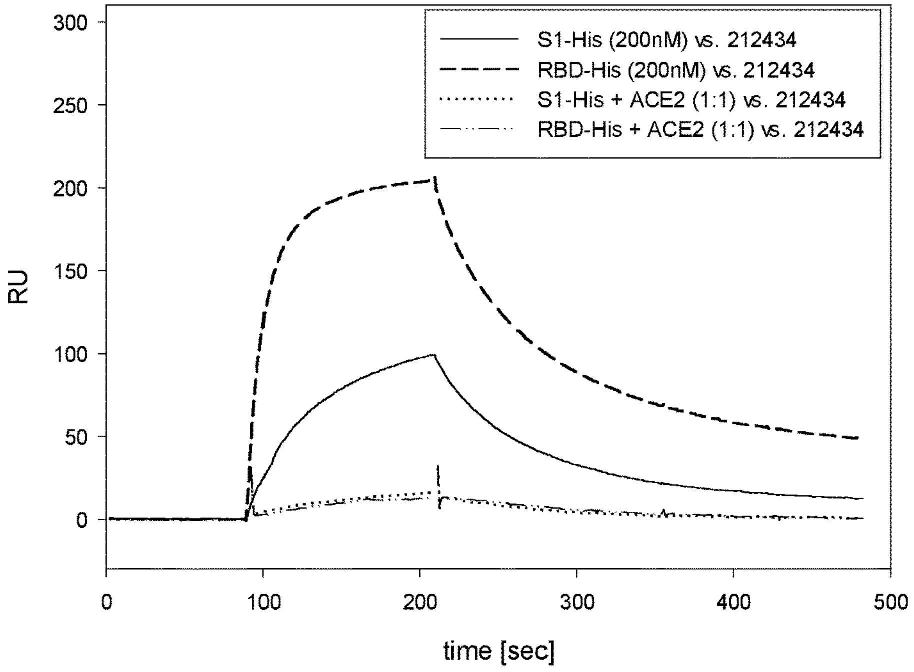
FIGURE 4. Elution pH profile of the fusion protein comprising SEQ ID NO: 1 (AIC)
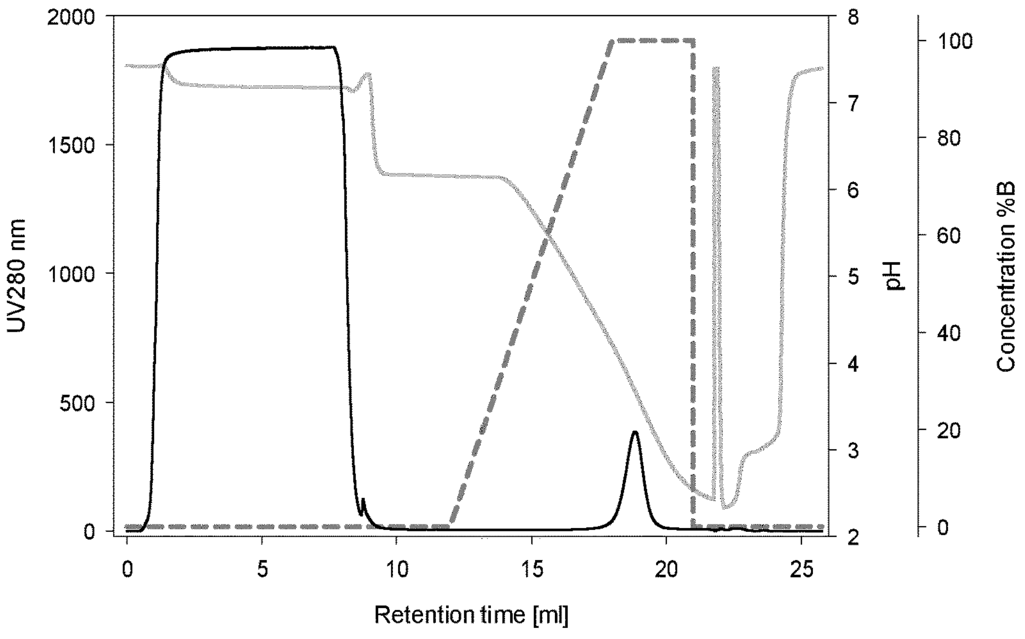

FIGURE 5: SBC Determination of fusion protein comprising SEQ ID NO: 28 (212896)
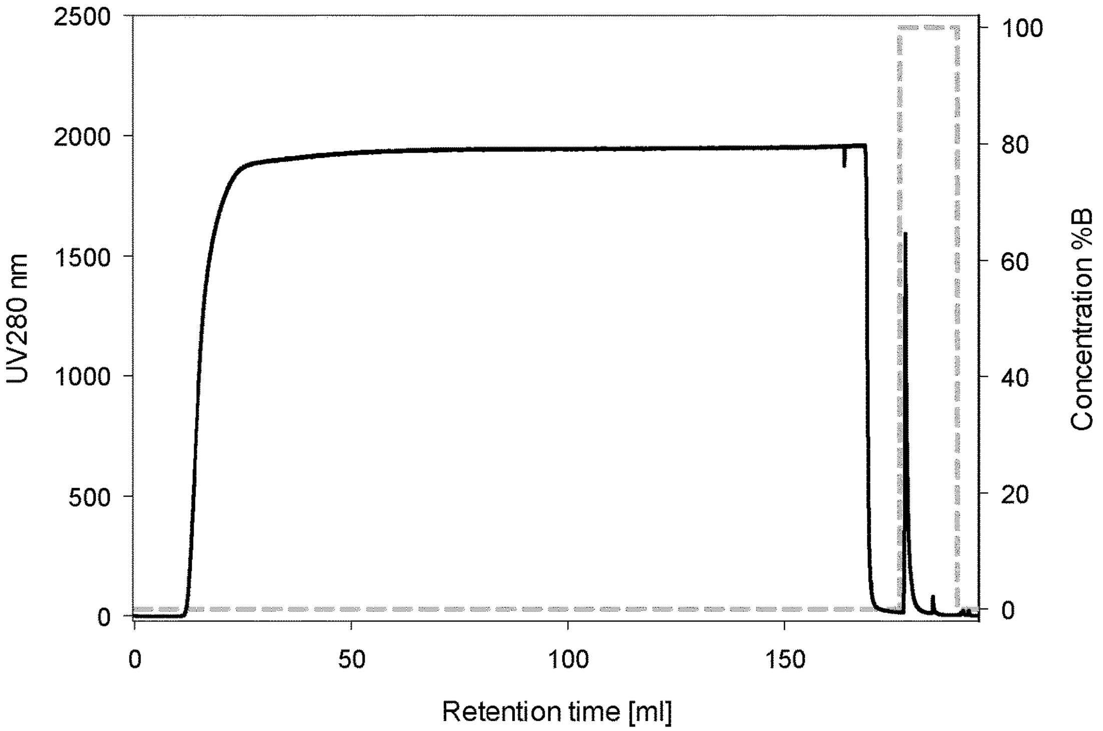
FIGURE 6: SDS-PAGE of analyzed fractions from SBC-Determination
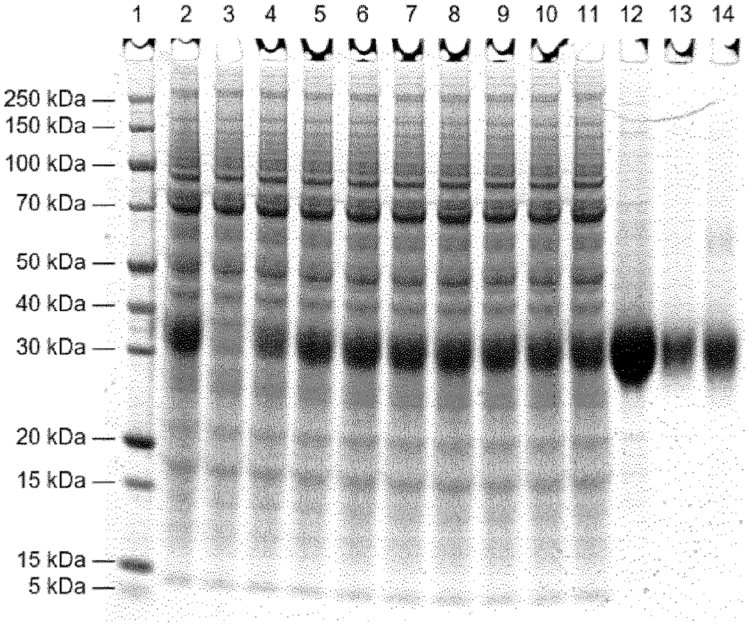

FIGURE 7: SDS-PAGE of purified SARS-CoV2-RBD-His with resin with immobilized fusion protein comprising SEQ ID NO: 28 (212896)
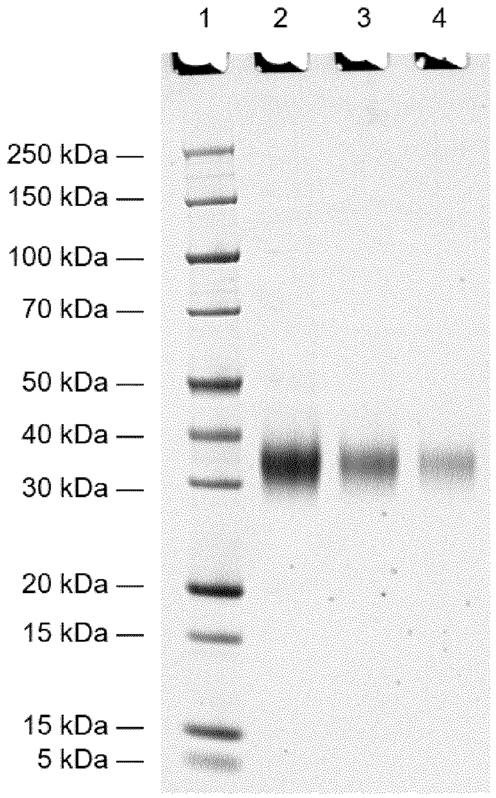

FIGURE 8: Affinity measurement (SPR) of SARS-CoV2-RBD purified via the 212896-resin
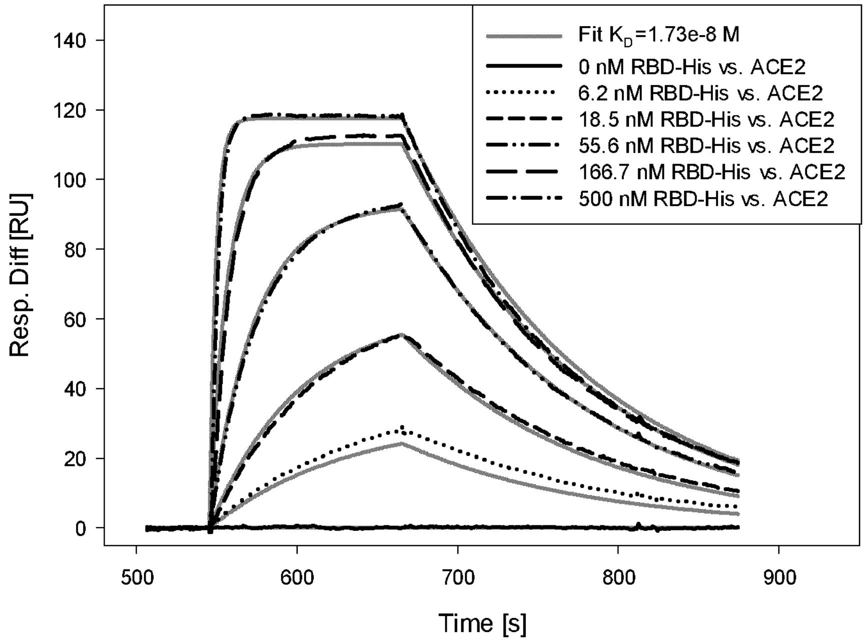
FIGURE 9: Detection of SARS-CoV2-S1 binding protein in Protein A ELISA
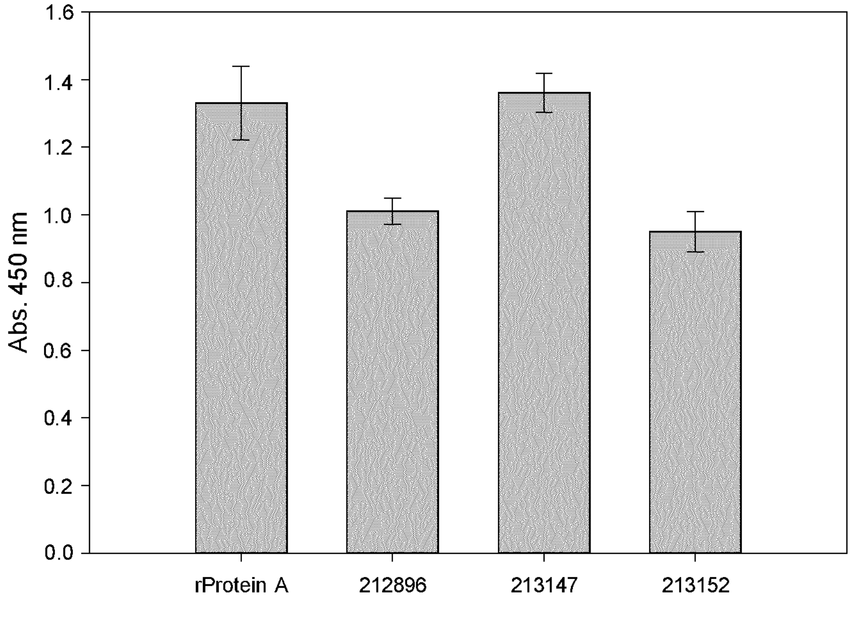

BINDING PROTEIN SPECIFIC FOR THE SPIKE PROTEIN OF SEVERE ACUTE RESPIRATORY SYNDROME CORONA VIRUS 2 (SARS-CoV-2)

CROSS REFERENCE TO RELATED APPLICATIONS

The present application is a United States National Stage Application of PCT International Patent Application Serial No. PCT/EP2021/067257, filed Jun. 23, 2021, which itself claims the benefit of the following European Patent Applications: EP 20181725.1, filed Jun. 23, 2020; EP 20186603.5, filed Jul. 17, 2020; EP 20188821.1, filed Jul. 31, 2020; and EP 2021357.9, filed Oct. 12, 2020. The disclosure of each of these application is incorporated herein by reference in its entirety.

TECHNICAL FIELD

The present invention relates to novel proteins that specifically bind to the spike protein or domains thereof of the severe acute respiratory syndrome corona virus 2 (SARS-Cov-2) or variants of SARS-Cov-2. The proteins of the present invention represent advanced and powerful tools, for example for the purification of the virus or a vaccine for the virus, by virtue of said binding affinity for spike protein or domains of the spike protein of SARS-Cov-2 or variants thereof. Thus, the novel proteins of the present invention are particularly advantageous because they allow precise capturing of proteins or particles comprising spike proteins, S1 domain, and/or RBD in affinity chromatography. Further, the novel proteins of the present invention can be used in medical applications caused by or related to SARS-Cov-2 or variants thereof.

BACKGROUND OF THE INVENTION

The severe acute respiratory syndrome corona virus 2 (SARS-Cov-2) is the cause for the pandemic virus disease COVID-19. The SARS-Cov-2 virus binds via glycoprotein S (spike protein) to the angiotensin-converting enzyme ACE2 receptor of the host cell. Functionally, the spike protein is characterized by two domains: S1 and S2. The S1 domain is responsible for the binding of the ACE2 receptor on the host cell; the species variable receptor binding domain (RBD) is located within the S1 domain. After binding of S1 domain to ACE2, the spike protein in cleaved in S1 domain and S2 domain by a serine protease TMPRSS2. The S2 domain is responsible for the fusion of the virus to the cell membrane which results in entry to the host cell. Upon entry, the viral genome is released to the cytoplasm of the host cell and can be translated directly from the cellular translation complex. New virus particles are assembled and exported as cause for the pandemic disease COVID-19 with severe and less-severe symptoms.

To stop the pandemic, at least ⅔ of the population should be immune. Therefore, the development of a vaccination against the virus is currently of great interest. The spike protein is the primary target in the development of vaccines, in particular the S1 domain or receptor binding domain (RBD) of the spike protein. Therefore, it will be of great importance to have efficient and reliable methods for the purification of spike protein (or domain thereof) based vaccines. Further, early detection of the virus or variants of the virus is of highest interest, as well as novel therapeutic options.

The present invention meets this need by providing novel binding proteins for the spike protein of SARS-Cov-2. These novel binding proteins are particularly advantageous because they allow a precise capturing in affinity chromatography as well as potential applications in medicine, particularly in diagnostic applications or in therapeutic applications.

The above overview does not necessarily describe all problems solved by the present invention.

SUMMARY OF THE INVENTION

The present disclosure provides the following items 1 to 14, without being specifically limited thereto:

1. A binding protein for the spike protein of severe acute respiratory syndrome corona virus 2 (SARS-Cov-2) comprising an amino acid sequence with at least 80% sequence identity to any one selected from the group of SEQ ID NOs: 1, 27, 28, and 65, wherein the binding protein has a binding affinity of less than 500 nM for the spike protein or domains thereof.
2. The binding protein for the spike protein according to item 1, wherein the binding protein has a binding affinity of less than 500 nM for the S1 domain of the spike protein, preferably wherein the binding protein has a binding affinity of less than 100 nM for the S1 domain of the spike protein. In various embodiments, the binding protein has a binding affinity of less than 500 nM, preferably less than 100 nM, for the receptor binding domain (RBD) of the spike protein.
3. The binding protein for the spike protein according to item 1 or 2, wherein 2, 3, 4, 5, or 6 binding proteins for the spike protein are linked to each other.
4. The binding protein for the spike protein according to item 3, wherein the binding protein is a homo-multimer or a hetero-multimer.
5. The binding protein for the spike protein according to item 4, wherein the binding protein comprises amino acid sequences with at least 80% sequence identity to SEQ ID NO: 63 or 64.
6. The binding protein for the spike protein according to any one of items 1-6, wherein the binding protein is fused to or conjugated to at least one further molecule, preferably selected from the group of (a) non-Immunoglobulin (Ig)-binding protein, (b) a diagnostically active moiety, optionally selected from a radionuclide, fluorescent protein, photosensitizer, dye, or enzyme, or any combination of the above (c) a therapeutically active moiety, optionally selected from a monoclonal antibody or a fragment thereof, a binding protein, a receptor or receptor domain, a receptor binding ligand or antagonist, a radionuclide, a cytotoxic compound, a cytokine, a chemokine, an enzyme, or derivatives thereof, or any combination of the above.
7. The binding protein for the spike protein according to any one of items 1-6 for use in medical applications, preferably for use in the diagnosis or treatment of diseases related to or caused by SARS CoV-2 or variants thereof.
8. The binding protein for the spike protein according to any one of items 1-6 for use in technical applications such as affinity purification of a spike protein or a protein comprising a spike protein domain or a particle containing a spike protein or domain thereof.
9. An affinity separation matrix comprising a binding protein for the spike protein according to any one of items 1-6.

10. Use of the binding protein for the spike protein according to any one of items 1-6, or the affinity separation matrix according to item 9, for affinity purification of a spike protein or a protein comprising a spike protein domain or a particle containing a spike protein or domain.
11. A method of affinity purification of spike protein or a domain thereof or of a particle comprising spike protein or a domain thereof, optionally a virus particle, the method comprising: (a) providing a liquid that contains a spike protein or a domain thereof (e.g. a particle comprising spike protein or domain); (b) providing an affinity separation matrix comprising at least one binding protein for spike protein or a domain thereof according to any one of items 1-6 coupled to said affinity separation matrix; (c) contacting said affinity separation matrix with the liquid under conditions that permit binding of the at least one binding protein for spike protein or a domain thereof according to any one of items 1-6; and (d) eluting said spike protein or a domain thereof or particle comprising the spike protein or domain thereof from said affinity purification matrix.
12. Use of the binding protein for the spike protein according to items 1-6, in methods to determine the presence of the spike protein or a domain thereof, or to determine the presence of a particle comprising the spike protein or domain thereof.
13. A method of analyzing the presence of spike protein or a domain thereof or particle comprising a spike protein or domain thereof in liquid samples, the method comprising the following steps:
    (i) providing a liquid that contains spike protein or a domain thereof or particle comprising a spike protein or domain,
    (ii) providing the binding protein for the spike protein according to items 1-6,
    (iii) contacting the liquid of (i) with the binding protein for the spike protein or a domain thereof according to items 1-6 under conditions that permit binding of the binding protein to the spike protein or a domain thereof,
    (iv) isolating the complex of spike protein or a domain thereof or particle and the binding protein for the spike protein or a domain thereof according to items 1-6, and
    (v) determining the amount of the binding protein for the spike protein according to items 1-6 in the liquid of (i).
14. A polynucleotide encoding the binding protein according to any one of items 1-6.

This summary of the invention is not limiting, and other aspects and embodiments of the invention will become evident from the following description, examples and drawings.

BRIEF DESCRIPTION OF THE FIGURES

FIG. 1 shows the amino acid sequences of binding proteins for the spike glycoprotein (and domains thereof) of SARS-Cov-2.

FIG. 2: FIG. 2A shows the Pool-ELISA after phage display selection for specific spike protein binding proteins (selected for S1 and RBD). FIG. 2B shows the octet analysis of p-scale purified spike protein binding proteins.

FIG. 3 shows a competitive binding study (SPR), in particular the binding of 212434 (SEQ ID NO: 1) to S1 and to RBD. If S1 and ACE2 or if RBD and ACE2 are applied at the same time to 212434, almost no binding is observed. It is concluded that the spike protein binding protein 212434 binds to the same or an overlapping epitope for S1 or RBD and ACE.

FIG. 4 shows the elution pH profile of fusion protein 212895 (SEQ ID NO: 29) in AIC experiments. 212895 comprises spike binding protein 212434 (SEQ ID NO: 1). Expressed SARS-CoV2-RBD-His target in Expi293-F cells was applied on packed resin with immobilized 212895 (UV280 nm: solid black line). Elution was performed by decreasing pH (pH trace: solid light grey line) with linear gradient (concentration % B: dashed dark grey line) from pH 6.0 to 2.0. Elution pH was determined by pH of fractions containing the target protein.

FIG. 5 shows the SBC determination of fusion protein comprising SEQ ID NO: 28 (212896). UV280 nm trace of SBC chromatogram (solid black line). Elution is performed in a single sharp peak at pH 3.4 (Concentration % B: dashed grey line). Fractions of flowthrough and elution peak were collected and analyzed via SDS-PAGE.

FIG. 6 shows the SDS-PAGE of analyzed fractions from SBC-Determination (see FIG. 5). Purified target SARS-CoV2-RBD-His between MW band 30-40 kDa is significantly overexpressed in the cell culture supernatant. Extraction of the target is visible in the first flow through fraction. 100% target breakthrough is ensured in the following fractions. Extracted target with high purity is presented in the eluted fraction. Lane 1: PageRuler Unstained Protein Ladder, lane 2: Load cell culture supernatant with overexpressed SARS-CoV2-RBD-His, lane 3-11: flowthrough fractions, lane 12-14: elution fractions.

FIG. 7 shows the SDS-PAGE of purified SARS-CoV2-RBD-His with 212896 resin. Purified SARS-CoV2-RBD-His from cell culture supernatant with 212896 resin was analyzed with SDS-PAGE. Different amounts of neutralized elution fraction was applied. No significant impurities were detected. Lane 1: PageRuler Unstained Protein Ladder, lane 2: 2 μg elution fraction, lane 3: 1 μg elution fraction, lane 4: 0.5 μg elution fraction.

FIG. 8 shows the affinity measurement of purified SARS-CoV2-RBD-His in SPR. Neutralized SARS-CoV2-RBD-His fraction from 212896 resin was investigated for binding vs. immobilized ACE2-Fc Receptor via rProtein A Sensor.

FIG. 9 shows the detection of SARS-CoV2-S1 binding protein in Protein A ELISA. SARS-CoV2-S1 binding proteins were analyzed for detection in protein A detection ELISA kit to evaluate possible ligand leaching detection. All fusion proteins show comparable detectability to internal rProtein A Kit standard ("rProtein A"). 212896 refers to a fusion protein comprising spike binding protein of SEQ ID NO: 28. 213147 refers to a fusion protein comprising spike binding proteins of SEQ ID NO: 26 and SEQ ID NO: 3 (dimer shown in SEQ ID NO: 9; 213103). 213152 refers to a fusion protein comprising spike binding proteins of SEQ ID NO: 21 and SEQ ID NO: 22 (dimer shown in SEQ ID NO: 18; 212728). All fusion proteins also comprise two or three non-Ig binding proteins of SEQ ID NO: 14.

DETAILED DESCRIPTION OF THE INVENTION

The present invention provides novel proteins having specific binding affinity for the spike glycoprotein of SARS-Cov-2. The proteins of the present invention represent advanced and powerful tools, for example for the purification of the virus or a vaccine for the virus, by virtue of said binding affinity for spike protein or domains of the spike protein of SARS-Cov-2 or variants thereof. Thus, the novel proteins of the present invention are particularly advantageous because they allow precise capturing of spike proteins or proteins comprising S1 domain or proteins comprising RBD or particles containing those viral proteins in affinity chromatography. Further, the novel proteins of the present invention can be used in medical applications related to SARS-Cov-2 or variants thereof. The binding affinity for the spike protein or domains thereof is given by a polypeptide comprising SEQ ID NO: 1, SEQ ID NO: 27, SEQ ID NO: 28, or SEQ ID NO: 65, or an amino acid sequence with at least 80% sequence identity, preferably at least 85% sequence identity, to any one of SEQ ID NOs: 1, 27, 28, and 65.

Before the present invention is described in more detail below it is to be understood that this invention is not limited to the particular methodology, protocols and reagents described herein as these may vary. It is also to be understood that the terminology used herein is for the purpose of describing particular aspects and embodiments only and is not intended to limit the scope of the present invention, which is reflected by the appended items. Unless defined otherwise, all technical and scientific terms used herein have the same meaning as commonly understood by one of ordinary skill in the art to which this invention belongs. This includes a skilled person working in the field of protein engineering and purification, but also including a skilled person working in the field of developing new specific binding molecules for the spike glycoprotein or domains thereof for use in technical applications such as affinity chromatography.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the items, which follow, unless the context requires otherwise, the word "comprise", and variants such as "comprises" and "comprising", will be understood to imply the inclusion of a stated integer or step, or group of integers or steps, but not the exclusion of any other integer or step or group of integers or steps. The term "comprise(s)" or "comprising" may encompass a limitation to "consists of" or "consisting of", should such a limitation be necessary for any reason and to any extent.

Several documents (for example: patents, patent applications, scientific publications, manufacturer's specifications, instructions, GenBank Accession Number, etc.) may be cited throughout the present specification. Nothing herein is to be construed as an admission that the invention is not entitled to antedate such disclosure by virtue of prior invention. Some of the documents cited herein may be characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, forms part of the disclosure content of the present specification.

General Definitions of Important terms used in the Application

The term "SARS-Cov-2" as used herein, refers to the severe acute respiratory syndrome corona virus 2, or variants thereof, including mutants or related viruses.

The terms "spike protein" or "spike glycoprotein" or "surface glycoprotein" or "spike glycoprotein S" or "COVID-19" may be used interchangeably herein and refer to an amino acid sequence as shown in GenBank ID: QHD43416.1, or variants thereof. The term "spike protein" comprises all polypeptides which show an amino acid sequence identity of at least 70%, 80%, 85%, 90%, 95%, 96% or 97% or more, or 100% to GenBank ID: QHD43416.1 (SEQ ID NO: 10). As described herein, the term "spike protein" comprises, without being limited thereto, polypeptides of SARS-Cov-2 variants that emerged in the United Kingdom ("B.1.1.7"), South Africa ("B.1.351"), Brazil ("P.1"), and India ("B.1.617.2"). On May 31, 2021, the WHO (World Health Organization) has announced that these variants are named, according to WHO label, variant Alpha ("B.1.1.7"), Beta ("B.1.351"), Gamma ("P.1"), and Delta ("B.1.617.2"), respectively. The term "spike protein" also comprises polypeptides of SARS-Cov-2 variants named, according to the WHO label, Epsilon ("B.1.427/B.1.429"), Zeta ("P.2"), Eta ("B.1.525"), Theta ("P.3"), Iota ("B.1.526"), and Kappa ("B.1.617.1").

In various embodiments, the binding proteins of the present invention may show binding affinity as described elsewhere herein for the spike protein of any of variants Alpha ("B.1.1.7"), Beta ("B.1.351"), Gamma ("P.1"), Delta ("B.1.617.2"), Epsilon ("B.1.427/B.1.429"), Zeta ("P.2"), Eta ("B.1.525"), Theta ("P.3"), Iota ("B.1.526"), and Kappa ("B.1.617.1"). In preferred embodiments, the binding proteins of the present invention show binding affinity as described elsewhere herein for the spike protein of variant Alpha ("B.1.1.7") and/or variant Delta ("B.1.617.2").

The term "S1 domain" or "S1" or "S1 subunit" or "S1 protein" or "spike glycoprotein Subunit 1" or "S glycoprotein subunit 1" or "spike protein S1" as used herein, refers to any S1 domain of the spike glycoprotein or variants thereof. Amino acids at positions 16-685 of GenBank ID: QHD43416.1 correspond to the S1 domain of the spike protein or variant thereof. The term "S1 domain" comprises all polypeptides which show an amino acid sequence identity of at least 70%, 80%, 85%, 90%, 95%, 96% or 97% or more, or 100% to amino acids at positions 16-685 of GenBank ID: QHD43416.1 (SEQ ID NO: 11). The term "S1 domain" comprises in particular S1 domains of polypeptides of SARS-Cov-2 variants described above, more specifically variants Alpha ("B.1.1.7"), Beta ("B.1.351"), Gamma ("P.1"), Delta ("B.1.617.2"), Epsilon ("B.1.427/B.1.429"), Zeta ("P.2"), Eta ("B.1.525"), Theta ("P.3"), Iota ("B.1.526"), and Kappa ("B.1.617.1"), wherein the S1 domains of the respective SARS-Cov-2 variants essentially correspond with regard to their positions in the spike protein to positions 16-685 of the sequence of GenBank ID: QHD43416.1, or essentially correspond to the sequence of the S1 domain shown in SEQ ID NO: 11.

The term "receptor binding domain" or "RBD" or "SARS-CoV-S2 S protein RBD" or "S protein RBD" or "spike glycoprotein receptor-binding domain" or "spike protein RBD" is part of the S1 domain of the spike protein and corresponds to amino acids at positions 319-541 of GenBank ID: QHD43416.1. The term "RBD" comprises all polypeptides which show an amino acid sequence identity of at least 70%, 80%, 85%, 90%, 95%, 96% or 97% or more, or 100% to amino acids 319-541 of GenBank ID: QHD43416.1 (SEQ ID NO: 12). The term "RBD" comprises in particular RBDs of polypeptides of SARS-Cov-2 variants described above, more specifically variants Alpha ("B.1.1.7"), Beta ("B.1.351"), Gamma ("P.1"), Delta ("B.1.617.2"), Epsilon ("B.1.427/B.1.429"), Zeta ("P.2"), Eta ("B.1.525"), Theta ("P.3"), Iota ("B.1.526"), and Kappa ("B.1.617.1") wherein the RBDs of the respective SARS-Cov-2 variants essentially correspond with regard to their positions in the S1 domain to positions 319-541 of the sequence of GenBank ID: QHD43416.1, or essentially correspond to the sequence of the RBD shown in SEQ ID NO: 12.

The term "binding protein for the spike protein or domains thereof" or "affinity ligand for the spike protein or domains thereof" describes a protein that is capable to bind to the spike protein and/or the S1 domain of the spike glycoprotein and/or the RBD as described herein, including the S1 domains and/or RBDs of polypeptides of SARS-Cov-2 variants described herein. As described herein, a "binding protein for the spike protein or domains thereof" or "affinity ligand for the spike protein or domains thereof" refers to a protein with detectable interaction with the spike protein domain and/or the S1 domain and/or the RBD, as determined by suitable methods such as for example SPR analysis or any other appropriate technology known to someone skilled in the art.

The binding protein for the spike protein may bind to the RBD. A binding protein for the spike protein may bind to S1 domain. A binding protein for the spike protein may bind to a particle, for example a virus particle, comprising a spike protein and/or S1 domain and/or RBD. Preferably, the binding affinity is 500 nM for the spike protein, and/or 500 nM for the S1 domain, and/or 500 nM for the RBD. More preferably, the binding affinity is 100 nM for the spike protein, and/or 100 nM for the S1 domain, and/or 100 nM for the RBD.

The terms "binding affinity" and "binding activity" may be used herein interchangeably and they refer to the ability of a polypeptide of the invention to bind to another protein, peptide, or fragment or domain thereof. Binding affinity is typically measured and reported by the equilibrium dissociation constant ($K_D$) (usually measured in "mol/L", sometimes abbreviated as "M"), which is used to evaluate and rank the strength of bimolecular interactions, in particular the interaction between a first protein and a second protein. The binding affinity and dissociation constants can be measured quantitatively. Methods for determining binding affinities are well known to the skilled person and can be selected, for instance, from the following methods that are well established in the art: surface plasmon resonance (SPR) spectroscopy, enzyme-linked immunosorbent assay (ELISA), kinetic exclusion analysis (KinExA assay), Bio-layer interferometry (BLI), flow cytometry, fluorescence spectroscopy techniques, isothermal titration calorimetry (ITC), analytical ultracentrifugation, radioimmunoassay (RIA or IRMA), and enhanced chemiluminescence (ECL). Typically, the dissociation constant $K_D$ is determined at temperatures in the range of 20° C. and 30° C. If not specifically indicated otherwise, $K_D$ values recited herein are determined at 25° C. by SPR. The most widely used SPR-based system is the BIAcore, produced by BIAcore AB. In various embodiments of the present invention, the binding affinity for SARS-Cov-2 may be determined by the BIAcore SPR system.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide.

As used herein, the term "linker" refers in its broadest meaning to a molecule that covalently joins at least two other molecules.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein or polypeptide, for example, to the polypeptide of SEQ ID NO: 1. Methods for sequence alignment are well known in the art. For example, for determining the extent of an amino acid sequence identity of an arbitrary polypeptide relative to the amino acid sequence of, for example, SEQ ID NO: 1, the SIM Local similarity program is preferably employed (Xiaoquin Huang and Webb Miller (1991), Advances in Applied Mathematics, vol. 12: 337-357), that is freely available. For multiple alignment analysis, ClustalW is preferably used (Thompson et al. (1994) Nucleic Acids Res., 22(22): 4673-4680).

The terms "protein" and "polypeptide" refer to any chain of two or more amino acids linked by peptide bonds and does not refer to a specific length of the product. Thus, "peptides", "protein", "amino acid chain", or any other term used to refer to a chain of two or more amino acids, are included within the definition of "polypeptide", and the term "polypeptide" may be used instead of, or interchangeably with, any of these terms. The term "polypeptide" is also intended to refer to the products of post-translational modifications of the polypeptide like, e.g., glycosylation, which are well known in the art.

The term "alkaline stable" or "alkaline stability" or "caustic stable" or "caustic stability" refers to the ability of the binding protein for the spike protein to withstand alkaline conditions without significantly losing the ability to bind to the S1 domain of the spike protein of SARS-Cov-2. The skilled person in this field can easily test alkaline stability by incubating an spike protein of Binding protein for the spike protein with sodium hydroxide solutions, e.g., as described in the Examples, and subsequent testing of the binding activity to the spike protein S1 by routine experiments known to someone skilled in the art, for example, by chromatographic approaches. The alkaline stability may be determined by coupling a spike protein binding protein of the invention to a surface plasmon resonance (SPR) sensor chip and assaying the binding capacity or binding activity for the S1 domain before and after exposure to an alkaline solution. The alkaline treatment may be performed, for instance, in 0.1 M NaOH for an extended period of time, e.g., at least 10 h, at room temperature (22° C. +/−3° C.). As further described herein, binding proteins of the invention, in particular fusion proteins, may retain at least 70%, or at least 85%, or at least 90%, binding affinity for the S1 domain or RBD after exposure to alkaline conditions as described herein. In various embodiments, the binding proteins of the invention retain binding affinity for the S1 domain or RBD as described above when immobilized to a solid support, preferably to a solid support of an affinity separation matrix.

The term "chromatography" refers to separation technologies which employ a mobile phase and a stationary phase to separate one type of molecules (e.g., the spike protein or a protein comprising a S1 domain or a protein comprising a RBD) from other molecules (e.g., contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand (i.e. a binding protein for the spike protein or domains thereof) coupled to a stationary phase interacts with a molecule (i.e. protein comprising spike protein or a domain thereof) in the mobile phase (the sample) i.e. the ligand has a specific binding affinity for the molecule to be purified. As understood in the context of the invention, affinity chromatography involves the addition of a sample containing a protein comprising spike protein or a domain thereof to a stationary phase which comprises a chromatography ligand, such as a binding protein for the spike protein. The terms "solid support" or "solid matrix" are used interchangeably for the stationary phase.

The terms "affinity matrix" or "affinity purification matrix" or "affinity chromatography matrix", as used interchangeably herein, refer to a matrix, e.g., a chromatographic matrix, onto which an affinity ligand e.g., a binding protein for the spike protein or a domain thereof is attached. The attached affinity ligand (e.g., binding protein for the spike protein or a domain thereof) is capable of specific binding to a molecule of interest (e.g., SARS-Cov-2 or variants thereof or related viruses) which is to be purified or removed from a mixture (e.g., in a liquid sample).

The term "affinity purification" as used herein refers to a method of purifying a protein comprising spike protein or a domain thereof from a liquid (sample) by binding the protein or particle comprising spike protein or a domain thereof to binding protein for the spike protein or a domain thereof that is immobilized to a matrix. Thereby, other components of the mixture except protein or particle comprising S1 are removed. In a further step, the bound protein or particle comprising the spike protein or a domain thereof can be eluted and obtained in highly purified form.

Detailed Description of Embodiments of the Invention

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

The novel binding protein for the spike protein or a domain thereof exhibit a high binding affinity for the spike protein or a domain thereof of SARS-Cov-2. The binding protein for the spike protein or a domain thereof comprises an amino acid sequence selected from the group of SEQ ID NO: 1, SEQ ID NO: 27, SEQ ID NO: 28, or SEQ ID NO: 65, or an amino acid with at least 80% sequence identity, preferably at least 85% sequence identity, to any one of SEQ ID NOs: 1, 27, 28, and 65.

In some embodiments, the binding protein for the spike protein has at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to any one of the amino sequences of SEQ ID NOs: 1, 27, 28, 65. In various embodiments described herein referring to at least 80% sequence identity, the 35 sequence identity may preferably be any of at least 90%, 91%, 92%, 93%, 94%, or 95%, identity to the respective reference sequence. In various other embodiments described herein referring to at least 85% sequence identity, the sequence identity may preferably be any of at least 90%, 91%, 92%, 93%, 94%, or 95%, identity to the respective reference sequence.

In some embodiments, the binding protein for the spike protein or a domain thereof is comprising an amino acid sequence with at least 85% sequence identity to at least 56 amino acids of SEQ ID NO: 65: NAAVLDI$X_1$QH$X_2$ATEEIWWLPNLTKQQKVWFIMSLTQDPSVS$X_3$E$X_4$L$X_5$EA$X_6$KLN D$X_7$QAPK, wherein position $X_1$ is selected from any amino acid, preferably from A or D, wherein position $X_2$ is selected from any amino acid, preferably from S or A, wherein position $X_3$ is selected from any amino acid, preferably from K or L, wherein position $X_4$ is selected from any amino acid, preferably from V or I, wherein position $X_5$ is selected from any amino acid, preferably from G or A, wherein position $X_6$ is selected from any amino acid, preferably from Q or K, wherein position $X_7$ is selected from any amino acid, preferably from S or A.

In further embodiments, the amino acids at positions selected from any of positions 4, 5, 7, 10, 13, 14, 17, 18, 24, 25, 27, 28, 29, 32, 35, and 36 are any of 4V, 5L, 7I, 10H, 13T, 14E, 17W, 18W, 24K, 25Q, 27K, 28V, 29W, 32M, 35T, and/or 36Q.

In some embodiments, the binding protein for the spike protein or a domain thereof is comprising an amino acid sequence with at least 85% sequence identity to at least 56 amino acids of SEQ ID NO: 1: NAAVLDIAQHSATEE-IWWLPNLTKQQKVWFIMSLTQDPSVSKEVLGEA-QKLNDSQAPK. In various embodiments, the amino acids at the positions corresponding to positions 8, 11, 42, 44, 46, 49, and 54 are (A or D), (S or A), (K or L), (V or I), (G or A), (Q or K), and/or (S or A), respectively. In preferred embodiments, the amino acids at the positions corresponding to positions 8, 11, 42, 44, 46, 49, and 54 are D, A, L, I, A, K, and A, respectively. In further embodiments, the amino acids at positions selected from any of positions 4, 5, 7, 10, 13, 14, 17, 18, 24, 25, 27, 28, 29, 32, 35, and 36 are any of 4V, 5L, 7I, 10H, 13T, 14E, 17W, 18W, 24K, 25Q, 27K, 28V, 29W, 32M, 35T, and/or 36Q.

In some embodiments, the binding protein for the spike protein or a domain thereof is comprising an amino acid sequence with at least 85% sequence identity to SEQ ID NO: 27. In various embodiments, the amino acids at the positions corresponding to positions 6, 9, 40, 42, 44, 47, and 52 are (A or D), (S or A), (K or L), (V or I), (G or A), (Q or K), and/or (S or A), respectively. In preferred embodiments, the amino acids at the positions corresponding to positions 6, 9, 40, 42, 44, 47, and 52 are D, A, L, I, A, K, and A, respectively. In further embodiments, the amino acids at positions selected from any of positions 2, 3, 5, 8, 11, 12, 15, 16, 22, 23, 25, 26, 27, 30, 33, and 34 are any of 2V, 3L, 5I, 8H, 11T, 12E, 15W, 16W, 22K, 23Q, 25K, 26V, 27W, 30M, 33T, and/or 34Q, respectively.

In some embodiments, the binding protein for the spike protein or a domain thereof is comprising an amino acid sequence with at least 85% sequence identity to SEQ ID NO: 28: AVLDIDQHAATEEIVWVLPNLTKQQKVWFIM-SLTQDPSVSLEILAEAKKLNDAQAPK. In various embodiments, the amino acids at the positions corresponding to positions 6, 9, 40, 42, 44, 47, and 52 are (A or D), (S or A), (K or L), (V or I), (G or A), (Q or K), and/or (S or A), respectively. In preferred embodiments, the amino acids at the positions corresponding to positions 6, 9, 40, 42, 44, 47, and 52 are D, A, L, I, A, K, and A, respectively. In further embodiments, the amino acids at positions selected from any of positions 2, 3, 5, 8, 11, 12, 15, 16, 22, 23, 25, 26, 27, 30, 33, and 34 are any of 2V, 3L, 5I, 8H, 11T, 12E, 15W, 16W, 22K, 23Q, 25K, 26V, 27W, 30M, 33T, and/or 34Q, respectively.

In various embodiments, in the binding proteins of the invention, the amino acid at the position corresponding to position 4 in SEQ ID NO: 15 is not K. In various embodiments, in the binding proteins of the invention, the amino acid at the position corresponding to position 4 in SEQ ID NO: 1 or 65, or SEQ ID NO: 15, is V.

In various embodiments, in the binding proteins of the invention, the amino acid at the position corresponding to position 5 in SEQ ID NO: 15 is not F. In various embodiments, in the binding proteins of the invention, the amino acid at the position corresponding to position 5 in SEQ ID NO: 1 or 65, or SEQ ID NO: 15, is L.

In various embodiments, in the binding proteins of the invention, the amino acid at the position corresponding to position 7 in SEQ ID NO: 15 is not E. In various embodiments, in the binding proteins of the invention, the amino acid at the position corresponding to position 7 in SEQ ID NO: 1 or 65, or SEQ ID NO: 15, is I.

In various embodiments, in the binding proteins of the invention, the amino acid at the position corresponding to position 10 in SEQ ID NO: 15 is not Q. In various embodiments, in the binding proteins of the invention, the amino acid at the position corresponding to position 10 in SEQ ID NO: 1 or 65, or SEQ ID NO: 15, is H.

In various embodiments, in the binding proteins of the invention, the amino acid at the position corresponding to position 13 in SEQ ID NO: 15 is not F. In various embodiments, in the binding proteins of the invention, the amino acid at the position corresponding to position 13 in SEQ ID NO: 1 or 65, or SEQ ID NO: 15, is T.

In various embodiments, in the binding proteins of the invention, the amino acid at the position corresponding to position 14 in SEQ ID NO: 15 is not Y. In various embodiments, in the binding proteins of the invention, the amino acid at the position corresponding to position 14 in SEQ ID NO: 1 or 65, or SEQ ID NO: 15, is E.

In various embodiments, in the binding proteins of the invention, the amino acid at the position corresponding to position 17 in SEQ ID NO: 15 is not L. In various embodiments, in the binding proteins of the invention, the amino acid at the position corresponding to position 17 in SEQ ID NO: 1 or 65, or SEQ ID NO: 15, is W.

In various embodiments, in the binding proteins of the invention, the amino acid at the position corresponding to position 18 in SEQ ID NO: 15 is not H. In various embodiments, in the binding proteins of the invention, the amino acid at the position corresponding to position 18 in SEQ ID NO: 1 or 65, or SEQ ID NO: 15, is W.

In various embodiments, in the binding proteins of the invention, the amino acid at the position corresponding to position 24 in SEQ ID NO: 15 is not E. In various embodiments, in the binding proteins of the invention, the amino acid at the position corresponding to position 24 in SEQ ID NO: 1 or 65, or SEQ ID NO: 15, is K.

In various embodiments, in the binding proteins of the invention, the amino acid at the position corresponding to position 25 in SEQ ID NO: 15 is not E. In various embodiments, in the binding proteins of the invention, the amino acid at the position corresponding to position 25 in SEQ ID NO: 1 or 65, or SEQ ID NO: 15, is Q.

In various embodiments, in the binding proteins of the invention, the amino acid at the position corresponding to position 27 in SEQ ID NO: 15 is not R. In various embodiments, in the binding proteins of the invention, the amino acid at the position corresponding to position 27 in SEQ ID NO: 1 or 65, or SEQ ID NO: 15, is K.

In various embodiments, in the binding proteins of the invention, the amino acid at the position corresponding to position 28 in SEQ ID NO: 15 is not N. In various embodiments, in the binding proteins of the invention, the amino acid at the position corresponding to position 28 in SEQ ID NO: 1 or 65, or SEQ ID NO: 15, is V.

In various embodiments, in the binding proteins of the invention, the amino acid at the position corresponding to position 29 in SEQ ID NO: 15 is not A. In various embodiments, in the binding proteins of the invention, the amino acid at the position corresponding to position 29 in SEQ ID NO: 1 or 65, or SEQ ID NO: 15, is W.

In various embodiments, in the binding proteins of the invention, the amino acid at the position corresponding to position 32 in SEQ ID NO: 15 is not Q. In various embodiments, in the binding proteins of the invention, the amino acid at the position corresponding to position 32 in SEQ ID NO: 1 or 65, or SEQ ID NO: 15, is M.

In various embodiments, in the binding proteins of the invention, the amino acid at the position corresponding to position 35 in SEQ ID NO: 15 is not R. In various embodiments, in the binding proteins of the invention, the amino acid at the position corresponding to position 35 in SEQ ID NO: 1 or 65, or SEQ ID NO: 15, is T.

In various embodiments, in the binding proteins of the invention, the amino acid at the position corresponding to position 36 in SEQ ID NO: 15 is not D. In various embodiments, in the binding proteins of the invention, the amino acid at the position corresponding to position 36 in SEQ ID NO: 1 or 65, or SEQ ID NO: 15, is Q.

In various embodiments, in the binding proteins of the invention, the amino acid at the positions corresponding to positions 4, 5, 7, 10, 13, 14, 17, 18, 24, 25, 27, 28, 29, 32, 35, and 36, in SEQ ID NO: 15 is not K, F, E, Q, F, Y, L, H, E, E, R, N, A, Q, R, and D, respectively. In various embodiments, in the binding proteins of the invention, the amino acid at the positions corresponding to positions 4, 5, 7, 10, 13, 14, 17, 18, 24, 25, 27, 28, 29, 32, 35, and 36, in SEQ ID NO: 1 or 65, or SEQ ID NO: 15, is V, L, I, H, T, E, W, W, K, Q, K, V, W, M, T, and Q, respectively.

In some embodiments, in the binding proteins of the invention, the amino acid at the positions corresponding to positions 8, 11, 42, 44, 46, 49, and 54, in SEQ ID NO: 1 or 65, or SEQ ID NO: 16, is A, S, K, V, G, Q, and S, respectively. In some embodiments, in the binding proteins of the invention, the amino acid at the positions corresponding to positions 8, 11, 42, 44, 46, 49, and 54, in SEQ ID NO: 1 or 65, or SEQ ID NO: 16, is not A, S, K, V, G, Q, and S, respectively. In other embodiments, in the binding proteins of the invention, the amino acid at the positions corresponding to positions 8, 11, 42, 44, 46, 49, and 54, in SEQ ID NO: 1 or 65, or SEQ ID NO: 16, is D, A, L, I, A, K, and A, respectively.

In various embodiments, a binding protein of the invention has, in comparison to the cs27 sequence of SEQ ID NO: 15, up to 16 amino substitutions at positions corresponding to positions selected from positions 4, 5, 7, 10, 13, 14, 17, 18, 24, 25, 27, 28, 29, 32, 35, and 36 in the sequence of SEQ ID NO: 1 or 65, or SEQ ID NO: 15.

In various embodiments, a binding protein of the invention has, in comparison to the cs27 sequence of SEQ ID NO: 15, up to 16 amino substitutions at positions corresponding to any of positions selected from positions 4, 5, 7, 10, 13, 14, 17, 18, 24, 25, 27, 28, 29, 32, 35, and 36 in the sequence of SEQ ID NO: 1 or 65, or SEQ ID NO: 15, wherein the substitutions are selected from any of K4V, FSL, E71, Q10H, F13T, Y14E, L17W, H18W, E24K, E25Q, R27K, N28V, A29W, Q32W, Q32M, R35T, and D36Q, relative to the sequence of SEQ ID NO: 15.

In various embodiments, positions corresponding to positions 1 and 2 of SEQ ID NO: 1 or 65, or the cs27 sequence of SEQ ID NO: 15, may be deleted in a binding protein of the invention.

One advantage of the disclosed binding protein for the spike protein is the important functional characteristic that it binds specifically to the spike protein or to a domain thereof. Needless to point out, that this is of particular advantage in the purification of proteins or particles comprising spike protein or a domain thereof, for example, vaccines specific for SARS-Cov-2. The binding protein for the S1 domain is functionally characterized by a binding affinity, preferably of less than 500 nM for the S1 domain of SARS-Cov-2. In some embodiments, the binding protein for the spike protein binds to spike protein or a domain thereof, preferably with a dissociation constant $K_D$ below 50 nM, or more preferably below 10 nM, as shown in Example 3.

The binding protein for the S1 domain binds highly specific to the S1 domain or RBD of SARS-Cov2. In some embodiments, the binding proteins of the invention bind highly specific to the S1 domain or RBD of variants of SARS-Cov-2, for example, to the British variant Alpha ("B.1.1.7").

In some embodiments, the binding proteins of the invention bind highly specific to the S1 domain or RBD of variants of SARS-Cov-2, for example, to the Indian variant Delta ("B.1.617.2"). No significant binding affinity to the S1 domain or RBD for severe acute respiratory syndrome corona virus 1 (SARS-Cov-1), could be observed. No significant binding affinity to the S1 domain or RBD of Middle East Respiratory Syndrome (MERS) Coronavirus (MERS-Cov) could be observed.

A common structural feature of the binding proteins is that they are based on artificial mosaic proteins that are stable under conditions as usually applied in affinity chromatography, for example, under alkaline conditions. For example, the general scaffold of the SARS Cov-2 S1 protein binding protein is a triple helical scaffold of at least 56 amino acids based on SEQ ID NO: 16. The artificial mosaic proteins have specific mutations that generate the unique and surprising SARS Cov-2 spike protein binding functionality.

Multimers. In one embodiment of the invention, the binding protein for the spike protein comprises 1, 2, 3, 4, 5, or 6 binding protein(s) linked to each other. Multimers of the binding protein are generated artificially, generally by recombinant DNA technology well-known to a skilled person. In some embodiments, the multimer is a homo-multimer, e.g. the amino acid sequences of binding protein for the spike protein are identical. For example, the homo-multimeric binding protein for the spike protein may comprise at least two monomers as shown in SEQ ID NO: 1 or SEQ ID NO: 28 (or at least 80% identical thereto) linked to each other in head-to-tail orientation (see SEQ ID NO: 64 and SEQ ID NO: 63, respectively). For example, the homo-multimeric binding protein for the spike protein may comprise at least two monomers as shown in SEQ ID NO: 1 (or at least 80%, preferably 92%, identical thereto) linked to each other in head-to-tail orientation. For example, the homo-multimeric binding protein for the spike protein may comprise at least two monomers as shown in SEQ ID NO: 28 (or at least 80%, preferably 92%, identical thereto) linked to each other in head-to-tail orientation.

In other embodiments, the multimer is a hetero-multimer, e.g. the amino acid sequences of the binding protein for the spike protein are different. According to preferred embodiments, the multimer or hetero-multimer is a (hetero)-dimer. In preferred embodiments, a (hetero)-dimer of the invention lacks the two N-terminal amino acids corresponding to the amino acids at positions 1 and 2 of SEQ ID NO: 1 or 65.

As described herein, the monomers of a multimer or hetero-multimer, preferably (hetero)-dimer, of the present invention may be linked in head-to-tail orientation. As further described herein, in a (hetero)-dimer, the first monomer may be considered as the N-terminal monomer or the N-terminally located monomer, and the second monomer may be considered as the C-terminal monomer or the C-terminally located monomer. In various embodiments pertaining to hetero-multimers, the one or more monomers located C-terminally of the first monomer may be identical.

In some embodiments, at least one monomer of the spike protein binding multimer has amino acid substitutions at any of positions corresponding to positions 4, 5, 7, 10, 13, 14, 17, 18, 24, 25, 27, 28, 29, 32, 35, and/or 36 in the sequence of SEQ ID NO: 15, as described elsewhere herein.

Optionally, position 1 and position 2 in the monomer are deleted. For example, the hetero-multimeric binding protein for the spike protein may comprise at least one monomer of any of SEQ ID NO: 1, SEQ ID NO: 27, SEQ ID NO: 28, or SEQ ID NO: 65, or variants thereof as disclosed elsewhere herein. In some embodiments, a hetero-multimeric protein is a (homo- or hetero-) dimer comprising at least one monomer of SEQ ID NO: 1 (or SEQ ID NO: 27, or SEQ ID NO: 28 or SEQ ID NO: 65) at the N-terminus or at the C-terminus. For example, the hetero-multimeric binding protein for the spike protein may comprise SEQ ID NO: 28 and SEQ ID NO: 7 linked to each other in head-to-tail orientation. For example, the hetero-multimeric binding protein for the spike protein may comprise SEQ ID NO: 7 and SEQ ID NO: 28 linked to each other in head-to-tail orientation. In various embodiments, positions corresponding to positions 1 and 2 of the sequence of SEQ ID NO: 1 may be deleted in the first and/or second monomer, as illustrated, e.g., in the sequence of SEQ ID NOs: 27 and 28.

The present invention encompasses multimers, in particular dimers, comprising a first (N-terminally located) monomer having at least 80% or at least 85% sequence identity to any of SEQ ID NOs: 1, 27, 28, or 65, preferably SEQ ID NO: 28, and a second monomer (C-terminally located relative to the first monomer) having at least 80% or at least 85 sequence identity to any of SEQ ID NOs: 1, 27, 28, or 65, preferably SEQ ID NO: 28. Preferably, the dimeric binding protein has a binding affinity of less than 500 nM, more preferably less than 100 nM, for the spike protein or domains thereof.

In various embodiments, the amino acids at the positions corresponding to positions 8, 11, 42, 44, 46, 49, and 54 of SEQ ID NO: 1 or 65 are (A or D), (S or A), (K or L), (V or I), (G or A), (Q or K), and/or (S or A), respectively. In preferred embodiments, the amino acids at the positions corresponding to positions 8, 11, 42, 44, 46, 49, and 54 of SEQ ID NO: 1 or 65 are D, A, L, I, A, K, and A, respectively. In further embodiments, the amino acids at positions selected from any of positions 4, 5, 7, 10, 13, 14, 17, 18, 24, 25, 27, 28, 29, 32, 35, and 36 of SEQ ID NO: 1 or 65 are any of 4V, 5L, 7I, 10H, 13T, 14E, 17W, 18W, 24K, 25Q, 27K, 28V, 29W, 32M, 35T, and/or 36Q.

In various embodiments, the amino acids at the positions corresponding to positions 6, 9, 40, 42, 44, 47, and 52 of SEQ ID NO: 27 or 28 are (A or D), (S or A), (K or L), (V or 1), (G or A), (Q or K), and/or (S or A), respectively. In preferred embodiments, the amino acids at the positions corresponding to positions 6, 9, 40, 42, 44, 47, and 52 of SEQ ID NO: 27 or 28 are D, A, L, 1, A, K, and A, respectively. In further embodiments, the amino acids at positions selected from any of positions 2, 3, 5, 8, 11, 12, 15, 16, 22, 23, 25, 26, 27, 30, 33, and 34 of SEQ ID NO: 27 or 28 are any of 2V, 3L, 51, 8H, 11T, 12E, 15W, 16W, 22K, 23Q, 25K, 26V, 27W, 30M, 33T, and/or 34Q, respectively.

In various embodiments, the multimer, in particular a dimer, has a deletion in the first monomer of the amino acids corresponding to the amino acids at positions 1 and 2 of SEQ ID NOs: 1 and 65, but does not have a deletion in the said second monomer of the amino acids corresponding to the amino acids at positions 1 and 2 of SEQ ID NOs: 1 and 65.

The present invention encompasses dimers having at least 80% or at least 85% sequence identity to SEQ ID NOs: 63 or 64. Preferably, the dimeric binding protein has a binding affinity of less than 500 nM, more preferably less than 100 nM, for the spike protein or domains thereof. In various embodiments, the amino acids at the positions corresponding to positions 6, 9, 40, 42, 44, 47, and 52 of SEQ ID NO: 63 or 64 are (A or D), (S or A), (K or L), (V or I), (G or A), (Q or K), and/or (S or A), respectively, and the amino acids at the positions corresponding to positions 64, 67, 98, 100, 102, 105, and 110 of SEQ ID NO: 63 or 64 are (A or D), (S or A), (K or L), (V or I), (G or A), (Q or K), and/or (S or A), respectively. In various preferred embodiments, the amino acids at the positions corresponding to positions 6, 9, 40, 42, 44, 47, and 52 of SEQ ID NO: 63 or 64 are D, A, L, I, A, K, and A, respectively, and the amino acids at the positions corresponding to positions 64, 67, 98, 100, 102, 105, and 110 of SEQ ID NO: 63 or 64 are D, A, L, I, A, K, and A, respectively. In further embodiments, the amino acids at positions selected from any of positions 2, 3, 5, 8, 11, 12, 15, 16, 22, 23, 25, 26, 27, 30, 33, and 34 of SEQ ID NO: 63 or 64 are any of 2V, 3L, 5I, 8H, 11T, 12E, 15W, 16W, 22K, 23Q, 25K, 26V, 27W, 30M, 33T, and/or 34Q, respectively, and the amino acids at positions selected from any of positions 60, 61, 63, 66, 69, 70, 73, 74, 80, 81, 83, 84, 85, 88, 91, and 92 of SEQ ID NO: 63 or 64 are any of 60V, 61L, 63I, 66H, 69T, 70E, 73W, 74W, 80K, 81Q, 83K, 84V, 85W, 88M, 91T, and/or 92Q, respectively.

In multimers, in particular dimers, of the present invention having a deletion of positions 1 and 2 in the N-terminal monomer, the amino acid at the position corresponding to position 57 of, e.g., SEQ ID NO: 63, may be Ile (1).

Additional moieties. In some embodiments, the binding protein for the spike protein or a domain thereof as described above further comprises or is fused to at least one further polypeptide distinct from the polypeptide as disclosed. In various embodiments, the further polypeptide fused to the binding protein for the spike protein and distinct from the binding protein for the spike protein as disclosed herein might be a non-Ig-binding protein, for example but not limited to, a protein that does not bind to the Fc part of immunoglobulin. In some embodiments, a non-Ig binding protein has at least 89.5% identity to SEQ ID NO: 13 or SEQ ID NO: 14. Accordingly, some embodiments encompass fusion proteins comprising a binding protein for the spike protein or domain thereof as disclosed herein and one or two or three or more non-Ig-binding polypeptide(s). In various embodiments, a non-Ig binding protein has at least 89.5% identity to SEQ ID NO: 13 or SEQ ID NO: 14, and has a D or E, preferably a D, at the position corresponding to position 13 of SEQ ID NO: 13 or 14, and/or has an R, K, or H, preferably R, at the position corresponding to position 31 of SEQ ID NO: 13 or SEQ ID NO: 14. In various embodiments, the non-Ig binding protein has a S at one or more of the positions corresponding to positions 10 and 14 of SEQ ID NO: 13 or 14.

In various embodiments, the non-Ig binding protein may have a Q at the position corresponding to position 10 of SEQ ID NO: 13 or 14, and/or may have a K at the position corresponding to position 14 of SEQ ID NO: 13 or 14. In various embodiments, the non-Ig binding protein may have an I at the position corresponding to position 8 of SEQ ID NO: 13 or 14.

In some embodiments, a fusion protein may comprise the following combinations from N-terminus to C-terminus: (a) at least one binding protein for the spike protein fused to at least one non-Ig binding protein; (b) at least one non-Ig binding protein fused to at least one binding protein for the spike protein; (c) non-Ig binding protein fused to a binding protein for the spike protein fused to a binding non-Ig binding protein; (d) binding protein for the spike protein fused to a dimer of a non-Ig binding protein; (e) dimer of a binding protein for the spike protein fused to a dimer of a non-Ig binding protein; (f) dimer of a non-Ig binding protein fused to a binding protein for the spike protein; (g) non-Ig binding protein fused to a dimer of a binding protein for the spike protein fused to a non-Ig binding protein; (h) binding protein for the spike protein fused to a non-Ig binding protein fused to a binding protein for the spike protein fused to a non-Ig binding protein; (i) monomer or dimer of a binding protein for the spike protein fused to a dimer or tetramer of a non-Ig binding protein, (j) dimeric binding protein fused to a non-Ig binding protein (e.g. monomer, dimer or trimer) fused to a monomer of binding protein; or (k) monomer of a binding protein fused to a non-Ig binding protein (e.g. monomer, dimer or trimer) fused to a dimeric binding protein.

Other combinations of non-Ig binding protein and binding protein for the spike protein are also feasible to someone skilled in the art. A fusion of the binding protein with one, two, three or more non-Ig binding protein(s) may improve expression of the protein and ligand detectability in the Protein A ELISA leaching assay (see Examples).

As further described herein, the non-Ig-binding protein has no detectable binding affinity for the Fc domain of immunoglobulin as determined by SPR spectroscopy, more specifically the BIAcore SPR system. Further, non-Ig-binding protein has no detectable binding affinity for the spike protein (S1, RBD) of SARS CoV-2 or variants, as determined by SPR spectroscopy, more specifically the BIAcore SPR system.

The present invention encompasses fusion proteins comprising a monomer (binding protein) having at least 80% or at least 85% sequence identity to SEQ ID NO: 1 or 65, and at least one non-Ig binding protein having at least 89.5% identity to SEQ ID NO: 13 or SEQ ID NO: 14. In preferred embodiments, the monomer (binding protein) is located at the N-terminus of the fusion protein. In particular, the present invention encompasses fusion proteins comprising a monomer (binding protein) having at least 80% or at least 85% sequence identity to SEQ ID NO: 27 or 28, preferably SEQ ID NO: 28, and at least one non-Ig binding protein having at least 89.5% identity to SEQ ID NO: 13 or SEQ ID NO: 14. In preferred embodiments, the monomer (binding protein) is located at the N-terminus of the fusion protein.

Preferably, the fusion protein has a binding affinity of less than 500 nM, more preferably less than 100 nM, for the spike protein or domains thereof.

In preferred embodiments, the fusion protein comprises a monomer (binding protein) having at least 80% or at least 85% sequence identity to SEQ ID NO: 1 or 65, and one, two, or three non-Ig binding proteins, each having at least 89.5% identity to SEQ ID NO: 13 or SEQ ID NO: 14. In other preferred embodiments, the fusion protein comprises a monomer (binding protein) having at least 80% or at least 85% sequence identity to SEQ ID NO: 27 or 28, preferably SEQ ID NO: 28, and one, two, or three non-Ig binding proteins, each having at least 89.5% identity to SEQ ID NO: 13 or SEQ ID NO: 14. The non-Ig binding proteins may be the same or different in the fusion protein.

In various embodiments of the monomer (binding protein), the amino acids at the positions corresponding to positions 8, 11, 42, 44, 46, 49, and 54 of SEQ ID NO: 1 or 65 are (A or D), (S or A), (K or L), (V or I), (G or A), (Q or K), and/or (S or A), respectively. In preferred embodiments, the amino acids at the positions corresponding to positions 8, 11, 42, 44, 46, 49, and 54 of SEQ ID NO: 1 or 65 are D, A, L, I, A, K, and A, respectively. In further embodiments, the amino acids at positions selected from any of positions 4, 5, 7, 10, 13, 14, 17, 18, 24, 25, 27, 28, 29, 32, 35, and 36 of SEQ ID NO: 1 or 65 are any of 4V, 5L, 7I, 10H, 13T, 14E, 17W, 18W, 24K, 25Q, 27K, 28V, 29W, 32M, 35T, and/or 36Q.

In various other embodiments of the monomer (binding protein), the amino acids at the positions corresponding to positions 6, 9, 40, 42, 44, 47, and 52 of SEQ ID NO: 27 or 28 are (A or D), (S or A), (K or L), (V or I), (G or A), (Q or K), and/or (S or A), respectively. In preferred embodiments, the amino acids at the positions corresponding to positions 6, 9, 40, 42, 44, 47, and 52 of SEQ ID NO: 27 or 28 are D, A, L, I, A, K, and A, respectively. In further embodiments, the amino acids at positions selected from any of positions 2, 3, 5, 8, 11, 12, 15, 16, 22, 23, 25, 26, 27, 30, 33, and 34 of SEQ ID NO: 27 or 28 are any of 2V, 3L, 5I, 8H, 11T, 12E, 15W, 16W, 22K, 23Q, 25K, 26V, 27W, 30M, 33T, and/or 34Q, respectively.

In various embodiments of the fusion protein, the at least one non-Ig binding protein has at least 89.5% identity to SEQ ID NO: 13 or SEQ ID NO: 14. In various embodiments of the fusion protein, the at least one non-Ig binding protein has at least 89.5% identity to SEQ ID NO: 13 or SEQ ID NO: 14 and has a D or E, preferably a D, at the position corresponding to position 13 of SEQ ID NO: 13 or 14, and/or has an R, K, or H, preferably R, at the position corresponding to position 31 of SEQ ID NO: 13 or SEQ ID NO: 14. In various other embodiments, the non-Ig binding protein has a S at one or more of the positions corresponding to positions 10 and 14 of SEQ ID NO: 13 or 14. In various other embodiments, the non-Ig binding protein may have a Q at the position corresponding to position 10 of SEQ ID NO: 13 or 14, and/or may have a K at the position corresponding to position 14 of SEQ ID NO: 13 or 14. In various further embodiments, the non-Ig binding protein may have an I at the position corresponding to position 8 of SEQ ID NO: 13 or 14.

In some embodiments, fusion proteins comprising at least one binding protein for the spike protein and at least one non-Ig binding protein are provided in SEQ ID NO: 29 (212895), SEQ ID NO: 30 (212896), SEQ ID NO: 31 (212897), SEQ ID NO: 32 (213147), SEQ ID NO: 33 (213152), SEQ ID NO: 38, SEQ ID NO: 39, SEQ ID NO. 51-53, and SEQ ID NOs: 68-72.

SEQ ID NO: 29 (212895) is a fusion protein wherein the spike protein binding protein of SEQ ID NO: 1 (212434) is fused to a trimer of non-Ig binding protein according to SEQ ID NO: 14. SEQ ID NO: 31 (212897) is a fusion protein wherein the spike protein binding protein of SEQ ID NO: 1 (dimer of 212434) is fused to a tetramer of non-Ig binding protein according to SEQ ID NO: 14.

SEQ ID NO: 38 is a fusion protein wherein the spike protein binding protein of SEQ ID NO: 28 is fused to a dimer non-Ig binding protein according to SEQ ID NO: 14. SEQ ID NO: 30 (212896) is a fusion protein wherein the spike protein binding protein of SEQ ID NO: 28 is fused to a trimer of non-Ig binding protein according to SEQ ID NO: 14. SEQ ID NO: 39 is a fusion protein wherein the spike protein binding protein of SEQ ID NO: 28 is fused to non-Ig binding protein according to SEQ ID NO: 14 fused to spike protein binding protein of SEQ ID NO: 28 fused to non-Ig binding protein according to SEQ ID NO: 14.

The present invention encompasses fusion proteins comprising a binding protein fused to a non-Ig binding protein according to SEQ ID NO: 13 or SEQ ID NO: 14, wherein the binding protein is a dimer or (homo/hetero-)multimer. In various embodiments, the first (N-terminal) monomer of the dimer or multimer may have at least 80% sequence identity to the sequence of SEQ ID NO: 1 or the sequence of SEQ ID NO: 28. In various embodiments, the second (C-terminal) monomer of the dimer or multimer may have at least 80% sequence identity to the sequence of SEQ ID NO: 1 or the sequence of SEQ ID NO: 28.

In some embodiments, the binding protein for the spike protein or a domain thereof as described above further comprises or is fused to or conjugated to a compound or at least one further polypeptide distinct from the polypeptide as disclosed. In various embodiments, the further compound or polypeptide distinct from the binding protein for the spike protein as disclosed herein might be at least one diagnostically active moiety. In some embodiments, the binding protein for the spike protein (or a domain thereof) is fused to or conjugated to a diagnostically active moiety optionally selected from a radionuclide, fluorescent protein, photosensitizer, dye, or enzyme, or any combination of the above. In some embodiments, a binding protein for the spike protein or a domain thereof that comprises additionally or is fused to or conjugated to at least one diagnostic moiety can be employed, for example, as imaging agent, for example to evaluate presence and distribution of viral particles. Methods for detection or monitoring of viruses may involve imaging methods. Such methods involve imaging SARS-Cov-2 or variants by, for example, radioimaging or photoluminescense or fluorescence. Suitable radionuclides for applications in imaging in vivo or in vitro or for radiotherapy include for example but are not limited to the group of gamma-emitting isotopes, the group of positron emitters, the group of beta-emitters, and the group of alpha-emitters. In some embodiments, suitable conjugation partners include chelators such as 1,4,7,10-tetraazacyclododecane-1,4,7,10-tetraacetic acid (DOTA) or diethylene triamine pentaacetic acid (DTPA) or their activated derivatives, nanoparticles and liposomes. In various embodiments, DOTA may be suitable as complexing agent for radioisotopes and other agents for imaging.

In some embodiments, the binding protein for the spike protein or a domain thereof as described above further comprises at least or is fused to or conjugated to a compound or one further polypeptide distinct from the polypeptide as disclosed. In various embodiments, the further polypeptide distinct from the binding protein for the spike protein as disclosed herein might be at least one therapeutically active moiety. In some embodiments, the binding protein for the spike protein (or a domain thereof) is fused to or conjugated to a therapeutically active moiety optionally selected from a monoclonal antibody or a fragment thereof, a radionuclide, a cytotoxic compound, a cytokine, a chemokine, an enzyme, or derivatives thereof, or any combination of the above. In some embodiments, the binding protein for the spike protein or a domain thereof as described above additionally comprises or is fused to or conjugated to a therapeutically active component and may be used in targeted delivery of any of the above listed components to the spike protein of SARS-Cov-2 or variants.

In some embodiments, the binding protein for the spike protein or a domain thereof as described above further comprises or is fused to or conjugated to a compound or at least one further polypeptide distinct from the polypeptide as disclosed. In various embodiments, the compound or further polypeptide distinct from the binding protein for the spike protein as disclosed herein might be at least one moiety modulating pharmacokinetics. In some embodiments, the binding protein for the spike protein (or a domain thereof) is fused to or conjugated to a moiety modulationg pharmacokinetics optionally selected from a polyethylene glycol, a human serum albumin, an albumin-binding protein or peptide, an immunoglobulin binding protein or peptide, or an immunoglobulin or immunoglobulin fragment, a polysaccharide, or an unstructured amino acid sequence comprising amino acids alanine, glycine, serine, proline.

The moieties, i.e. the binding protein for the spike protein and the moiety modulating pharmacokinetics or diagnostically active moiety or therapeutically active moiety, may be linked to each other directly head-to-tail or may be linked by a linker, wherein the linker preferably is a peptide linker. In various embodiments, a peptide linker may be considered as an amino acid sequence which sterically separates the two portions of the fusion protein. Typically, such linker consists of between 1 and 30 amino acids.

In some embodiments, the binding protein for the spike protein may comprise at least two monomers SEQ ID NO: 1 (or at least 80% identical thereto) linked to each other in head-to-tail orientation via a peptide linker. For example, the binding protein for the spike protein may comprise at least two monomers as shown in SEQ ID NO: 28 (or at least 80% identical thereto) linked to each other in head-to-tail orientation via a peptide linker between two monomers. In some embodiments, the linker may consist of 20 amino acids selected from any amino acid. In some embodiments, the linker may consist of 20 amino acids selected from the group of Q, A, P, K, V, D, F, S.

Molecules for purification or detection. In some embodiments, the binding protein for the spike protein or domains thereof may also comprise additional amino acid residues at the N- and/or C-terminal end, such as for example an additional sequence at the N- and/or C-terminal end. Additional sequences may include for example sequences introduced e.g. for purification or detection. Typical examples for such sequences include, without being limiting, Strep-tags, oligohistidine-tags, glutathione S-transferase, maltose-binding protein, inteins, intein fragments, or the albumin-binding domain of protein G, or others. In one embodiment, additional amino acid sequences include one or more peptide sequences that confer an affinity to certain chromatography column materials. The binding protein for the spike protein or domains thereof may include specific attachment sites for the attachment to solid supports, preferably at the C-terminal end, such as cysteine or lysine.

Method of identification/generation of the binding protein for the spike protein. The present invention further provides a method for the identification/generation of a binding polypeptide for the spike glycoprotein or domains thereof as disclosed herein with binding affinity for the spike protein or domains thereof, the method comprising the following steps: (i) providing a population (library) of proteins; (ii) contacting the population of proteins of (i) with a protein comprising spike protein or a domain thereof; (iii) identifying a complex comprising an binding protein for the spike protein or domain thereof bound to protein comprising spike protein or a domain thereof; and (iv) obtaining an binding protein for the spike protein or domain thereof is capable of binding to protein comprising spike protein or a domain thereof.

The method for the generation of a binding protein for the spike protein or domain thereof may comprise, a further step of determining the binding affinity to a protein comprising spike protein or a domain thereof. The binding affinity may be determined as described elsewhere herein.

Use of the novel binding protein for the spike protein in technical applications. Also provided herein is the use of any novel binding protein for the spike protein as disclosed herein, including multimers, including fusion proteins, in technical applications, preferably for use in affinity purification. This is particularly important in view of purification of vaccines against SARS-Cov-2 or variants.

As described herein, affinity chromatography (also called affinity purification) makes use of specific binding interactions between molecules. Methods for immobilization of protein and methods for affinity chromatography are well-known in the field of protein purification and can be easily performed by a skilled person in this field using standard techniques and equipment.

Further embodiments relate to a process of manufacturing spike protein or domains thereof or a vaccine comprising spike protein or domains thereof comprising at least one chromatographic step employing an affinity chromatography matrix having an affinity for specifically binding spike protein or domains thereof wherein the affinity ligand (binding protein) for spike protein or domains thereof as described above is coupled to said affinity chromatography matrix.

In various embodiments, the method of affinity purification may further comprise one or more washing steps carried out under conditions sufficient to remove from the affinity purification matrix some or all molecules that are non-specifically bound thereto. Affinity purification matrices suitable for the disclosed uses and methods are known to a person skilled in the art.

Conjugation to a solid support. In various aspects and/or embodiments of the present invention, the novel proteins disclosed herein including novel proteins generated or obtained by any of the methods as described above are conjugated to a solid support. In some embodiments of the invention, the polypeptide comprises an attachment site for site-specific covalent coupling of the polypeptide to a solid support. Specific attachment sites comprise without being limited thereto, natural amino acids, such as cysteine or lysine, which enable specific chemical reactions with a reactive group of the solid phase, or a linker between the solid phase and the protein.

Affinity purification matrix. In another embodiment, an affinity purification matrix is provided comprising a binding protein for the spike protein, including a polypeptide identified by any of the methods as described above.

In preferred embodiments, the affinity purification matrix is a solid support. The affinity purification matrix comprises at least one binding protein for the spike protein or domains thereof as described herein. Accordingly, a novel binding protein for the spike protein or domains thereof disclosed herein is encompassed for use in the purification of a protein or particle by an affinity matrix, preferably for use in the purification of a vaccine against SARS-Cov-2 or variants thereof.

Solid support matrices for affinity chromatography are known in the art and include, e.g., without being limited thereto, agarose and stabilized derivatives of agarose, cellulose or derivatives of cellulose, controlled pore glass, monolith, silica, zirconium oxide, titanium oxide, or synthetic polymers, and hydrogels of various compositions and combinations of the above.

The formats for solid support matrices can be of any suitable well-known kind. Such solid support matrix for coupling a novel protein or polypeptide of the present invention might comprise, e.g., one of the following, without being limited thereto: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical beads, for example Sepharose or Agarose beads. Matrices in particle form can be used as a packed bed or in a suspended form including expanded beds. In other embodiments of the invention, the solid support matrix is a membrane, for example a hydrogel membrane. In some embodiments, the affinity purification may involve a membrane as a matrix to which a binding protein for the spike protein of the present invention is covalently bound. The solid support can also be in the form of a membrane in a cartridge.

In some embodiments, the affinity purification involves a chromatography column containing a solid support matrix to which a novel protein of the present invention is covalently bound. A novel protein or polypeptide of the present invention may be attached to a suitable solid support matrix via conventional coupling techniques. Methods for immobilization of protein ligands to solid supports are well-known in the field of protein engineering and purification and can easily be performed by a skilled person in this field using standard techniques and equipment.

Further, in some embodiments, the binding protein for the spike protein as described herein or the fusion protein as described herein are used in methods to determine the presence of a protein comprising spike protein or a domain thereof, for example, a vaccine against SARS-Cov-2. Some embodiments relate to a method of analyzing the presence of protein comprising spike protein or a domain thereof in liquid samples, the method comprising the following steps: (a) providing a liquid that contains a protein or particle comprising spike protein or a domain thereof, (b) providing the binding protein for the spike protein, (c) contacting the liquid that contains protein or particle comprising spike protein or a domain thereof with the binding protein for the spike protein as described herein under conditions that permit binding of the at least one binding protein for the spike protein to protein or particle comprising spike protein or a domain thereof, (d) isolating (eluting) the complex of a protein or particle comprising spike protein or a domain thereof and the binding protein for the spike protein, and optionally, (e) determining the amount of the binding protein for the spike protein which indicates the amount of protein or particle comprising spike protein or a domain thereof in the liquid of (a).

Further embodiments relate to a method of quantification of a protein or particle comprising spike protein or a domain thereof of the spike protein, the method comprising: (a) providing a liquid that contains protein or particle comprising spike protein or a domain thereof; (b) providing a matrix to which the binding protein for the spike protein as described herein has been covalently coupled; (c) contacting said affinity purification matrix with the liquid under conditions that permit binding of the at least one binding protein for the spike protein to protein or particle comprising spike protein or a domain thereof; (d) eluting said protein or particle comprising spike protein or a domain thereof; and optionally, (e) quantitating the amount of eluted protein or particle comprising spike protein or a domain thereof. Methods to determine the presence of protein or particle comprising spike protein or a domain thereof in liquid samples might be quantitative or qualitative. Such methods are well known to the skilled person and can be selected, for instance but limited to, from the following methods that are well established in the art: enzyme-linked immunosorbent assay (ELISA), enzymatic reactions, surface plasmon resonance (SPR) or chromatography.

Use of the binding proteins for spike protein for medical applications. In some embodiments, the binding protein for the spike protein or a domain thereof as described above is used in diagnosis or treatment of SARS-COV-2 (or variants thereof) related diseases. In one embodiment, the binding protein for the spike protein or domains thereof is used in medicine to diagnose of SARS-Cov-2 or variants or treat diseases associated with SARS-Cov-2 or variants. One embodiment is a method of diagnosing (including monitoring), the method of diagnosis (monitoring) comprising administering to the subject the binding protein for the spike protein or domains thereof as described, optionally conjugated to radioactive molecules. In various embodiments, the binding protein for the spike protein or domains thereof as disclosed herein may be used for diagnosis of SARS-Cov-2 or variants, optionally wherein the binding protein for the spike protein or domains thereof is conjugated to a radioactive molecule. In some embodiments, imaging methods using the binding protein for the spike protein or domains thereof with labels such as radioactive or fluorescent can be employed to visualize spike protein or domains thereof on virus cells, for example, to evaluate presence of viral particles, and/or to evaluate the response of a patient to a therapeutic treatment. In some embodiments, the diagnostic methods are in vitro methods for diagnosing the presence of viral particles by using the binding protein for the spike protein (i.e. binding protein for S1 domain and/or RBD and/or mutants thereof) to evaluate the presence of viral particles. Some embodiments relate to the use of the binding protein for the spike protein (i.e. binding protein for S1 domain and/or RBD) for the manufacture of a substance or compound for the diagnosis of diseases related to or caused by SARS-Cov-2 or variants.

One embodiment is a method of treating a subject having diseases related to or caused by SARS-Cov-2 or variants, the method of treatment comprising administering to the subject the spike protein binding protein as described herein. In various embodiments, the binding protein for the spike protein or domains thereof as disclosed herein is for use for treatment of diseases related to or caused by SARS-Cov-2 or variants. Some embodiments relate to the use of the binding protein for the spike protein (i.e. binding protein for S1 domain and/or RBD) for the manufacture of a medicament for the treatment of diseases related to or caused by SARS-Cov-2 or variants.

Compositions. Various embodiments relate to a composition comprising the binding protein for the spike protein or domains thereof as disclosed herein. A composition comprising the binding protein for the spike protein or domains thereof as defined above for use in medicine, preferably for use in the diagnosis (detection/monitoring) of SARS-Cov-2 or treatment of diseases related to or caused by SARS-Cov-2 or variants as described above. Compositions comprising the binding protein for the spike protein or domains thereof as described above may be used for clinical applications for both diagnostic and therapeutic purposes. In particular, compositions comprising the binding protein for the spike protein or domains thereof as described herein may be used for clinical applications for imaging, monitoring, and eliminating or inactivating SARS-Cov-2 or variant.

Various embodiments relate to a diagnostic composition for the diagnosis of SARS-Cov-2 comprising the binding protein for the spike protein or domains thereof as defined herein and a diagnostically acceptable carrier and/or diluent. These include for example but are not limited to stabilizing agents, surface-active agents, salts, buffers, coloring agents etc. The compositions can be in the form of a liquid preparation, a lyophilisate, granules, in the form of an emulsion or a liposomal preparation.

The diagnostic composition comprising the binding protein for the spike protein or domains thereof as described herein can be used for diagnosis of SARS-Cov-2 or variants, as described above. Various embodiments relate to a pharmaceutical (e.g. therapeutic) composition for the treatment of diseases comprising the binding protein for the spike protein or domains thereof as disclosed herein, and a pharmaceutically (e.g. therapeutically) acceptable carrier and/or diluent. The pharmaceutical (e.g. therapeutic) composition optionally may contain further auxiliary agents and excipients known per se. These include for example but are not limited to stabilizing agents, surface-active agents, salts, buffers, coloring agents etc.

The pharmaceutical composition comprising the binding protein for the spike protein or domains thereof as defined herein can be used for treatment of diseases, as described above.

The compositions contain an effective dose of the binding protein for the spike protein or domains thereof as defined herein. The amount of protein to be administered depends on the organism, the type of disease, the age and weight of the patient and further factors known per se. Depending on the galenic preparation these compositions can be administered parentally by injection or infusion, systemically, intraperitoneally, intramuscularly, subcutaneously, transdermally, or by other conventionally employed methods of application.

The composition can be in the form of a liquid preparation, a lyophilisate, a cream, a lotion for topical application, an aerosol, in the form of powders, granules, in the form of an emulsion or a liposomal preparation. The type of preparation depends on the type of disease, the route of administration, the severity of the disease, the patient and other factors known to those skilled in the art of medicine.

The various components of the composition may be packaged as a kit with instructions for use.

Polynucleotides, vectors, host cells. One embodiment covers an isolated polynucleotide or nucleic acid molecule encoding a binding protein for the spike protein as disclosed herein. A further embodiment also encompasses proteins encoded by the polynucleotides as disclosed herein.

Further provided is a vector, in particular an expression vector, comprising the isolated polynucleotide or nucleic acid molecule of the invention, as well as a host cell comprising the isolated polynucleotide or the expression vector. For example, one or more polynucleotides, which encode a polypeptide as disclosed herein may be expressed in a suitable host and the produced protein can be isolated. A vector means any molecule or entity (e.g., nucleic acid, plasmid, bacteriophage or virus) that can be used for transfer of protein-encoding information into a host cell. Suitable vectors that may be applied in the present invention are known in the art.

Furthermore, an isolated cell comprising a polynucleotide or nucleic acid, or a vector as disclosed herein is provided. Suitable host cells include prokaryotes or eukaryotes, for example a bacterial host cell, a yeast host cell or a non-human host cell carrying a vector. Suitable bacterial expression host cells or systems are known in the art. Various mammalian or insect cell culture systems as known in the art can also be employed to express recombinant proteins.

Method of producing a protein of the invention. In a further embodiment, a method for the production of the binding protein for the spike protein or domain thereof as described is provided, the method comprising the step(s): (a) culturing a (suitable) host cell under conditions suitable for the expression of the binding protein for the spike protein or domain thereof so as to obtain said binding protein for the spike protein; and (b) optionally isolating said binding protein for the spike protein or domain thereof. Suitable conditions for culturing a prokaryotic or eukaryotic host are well known to a person skilled in the art.

The binding protein for the spike protein or domain thereof may be prepared by any conventional and well-known techniques such as plain organic synthetic strategies, solid phase-assisted synthesis techniques, or by commercially available automated synthesizers. They may also be prepared by conventional recombinant techniques, alone or in combination with conventional synthetic techniques.

In one embodiment, a method for the preparation of the binding protein for the spike protein or domain thereof is provided, as detailed above, said method comprising the steps: (a) providing a nucleic acid molecule encoding the binding polypeptide; (b) introducing said nucleic acid molecule into an expression vector; (c) introducing said expression vector into a host cell; (d) culturing the host cell in a culture medium; (e) subjecting the host cell to culturing conditions suitable for expression thereby producing a binding polypeptide; optionally (f) isolating the protein or polypeptide produced in step (e); and (g) optionally conjugating the protein or polypeptide to a solid matrix as described above. In various embodiments of the present invention the production of the binding protein for the spike protein is performed by cell-free in vitro transcription and translation.

The following Examples are provided for further illustration of the invention. The invention, however, is not limited thereto, and the following Examples merely show the practicability of the invention on the basis of the above description.

EXAMPLES

The following Examples are provided for further illustration of the invention. The invention, however, is not limited thereto, and the following Examples merely show the practicability of the invention on the basis of the above description. For a complete disclosure of the invention reference is made also to the literature cited in the application which is incorporated completely into the application by reference.

Example 1. Selection and Screening of Binding Protein for the Spike Protein

Validation of the target: The binding of the S1 or RBD subunit of the spike protein to ACE2 was analyzed via SPR (see Example 3 below). Chip: Immobilized ACE2-Avi-His (biotinylated) on SA Chip (~1000 RU); analyte concentration: 100 nM. Both the S1 subunit (S1-His) of the spike protein as well as the receptor binding domain (RBD) of the spike protein bind to immobilized ACE2-receptor.

Libraries. Proprietary cDNA libraries based on stable Protein A like variants (artificial mosaic proteins composed of fragments of Protein A domains and additional mutations; e.g. SEQ ID NO: 15 or SEQ ID NO: 16) were synthesized in house by randomized oligonucleotides generated by synthetic trinucleotide phosphoramidites (ELLA Biotech) to achieve a well-balanced amino acid distribution with simultaneously exclusion of cysteine and other amino acid residues at randomized positions. The corresponding cDNA library was amplified by PCR and ligated into a pCD33-OmpA phagemid. Aliquots of the ligation mixture were used for electroporation of *E. coli* SS320 (Lucigen) to produce and purify the phage library to store them as cryo-stocks. Unless otherwise indicated, established recombinant genetic methods were used.

Native libraries were enriched against the respective ON-target (S1-His or RBD-Fc) using phage display as selection system. In each round a pre-selection step was performed using either empty Sigmablocker-blocked beads or hIgG1-Fc as OFF-target. The AIT-method was applied, which means that the target proteins were immobilized to magnetic Epoxy M-270 Dynabeads or magnetic Protein A/G Dynabeads before each round started. *E. coli* ER2738 (Lucigene) were used for infection with cryo phage libraries and for reamplification of phage pools after each round. Amplification and purification of the phages were carried out using standard methods known to a skilled person. All four selection rounds were performed with the automated KingFisher-System (Thermo Fisher) to isolate and capture the desired phage-target complexes. Bound phages were eluted by trypsin and reamplified. The success of the selection was analyzed by phage-pool-ELISA in medium binding microtiter plates (Greiner Bio-One) coated with S1-His (2.3 μg/ml), RBD-Fc (2.3 μg/ml), hIgG1-Fc (2.3 μg/ml) or Sigmablocker. Bound phages were detected using α-M13 HRP conjugated antibody (GE Healthcare).

Cloning of target binding phage pools into an expression vector. Selection pools showing specific binding to S1-His and/or RBD-Fc in phage pool ELISA were amplified by PCR according to methods known in the art, cut with appropriate restriction nucleases and ligated into a derivative of the expression vector pET-28a (Merck, Germany) comprising an N-terminal GFP-His-tag followed by an enzymatic cleavage site and a C-terminal cysteine.

Results: Various phage display selection pools resulted in specific signals for the respective ON-targets S1-His and RBD-Fc (see FIG. 2A). Controls with hIgG1-Fc and Sigmablocker showed for most of the pools no unspecific binding. Selected pools were sequenced, subcloned and proceed to high throughput screening. 12 enriched variants were selected as direct transfer for lab-scale production and purification.

Primary screening: Selection pools were therefore proceeded to high throughput primary screening. Positive control: sfGFP-10xHis-cs5 (Ig binding protein), negative control: sfGFP-10×His. Detection: fluorescence signal (ex 485 nm/em 535 nm). 5671 variants were selected for secondary screening (on target: S1-His (c=2.5 μg/ml); off target: BSA). Hit criteria: signal of sample larger than signal of negative control. 177 hits were identified for further analysis. Secondary screening. 177 hits were sequenced, produced in μ-scale (Phynexus) (see Example 2) and analyzed by BLI. The proteins were immobilized on a Ni-NTA sensor (ForteBio). Upon binding, target analyte was accumulated on the surface increasing the refractive index. This change in the refractive index was measured in real time and plotted as nm shift versus time.

Example 2. Expression and Purification of SARS-Cov2 Binding Proteins

Variants with SARS Cov2 S1 binding were expressed in *Escherichia coli* BL21(DE3) using a pNP-013 vector system under regulation of a T7 promoter. Proteins were produced in soluble form after induction by lactose included in the medium (autoinduction medium). BL21 (DE3) competent cells were transformed with the expression plasmid, spread onto selective agar plates (kanamycin) and incubated over night at 37° C. Precultures were inoculated from single colony in 3 ml 2×YT medium supplemented with 50 μg/ml kanamycin and cultured for 6 h at 37° C. at 210 rpm in a conventional orbital shaker in culture tubes. For main cultures 350 mL ZYM-5052 medium (see Studier 2004) were inoculated with entire precultures and incubated in 2.5 L Ultra Yield™ flasks at 30° C. at 180 rpm in an orbital shaker. The culture medium was supplemented with 50 μg/ml kanamycin and antifoam SE15. Recombinant protein expression was induced by metabolizing glucose and subsequently allowing lactose to enter the cells. Cells were grown over night for approximately 18 hours to reach a final OD600 of about 10-20. Before the harvest, the OD600 was measured, samples adjusted to 0.6/OD600 were withdrawn, pelleted and frozen at −20° C. To collect biomass cells were centrifuged at 12000×g for 20 min at 22° C. Pellets were weighed (wet weight) and stored at −20° C. before processing.

Fusion proteins were expressed by *E. coli* BL21(DE3) through fermentation using a tag-free proprietary pET-based vector system (e.g. referred to as pNP-004, featuring a c-terminal cysteine, or referred to as pNP-013, featuring an N-terminal superfolder-GFP-10xHis-TVMV and C-terminal cysteine). Precultures were generated in two steps. For a first preculture, 50 mL preculture medium (34.5 g/L yeast extract, 0.61 g/L $MgSO_4$, 14.2 $K_2HPO_4$, 0.5 g/L NH4Cl, 20 g/L glucose, 50 μg/mL kanamycin) was inoculated from a single colony and incubated for 16-18 h at 37° C. and 210 rpm in a shake flask. The seed culture (second preculture) was inoculated to an OD600 of 0.1 and grown for 6 h at 37° C. and 210 rpm in 1 L baffled shake flasks with 200 mL of preculture medium. The fermentation process was performed in a bench-top bioreactor as a fed-batch process. In the batch phase (37° C., pH 7.1, 30% $pO_2$ saturation, aeration 2 VVM), the culture medium (17.25 g/L yeast extract, 0.61 g/L $MgSO_4$, 14.2 $K_2HPO_4$, 0.5 g/L $NH_4Cl$, 50 μg/mL kanamycin) was inoculated to an OD600 of 0.3 and the culture was incubated until substrate was depleted ($pO_2$ spike). The pH value was maintained by automatic addition of potassium hydroxide (20% (w/v)) and phosphoric acid (10% (v/v)). Afterwards, the feeding phase was performed for 11 h (exponential growth, p=0.11 1/h) with glucose as the main substrate (200 g/L glucose, 276 g/L yeast extract, 50 μg/mL kanamycin). Protein expression was induced by isopropyl β-D-1-thiogalactopyranoside (IPTG, end concentration of 1 mM) at 30° C. for 5 h at a constant feeding rate (value as after 11 h of exponential feeding). Harvest was performed as described in the previous process.

Proteins were purified by affinity chromatography, protease cleavage and size exclusion. The initial capturing step was performed using IMAC (HisTrap HP 5 ml, GE Healthcare, binding buffer: 50 mM $NaH_2PO_4$, 500 mM NaCl, 30 mM Imidazole, 1 mM DTT pH 7.2; elution buffer: 50 mM $NaH_2PO_4$, 500 mM NaCl, 30 mM Imidazole, 1 mM DTT pH 7.2) followed by a desalting (HiPrep Desalting 53 ml, GE Healthcare) in 50 mM $NaH_2PO_4$, 150 mM NaCl, 10 mM Imidazole, 1 mM DTT pH 7.2 using an ÄKTA xpress system. The collected fractions with protein of interest were incubated with TVMV protease (1 μg TVMV to 100 μg protein) over night at room temperature.

The protein of interest were further purified using IMAC (HisTrap HP 5 ml, GE Healthcare, binding buffer: 50 mM $NaH_2PO_4$, 500 mM NaCl, 10 mM Imidazole, 1 mM DTT pH 7.2; elution buffer: 50 mM $NaH_2PO_4$, 500 mM NaCl, 500 mM Imidazole, 1 mM DTT pH 7.2) in flow-through mode. TVMV protease and cleavage products were captured by the IMAC using an ÄKTA xpress system. The flow-through was collected and polished by size exclusion chromatography using a Superdex 75 26/600 column (GE Healthcare; buffer: 20 mM citric acid, 150 mM NaCl, 1 mM EDTA pH 6) carried out on an ÄKTA avant system (GE Healthcare). Variants without affinity tag (212895, 212896 and 212897) were captured via Q-Sepharose (GE Healthcare, binding buffer: 20 mM TRIS, 1 mM DTT, 1 mM EDTA pH 8.5; elution buffer: 20 mM TRIS, 1 mM DTT, 1 mM EDTA, 1M NaCl, pH 8.5) followed by Phenyl-HP-Sepharose (GE Healthcare, binding buffer: 20 mM TRIS, 1 mM EDTA, 1 mM DTT, 1M $(NH_4)_2SO_4$, pH 8.5; elution buffer: 20 mM TRIS, 1 mM EDTA, 1 mM DTT, pH 8.5) (Fusion proteins 213147 and 213152 were purified by hlgG-Sepharose Q according to manufactures instructions. Polishing was performed by size exclusion chromatography using a Superdex 75 or 200 26/600 column (GE Healthcare; buffer: 20 mM citric acid, 150 mM NaCl, 1 mM EDTA pH 6) carried out on an ÄKTA avant system (GE Healthcare). Following SDS-PAGE analysis positive fractions were pooled and the protein concentrations were determined by absorbance measurement at 280 nm using the molar absorbent coefficient. Further analysis included RP-HPLC and SE-HPLC. Reversed phase chromatography (RP-HPLC) has been performed using a Dionex HPLC system and a PLRP-S (5 μm, 300 Å) column (Agilent). Analytic size exclusion chromatography (SE-HPLC) has been performed using a Dionex HPLC system and a Superdex75 increase 5/150 GL (GE Healthcare).

TABLE 1A

Analytic results of spike protein binding proteins

| SEQ ID NO: | CID | SE-HPLC monomer | rp-HPLC main peak | YieldPerVolume yield per L | YieldPerWeight yield per g | solubility soluble expression |
|---|---|---|---|---|---|---|
| 9 | 213103 | 100% | 82.16% | 7.54 mg/L | 0.32 mg/g | 60% |
| 18 | 212728 | 100% | 61.33% | 3.66 mg/L | 0.18 mg/g | 50% |
| 19 | 212522 | 100% | 91.49% | 9.59 mg/L | 0.47 mg/g | 90% |
| 1 | 212434 | 100% | 97.82% | 49.29 mg/L | 1.29 mg/g | 80% |
| 7 | 212361 | 100% | 81.95% | 4.76 mg/L | 0.24 mg/g | 70% |
| 8 | 212335 | 100% | 80.74% | 1.54 mg/L | 80 mg/g | 60% |
| 17 | 212860 | 100% | 83.87% | 4.56 mg/L | 0.19 mg/g | 60% |

TABLE 1B

Analytic results of spike protein binding proteins

| SEQ ID NO: | CID | SE-HPLC Monomer | rp-HPLC main peak | solubility Soluble expression |
|---|---|---|---|---|
| 29 | 212895 | 94.8% | 97.2% | 100% |
| 30 | 212896 | 86.6% | 65.5% | 100% |
| 31 | 212897 | 100% | 93.7% | 100% |
| 32 | 213147 | 100% | 91.5% | 100% |
| 33 | 212152 | 91.3% | 100% | 60% |

Example 3. Binding Analysis of Proteins by SPR

The purified proteins were immobilized on a CM-5 sensor chip (GE Healthcare) using PDEA after NHS/EDC activation resulting in 110-140 RU with a Biacore 3000 system (GE Healthcare). The chip was equilibrated with SPR running buffer (PBS 0.05% Tween pH 7.3).

Upon binding, target analyte was accumulated on the surface increasing the refractive index. This change in the refractive index was measured in real time and plotted as response or resonance units versus time. The analytes (for example, SARS-CoV2 S1 protein or SARS-CoV2 RBD or SARS-CoV-1 or MERS or mutant proteins) were applied to the chip in serial dilutions with a flow rate of 30 μl/min. The association was performed for 120 seconds and the dissociation for 120 seconds. After each run, the chip surface was regenerated with 30 μl regeneration buffer (10 mM glycine pH 2.0) and equilibrated with running buffer.

Binding studies were carried out by the use of the BIAcore 3000 (GE Healthcare); data evaluation was operated via the BIAevaluation 3.0 software, provided by the manufacturer, by the use of the Langmuir 1:1 model (RI=0). Evaluated dissociation constants ($K_D$) were standardized against the immobilized protein and indicated. Shown is the change in refractive index measured in real time and plotted as response or resonance unit [RU] versus time [sec]. Results are shown in Table 2 and FIG. 3. Bindung affinity of fusion proteins comprising binding protein 212434 (SEQ ID NO: 1) or SEQ ID NO: 28 was determined, for example for 212895 (SEQ ID NO: 29), 212896 (SEQ ID NO: 30), 212897 (SEQ ID NO: 31). The off rate of the fusion proteins for RBD was about 3fold faster than for the spike protein binding protein 212434 (SEQ ID NO: 1). The off-rate of the fusion proteins for S1 was about 2-3fold faster. The on-rate of the fusion proteins for S1 was 10fold lower than 212434 (note: on rate is concentration dependent). The binding to full length S-protein was comparable or better than the binding affinity of 212434 (SEQ ID NO: 1).

Ligand 212434 (SEQ ID NO: 1) showed binding affinity to mutant of SARS CoV-2 S protein (69del, 70del, Y144del, N501Y, A570D, D614G, P681H, T7161, S982A, D1118H) (corresponding to B.1.1.7). The fusion protein with SEQ ID NO: 30 (212896; based on SEQ ID NO: 28) showed binding affinity to SARS-CoV-2 S protein RBD (E484Q, L452R) (corresponding to B.1.617.1). SEQ ID NO: 15 (cs27), SEQ ID NO: 16 (C27), and the non-Ig binding protein have no detectable binding affinity for S1 or RBD or variants of S1 or RBD.

TABLE 2

Binding affinity of binding proteins for spike protein and of fusion proteins comprising spike protein binding proteins

| | CID | SPR KD_S1 | SPR KD_RBD |
|---|---|---|---|
| SEQ ID NO: | | | |
| 1 | 212434 | 3.8 nM | 10.2 nM |
| 7 | 212361 | 31 nM | 21.3 nM |
| 8 | 212335 | 13 nM | 68.8 nM |
| 9 | 213103 | 8 nM | n.d. |
| 17 | 212860 | 15 nM | n.d. |
| 18 | 212728 | 6.5 nM | n.d. |
| 19 | 212522 | 24.1 nM | 27.1 nM |
| fusion proteins | | | |
| 29 | 212895 | 560 nM | 34.7 nM |
| 30 | 212896 | 113 nM | 27.6 nM |
| 31 | 212897 | 233 nM | 39.4 nM |
| 32 | 213147 | 225 nM | 42.9 nM |
| 33 | 212152 | 112 nM | 29.3 nM |

Example 4. Affinity Purification of a Protein Comprising Spike Protein or a Domain thereof

TABLE 3

Dimers and fusion proteins comprising binding proteins for spike protein

| monomer 1 SEQ ID NO: | monomer 2 SEQ ID NO: | dimer SEQ ID NO: | dimer CID | comprised in fusion protein |
|---|---|---|---|---|
| 2 | 23 | 17 | 212860 | |
| 26 | 3 | 9 | 213103 | 213147 (SEQ ID NO: 32) |
| 33 | 3 | 36 | 212880 | |
| 21 | 22 | 18 | 212728 | 213152 (SEQ ID NO: 33) |
| 24 | 25 | 19 | 212522 | |
| 1 | 1 | | | 212897 (SEQ ID NO: 31) |
| 28 | 28 | | | 212896 (SEQ ID NO: 30) |

5 Coupling parameter. Fusion proteins comprising SEQ ID NO: 1 (212895, 212897) or SEQ ID NO: 28 (212896) were purified to homogeneity and coupled for AIC experiments. Inhouse expressed target from Expi293 cells was used as target. Purified fusion proteins comprising the binding protein for the spike protein (212895, 212896, 212897, 213147, 213152) were immobilized at 30 mg per mL activated Praesto™ Epoxy 85 (Purolite) according to the manufacturer's instructions, coupling conditions: 35° C. for 3 h, pH 9.5, 110 mg $Na_2SO_4$ per mL Resin. Results: All variants were successfully coupled to epoxy-activated Praesto 85 resin. AIC experiments (Elution profile). For elution pH determination, resins were packed into superformance column housing (Götec, 5-50) and equilibrated in 1×PBS, pH 7.3. Resin was loaded with 1 mg of SARS-Cov2-RBD-His expressed in Expi293-F cell culture supernatant. Elution was performed with a gradient from pH 6.0 to pH 2.0 in 15 column volumes (CV) using a 100 mM citric acid buffer. The pH of buffer fractions containing the target was determined. The pH of the main fraction is listed in TABLE 4. The chromatogram of elution pH determination of 212895 is shown in FIG. 4.

TABLE 4

Determined elution pH at main fraction

| SEQ ID NO: | CID | Elution pH |
|---|---|---|
| 7 | 212361 | >6.0 |
| 8 | 212335 | >6.0 |
| 29 | 212895 | 3.47 |
| 30 | 212896 | 3.4 |
| 31 | 212897 | 3.4 |
| 32 | 213147 | 4.62 |
| 33 | 212152 | 4.19 |

All fusion proteins comprising binding protein SEQ ID NO: 1 (212895, 212897) or binding protein SEQ ID NO: 28 (212896) showed homogenous elution profile with a singular peak. The peak maximum was at pH 3.4 in a pH gradient profile. 96% of captured RBD eluted at pH 3.4. For 213147 (SEQ ID NO: 32; comprises the dimer of 212728/SEQ ID NO: 18), the peak maximum was at about pH 4.3 in a pH gradient profile. The eluted RDB-His target showed high purity. For 213152 (SEQ ID NO: 33; comprises the dimer of 213103/SEQ ID NO: 9), the peak maximum was at about pH 3.9 in a pH gradient profile. The eluted RDB-His target showed high purity.

DBC 10%/Elution. The resin with immobilized fusion protein 212896 comprising binding protein SEQ ID NO: 28 was equilibrated in 1×PBS, pH 7.3. Expressed SARS-Cov2-RBD-His in cell culture supernatant was applied on column until 100% target breakthrough. The bound protein was eluted at 100 mM citric acid buffer pH 3.4 in a single step. The static binding capacity (SBC) was determined by the mass eluted protein calculate by UV280 nm absorption and the extinction coefficient of the target. in 20 mM $Na_2HPO_4$, 150 mM NaCl, pH 6.5 or 1×PBS, pH 7.3 at 10% breakthrough at 6 min residence time.

The 51 domain was eluted with 100 mM acetic acid, 150 mM NaCl, 10% (v/v) propylene glycole, pH 4.0, followed by 100 mM citrate acid, pH 2.0 or with 100 mM acetic acid pH 4.0, followed by 100 mM citrate acid, pH 2.0. Results: static binding capacity was about 10.7 mg/ml. The chromatogram is shown in FIG. 5. The flow through fractions and eluted fraction were analysed by SDS-PAGE shown in FIG. 6.

Caustic stability. The fusion protein 212896 comprising binding protein SEQ ID NO: 28 was coupled to Praesto™ Epoxy 85 as described above and treated with 0.1 M NaOH for at least 10 h at RT. The remaining RBD binding capacity was 87% (equals 40 CIP cycles).

Purity of eluted fraction. 10 μg of neutralized eluted fraction from Praesto85_212896 (comprising monomer of SEQ ID NO: 28), SARS-CoV2-RBD was used as sample. Column: Superdex 200 increased, Tricorn 5/150. Running buffer: 1×PBS, pH 7.3. Results: The purity of the eluted fraction from Praesto-Expoxy 85_212896 was as high as at least 94% after a single chromatography step. The eluted fraction shows high homogeneity after the first purification step from cell culture supernatant (size exclusion chromatography).

Target characterization after elution (RBD) by SDS-PAGE. 2, 1, and 0.5 µg of neutralized eluted fraction from Praesto 85_212896, SARS CoV2 was used as sample. Gel-System: NuPAGE system (Invitrogen), 4-12% Bis-Tris-Gel. Staining: Coomassie Blue R250. Densitometric evaluation software: TotalLab 1D. No impurities after AIC were detectable in SDS-AGE (FIG. 7)

Target characterization after elution (RBD) by binding analysis (SPR). Sample: 100 mM of neutralized eluted fraction from Praesto 85_212896 (comprising monomer of SEQ ID NO: 28), SARS CoV2 was used as sample and analyzed for ACE2 binding. Senor surface: immobilized Protein A (CM5 Chip). Target: human ACE2-Fc (Acro Biosystems, Cat. No.: AC-H5257). Results: The eluted fraction of RBD-His showed binding to human ACE2 receptor. The qualitative binding was confirmed.

Further, sample neutralized eluted fraction from Praesto 85_212896, SARS CoV2 was analyzed for ACE2 binding, after capturing from cell culture supernatant and acid elution at pH 3.4. Senor surface: immobilized Protein A (SPR, CM5 Chip). Target: human ACE2-Fc (Acro Biosystems, Cat. No.: AC-H5257), purified SARS-Cov2-RBD-His was as standard reference. Results: The eluted fraction of RBD-His showed comparable binding to human ACE2 receptor and to purified target. The purification of SARS Cov2-RBD via Praesto_212896 has no negative influence on target binding activity. The SPR-Binding profile is shown in FIG. 8.

Example 5. Ligand Detection in Protein A ELISA (Leaching Assay)

To determine low levels of leached variants in affinity chromatography is important for obtaining reliable results. Protein A ELISA Kits for the detection of native and recombinant Protein A (Repligen, Cat. No. 9000-1) were used for leaching assays according to manufacturer's instructions, except using 0.1% PBST as dilution buffer. Samples: 212896 (comprising monomer of SEQ ID NO: 28), 213147 (comprising monomers of SEQ ID NO: 26 and SEQ ID NO: 3), 213152 (comprising monomers of SEQ NO: 21 and SEQ ID NO: 22), concentration 1.6 ng/ml. All variants showed good detectability in PBST buffer, comparable to rProtein A standard. The detection signal of described variants is illustrated in FIG. 9.

Example 6. Inhibition of ACE2 Binding

Spike protein binding proteins were immobilized on a CM-5 sensor chip (GE Healthcare) using NHS/EDC after PDEA activation as described above (Example 3). An equimolar mixture of S1-His and ACE2 or RBD-His and ACE2 was incubated for 1 h at RT. The mixture was applied to the chip and the binding of spike protein binding proteins analyzed. The binding signal is reduced upon binding to the same epitope. FIG. 3 shows the competitive binding study for 212434 (SEQ ID NO: 1). The spike protein binding protein 212434 binds to the same or an overlapping epitope for S1 or RBD and ACE. Further, fusion protein of SEQ ID NO: 30 binds to the same or an overlapping epitope for S1 or RBD and ACE.

The invention claimed is:

1. A binding protein for the spike protein of severe acute respiratory syndrome corona virus 2 (SARS-Cov-2) comprising any one of SEQ ID NOs: 1, 27, 28, and 65, wherein the binding protein has a binding affinity of less than 500 nM for the spike protein or domains thereof.

2. The binding protein for the spike protein according to claim 1, wherein the binding protein has a binding affinity of less than 500 nM for the S1 domain of the spike protein.

3. The binding protein for the spike protein according to claim 1, wherein 2, 3, 4, 5, or 6 binding proteins for the spike protein comprising any one of SEQ ID NOs: 27, 28, and 65 are linked to each other.

4. The binding protein for the spike protein according to claim 3, wherein the binding protein is a homo-multimer or a hetero-multimer.

5. The binding protein for the spike protein according to claim 4, wherein the binding protein comprises SEQ ID NO: 63 or SEQ ID NO: 64.

6. The binding protein for the spike protein according to claim 1, wherein the binding protein is fused to or conjugated to at least one additional molecule selected from the group consisting of a non-Immunoglobulin-binding protein, a diagnostically active moiety, and a therapeutically active moiety.

7. An affinity separation matrix comprising a binding protein for the spike protein according to claim 1.

8. A method of affinity purification of spike protein or a domain thereof or of a particle comprising spike protein or a domain thereof, optionally a virus particle, the method comprising:

(a) providing a liquid that contains a spike protein or a domain thereof (e.g. a particle comprising spike protein or domain);

(b) providing an affinity separation matrix comprising at least one binding protein for spike protein or a domain thereof according to claim 1 coupled to said affinity separation matrix;

(c) contacting said affinity separation matrix with the liquid under conditions that permit binding of the at least one binding protein for spike protein or a domain thereof according to claim 1; and (d) eluting said spike protein or a domain thereof or particle comprising the spike protein or domain thereof from said affinity purification matrix.

9. A method for analyzing the presence of spike protein or a domain thereof or particle comprising a spike protein or domain thereof in liquid samples, the method comprising:

(i) providing a liquid that contains spike protein or a domain thereof or particle comprising a spike protein or domain, (ii) providing the binding protein for the spike protein according to claim 1, (iii) contacting the liquid of (i) with the binding protein for the spike protein or a domain thereof according to according to claim 1 under conditions that permit binding of the binding protein to the spike protein or a domain thereof, (iv) isolating the complex of spike protein or a domain thereof or particle and the binding protein for the spike protein or a domain thereof according to claim 1, and (v) determining the amount of the binding protein for the spike protein according to claim 1 in the liquid of (i).

10. A polynucleotide encoding the binding protein according to claim 1.

11. The binding protein for the spike protein according to claim 2, wherein the binding protein has a binding affinity of less than 100 nM for the S1 domain of the spike protein.

12. The binding protein for the spike protein according to claim 2, wherein the binding protein has a binding affinity of less than 500 nM for the receptor binding domain (RBD) of the spike protein.

13. The binding protein for the spike protein according to claim 12, wherein the binding protein has a binding affinity of less than 100 nM for the receptor binding domain (RBD) of the spike protein.

14. The binding protein for the spike protein according to claim 6, wherein:

the diagnostically active moiety comprises a radionuclide, fluorescent protein, photosensitizer, dye, or enzyme, or any combination thereof; and/or the therapeutically active moiety comprises a monoclonal antibody or fragment thereof, a binding protein, a receptor or receptor domain, a receptor binding ligand or antagonist, a radionuclide, a cytotoxic compound, a cytokine, a chemokine, an enzyme, or any combination thereof.

15. The binding protein for the spike protein according to claim 14, wherein the non-Immunoglobulin binding protein comprises SEQ ID NO: 14.

16. The binding protein for the spike protein according to claim 4, wherein the binding protein comprises SEQ ID NO: 27 or SEQ ID NO: 28 fused to one, two, or three copies of SEQ ID NO: 14.

17. The binding protein for the spike protein according to claim 16, wherein the binding protein is a hetero-multimer comprising an amino acid sequence selected from the group consisting of SEQ ID NOs: 29-31, 38, and 39.

18. The binding protein for the spike protein according to claim 17, wherein the binding protein comprises SEQ ID NO: 30.

19. The binding protein for the spike protein according to claim 1, wherein the binding protein includes an alanine (A) or aspartic acid (D) at the amino acid position corresponding to amino acid 8 of SEQ ID NO: 65, an alanine (a) or serine (S) at the amino acid position corresponding to amino acid 11 of SEQ ID NO: 65, a lysine (K) or leucine (L) at the amino acid position corresponding to amino acid 42 of SEQ ID NO: 65, a valine (V) or isoleucine (I) at the amino acid position corresponding to amino acid 44 of SEQ ID NO: 65, an alanine (A) or glycine (G) at the amino acid position corresponding to amino acid 46 of SEQ ID NO: 65, a glutamine (Q) or lysine (K) at the amino acid position corresponding to amino acid 49 of SEQ ID NO: 65, an alanine (A) or serine (S) at the amino acid position corresponding to amino acid 54 of SEQ ID NO: 65, or any combination thereof.

* * * * *

SEQUENCE LISTING

```
<160> NUMBER OF SEQ ID NOS: 72

<210> SEQ ID NO 1
<211> LENGTH: 58
<212> TYPE: PRT
<213> ORGANISM: Artificial Sequence
<220> FEATURE:
<223> OTHER INFORMATION: Artificially synthesized spike protein binding
      protein 212434

<400> SEQUENCE: 1

Asn Ala Ala Val Leu Asp Ile Ala Gln His Ser Ala Thr Glu Glu Ile
1               5                   10                  15

Trp Trp Leu Pro Asn Leu Thr Lys Gln Gln Lys Val Trp Phe Ile Met
            20                  25                  30

Ser Leu Thr Gln Asp Pro Ser Val Ser Lys Glu Val Leu Gly Glu Ala
        35                  40                  45

Gln Lys Leu Asn Asp Ser Gln Ala Pro Lys
    50                  55


<210> SEQ ID NO 2
<211> LENGTH: 58
<212> TYPE: PRT
<213> ORGANISM: Artificial Sequence
<220> FEATURE:
<223> OTHER INFORMATION: Artificially synthesized spike protein binding
      protein

<400> SEQUENCE: 2

Ile Ala Ala Lys Phe Asp Glu Ala Gln Gln Tyr Ala Phe Tyr Lys Ile
1               5                   10                  15
```

```
Leu His Leu Trp Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Arg Lys Leu Asn Thr Ser Gln Ala Pro Lys
    50                  55


<210> SEQ ID NO 3
<211> LENGTH: 58
<212> TYPE: PRT
<213> ORGANISM: Artificial Sequence
<220> FEATURE:
<223> OTHER INFORMATION: Artificially synthesized spike protein binding
      protein

<400> SEQUENCE: 3

Ile Ala Ala Lys Phe Asp Glu Ala Gln Leu Ala Ala Phe Gln Glu Ile
1               5                   10                  15

Arg His Leu Pro Asn Leu Thr Glu Glu Gln Arg Glu Ala Phe Ile Thr
            20                  25                  30

Ser Leu Tyr Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 4
<211> LENGTH: 58
<212> TYPE: PRT
<213> ORGANISM: Artificial Sequence
<220> FEATURE:
<223> OTHER INFORMATION: Artificially synthesized spike protein binding
      protein
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid

<400> SEQUENCE: 4

Ile Ala Ala Lys Phe Asp Glu Ala Gln Tyr Ala Ala Phe Leu Glu Ile
1               5                   10                  15

Xaa His Leu Pro Asn Leu Thr Glu Glu Gln Arg Xaa Ala Phe Ile Xaa
            20                  25                  30

Ser Leu Xaa Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 5
<211> LENGTH: 58
<212> TYPE: PRT
<213> ORGANISM: Artificial Sequence
<220> FEATURE:
<223> OTHER INFORMATION: Artificially synthesized spike protein binding
      protein
```

```
<400> SEQUENCE: 5

Ile Ala Ala Lys Phe Asp Glu Ala Gln Tyr Ala Ala Phe Leu Glu Ile
1               5                   10                  15

Val His Leu Pro Asn Leu Thr Glu Glu Gln Arg Gln Ala Phe Ile Ala
            20                  25                  30

Ser Leu Trp Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 6
<211> LENGTH: 58
<212> TYPE: PRT
<213> ORGANISM: Artificial Sequence
<220> FEATURE:
<223> OTHER INFORMATION: Artificially synthesized spike protein binding
      protein

<400> SEQUENCE: 6

Ile Ala Ala Lys Phe Asp Glu Ala Gln Tyr Ala Ala Phe Leu Glu Ile
1               5                   10                  15

His His Leu Pro Asn Leu Thr Glu Glu Gln Arg His Ala Phe Ile Leu
            20                  25                  30

Ser Leu Tyr Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 7
<211> LENGTH: 116
<212> TYPE: PRT
<213> ORGANISM: Artificial Sequence
<220> FEATURE:
<223> OTHER INFORMATION: Artificially synthesized spike protein binding
      protein 212361

<400> SEQUENCE: 7

Ile Ala Ala Lys Phe Asp Glu Ala Gln Gln Tyr Ala Phe Tyr Lys Ile
1               5                   10                  15

Leu His Leu Trp Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Arg Lys Leu Asn Thr Ser Gln Ala Pro Lys Ile Ala Ala Lys Phe Asp
    50                  55                  60

Glu Ala Gln Tyr Ala Ala Phe Leu Glu Ile Val His Leu Pro Asn Leu
65                  70                  75                  80

Thr Glu Glu Gln Arg Gln Ala Phe Ile Ala Ser Leu Trp Asp Asp Pro
                85                  90                  95

Ser Val Ser Leu Glu Val Leu Gly Glu Ala Gln Lys Leu Asn Asp Ser
            100                 105                 110

Gln Ala Pro Lys
        115


<210> SEQ ID NO 8
<211> LENGTH: 116
<212> TYPE: PRT
<213> ORGANISM: Artificial Sequence
<220> FEATURE:
```

<223> OTHER INFORMATION: Artificially synthesized spike protein binding
protein 212335

<400> SEQUENCE: 8

Ile Ala Ala Lys Phe Asp Glu Ala Gln Gln Tyr Ala Phe Tyr Lys Ile
1 5 10 15

Leu His Leu Trp Asn Leu Thr Glu Glu Gln Arg Asn Ala Phe Ile Gln
20 25 30

Ser Leu Arg Asp Asp Pro Ser Val Ser Leu Glu Val Leu Gly Glu Ala
35 40 45

Arg Lys Leu Asn Thr Ser Gln Ala Pro Lys Ile Ala Ala Lys Phe Asp
50 55 60

Glu Ala Gln Tyr Ala Ala Phe Leu Glu Ile His His Leu Pro Asn Leu
65 70 75 80

Thr Glu Glu Gln Arg His Ala Phe Ile Leu Ser Leu Tyr Asp Asp Pro
85 90 95

Ser Val Ser Leu Glu Val Leu Gly Glu Ala Gln Lys Leu Asn Asp Ser
100 105 110

Gln Ala Pro Lys
115

<210> SEQ ID NO 9
<211> LENGTH: 116
<212> TYPE: PRT
<213> ORGANISM: Artificial Sequence
<220> FEATURE:
<223> OTHER INFORMATION: Artificially synthesized spike protein binding
protein 213103

<400> SEQUENCE: 9

Ile Ala Ala Lys Phe Asp Glu Ala Gln Gln Trp Ala Phe Tyr Glu Ile
1 5 10 15

Leu His Leu Glu Asn Leu Thr Glu Glu Gln Arg Asn Ala Phe Ile Gln
20 25 30

Ser Leu Arg Asp Asp Pro Ser Val Ser Arg Glu Val Leu Gly Glu Ala
35 40 45

Thr Lys Leu Asn Thr Ser Gln Ala Pro Lys Ile Ala Ala Lys Phe Asp
50 55 60

Glu Ala Gln Leu Ala Ala Phe Gln Glu Ile Arg His Leu Pro Asn Leu
65 70 75 80

Thr Glu Glu Gln Arg Glu Ala Phe Ile Thr Ser Leu Tyr Asp Asp Pro
85 90 95

Ser Val Ser Leu Glu Val Leu Gly Glu Ala Gln Lys Leu Asn Asp Ser
100 105 110

Gln Ala Pro Lys
115

<210> SEQ ID NO 10
<211> LENGTH: 1273
<212> TYPE: PRT
<213> ORGANISM: Artificial Sequence
<220> FEATURE:
<223> OTHER INFORMATION: Artificially synthesized spike glycoprotein S

<400> SEQUENCE: 10

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

-continued

```
Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445
```

```
Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
```

```
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                1020

Leu Ala  Ala Thr Lys Met Ser  Glu Cys Val Leu Gly  Gln Ser Lys
    1025                 1030                1035

Arg Val  Asp Phe Cys Gly Lys  Gly Tyr His Leu Met  Ser Phe Pro
    1040                 1045                1050

Gln Ser  Ala Pro His Gly Val  Val Phe Leu His Val  Thr Tyr Val
    1055                 1060                1065

Pro Ala  Gln Glu Lys Asn Phe  Thr Thr Ala Pro Ala  Ile Cys His
    1070                 1075                1080

Asp Gly  Lys Ala His Phe Pro  Arg Glu Gly Val Phe  Val Ser Asn
    1085                 1090                1095

Gly Thr  His Trp Phe Val Thr  Gln Arg Asn Phe Tyr  Glu Pro Gln
    1100                 1105                1110

Ile Ile  Thr Thr Asp Asn Thr  Phe Val Ser Gly Asn  Cys Asp Val
    1115                 1120                1125

Val Ile  Gly Ile Val Asn Asn  Thr Val Tyr Asp Pro  Leu Gln Pro
    1130                 1135                1140

Glu Leu  Asp Ser Phe Lys Glu  Glu Leu Asp Lys Tyr  Phe Lys Asn
    1145                 1150                1155

His Thr  Ser Pro Asp Val Asp  Leu Gly Asp Ile Ser  Gly Ile Asn
    1160                 1165                1170

Ala Ser  Val Val Asn Ile Gln  Lys Glu Ile Asp Arg  Leu Asn Glu
    1175                 1180                1185

Val Ala  Lys Asn Leu Asn Glu  Ser Leu Ile Asp Leu  Gln Glu Leu
    1190                 1195                1200

Gly Lys  Tyr Glu Gln Tyr Ile  Lys Trp Pro Trp Tyr  Ile Trp Leu
    1205                 1210                1215

Gly Phe  Ile Ala Gly Leu Ile  Ala Ile Val Met Val  Thr Ile Met
    1220                 1225                1230

Leu Cys  Cys Met Thr Ser Cys  Cys Ser Cys Leu Lys  Gly Cys Cys
    1235                 1240                1245

Ser Cys  Gly Ser Cys Cys Lys  Phe Asp Glu Asp Asp  Ser Glu Pro
    1250                 1255                1260

Val Leu  Lys Gly Val Lys Leu  His Tyr Thr
    1265                 1270
```

<210> SEQ ID NO 11
<211> LENGTH: 670
<212> TYPE: PRT
<213> ORGANISM: Artificial Sequence
<220> FEATURE:
<223> OTHER INFORMATION: Artificially synthesized S1 domain of spike protein

<400> SEQUENCE: 11

Val Asn Leu Thr Thr Arg Thr Gln Leu Pro Pro Ala Tyr Thr Asn Ser
1 5 10 15

Phe Thr Arg Gly Val Tyr Tyr Pro Asp Lys Val Phe Arg Ser Ser Val
20 25 30

Leu His Ser Thr Gln Asp Leu Phe Leu Pro Phe Phe Ser Asn Val Thr
35 40 45

Trp Phe His Ala Ile His Val Ser Gly Thr Asn Gly Thr Lys Arg Phe
50 55 60

Asp Asn Pro Val Leu Pro Phe Asn Asp Gly Val Tyr Phe Ala Ser Thr
65 70 75 80

Glu Lys Ser Asn Ile Ile Arg Gly Trp Ile Phe Gly Thr Thr Leu Asp
85 90 95

Ser Lys Thr Gln Ser Leu Leu Ile Val Asn Asn Ala Thr Asn Val Val
100 105 110

Ile Lys Val Cys Glu Phe Gln Phe Cys Asn Asp Pro Phe Leu Gly Val
115 120 125

Tyr Tyr His Lys Asn Asn Lys Ser Trp Met Glu Ser Glu Phe Arg Val
130 135 140

Tyr Ser Ser Ala Asn Asn Cys Thr Phe Glu Tyr Val Ser Gln Pro Phe
145 150 155 160

Leu Met Asp Leu Glu Gly Lys Gln Gly Asn Phe Lys Asn Leu Arg Glu
165 170 175

Phe Val Phe Lys Asn Ile Asp Gly Tyr Phe Lys Ile Tyr Ser Lys His
180 185 190

Thr Pro Ile Asn Leu Val Arg Asp Leu Pro Gln Gly Phe Ser Ala Leu
195 200 205

Glu Pro Leu Val Asp Leu Pro Ile Gly Ile Asn Ile Thr Arg Phe Gln
210 215 220

Thr Leu Leu Ala Leu His Arg Ser Tyr Leu Thr Pro Gly Asp Ser Ser
225 230 235 240

Ser Gly Trp Thr Ala Gly Ala Ala Ala Tyr Tyr Val Gly Tyr Leu Gln
245 250 255

Pro Arg Thr Phe Leu Leu Lys Tyr Asn Glu Asn Gly Thr Ile Thr Asp
260 265 270

Ala Val Asp Cys Ala Leu Asp Pro Leu Ser Glu Thr Lys Cys Thr Leu
275 280 285

Lys Ser Phe Thr Val Glu Lys Gly Ile Tyr Gln Thr Ser Asn Phe Arg
290 295 300

Val Gln Pro Thr Glu Ser Ile Val Arg Phe Pro Asn Ile Thr Asn Leu
305 310 315 320

Cys Pro Phe Gly Glu Val Phe Asn Ala Thr Arg Phe Ala Ser Val Tyr
325 330 335

Ala Trp Asn Arg Lys Arg Ile Ser Asn Cys Val Ala Asp Tyr Ser Val
340 345 350

Leu Tyr Asn Ser Ala Ser Phe Ser Thr Phe Lys Cys Tyr Gly Val Ser

```
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Lys Ser Thr Asn Leu Val Lys Asn Lys Cys Val Asn Phe Asn Phe
        515                 520                 525

Asn Gly Leu Thr Gly Thr Gly Val Leu Thr Glu Ser Asn Lys Lys Phe
    530                 535                 540

Leu Pro Phe Gln Gln Phe Gly Arg Asp Ile Ala Asp Thr Thr Asp Ala
545                 550                 555                 560

Val Arg Asp Pro Gln Thr Leu Glu Ile Leu Asp Ile Thr Pro Cys Ser
                565                 570                 575

Phe Gly Gly Val Ser Val Ile Thr Pro Gly Thr Asn Thr Ser Asn Gln
            580                 585                 590

Val Ala Val Leu Tyr Gln Asp Val Asn Cys Thr Glu Val Pro Val Ala
        595                 600                 605

Ile His Ala Asp Gln Leu Thr Pro Thr Trp Arg Val Tyr Ser Thr Gly
    610                 615                 620

Ser Asn Val Phe Gln Thr Arg Ala Gly Cys Leu Ile Gly Ala Glu His
625                 630                 635                 640

Val Asn Asn Ser Tyr Glu Cys Asp Ile Pro Ile Gly Ala Gly Ile Cys
                645                 650                 655

Ala Ser Tyr Gln Thr Gln Thr Asn Ser Pro Arg Arg Ala Arg
            660                 665                 670


<210> SEQ ID NO 12
<211> LENGTH: 223
<212> TYPE: PRT
<213> ORGANISM: Artificial Sequence
<220> FEATURE:
<223> OTHER INFORMATION: Artificially synthesized receptor binding
      domain (RBD) of spike protein

<400> SEQUENCE: 12

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45
```

-continued

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220

<210> SEQ ID NO 13
<211> LENGTH: 58
<212> TYPE: PRT
<213> ORGANISM: Artificial Sequence
<220> FEATURE:
<223> OTHER INFORMATION: Artificially synthesized PAdelFc

<400> SEQUENCE: 13

Ile Ala Ala Gln His Asp Lys Asp Gln Ser Ala Ala Asp Ser Glu Ile
1               5                   10                  15

Leu His Leu Pro Asn Leu Thr Glu Glu Gln Arg Asn Ala Phe Arg Gln
            20                  25                  30

Ser Leu Ser Asp Asp Pro Ser Val Ser Leu Glu Ile Leu Ala Glu Ala
        35                  40                  45

Lys Lys Leu Asn Asp Ala Gln Ala Pro Lys
    50                  55

<210> SEQ ID NO 14
<211> LENGTH: 58
<212> TYPE: PRT
<213> ORGANISM: Artificial Sequence
<220> FEATURE:
<223> OTHER INFORMATION: Artificially synthesized PAdelFc
      non-immunoglobulin binding protein

<400> SEQUENCE: 14

Ile Ala Ala Gln His Asp Lys Ile Gln Gln Ala Ala Asp Lys Glu Ile
1               5                   10                  15

Leu His Leu Pro Asn Leu Thr Glu Glu Gln Arg Asn Lys Phe Arg Gln
            20                  25                  30

Ser Leu Arg Asp Asp Pro Ser Val Ser Ala Glu Ile Leu Ala Glu Ala
        35                  40                  45

Lys Lys Leu Asn Asp Ala Gln Ala Pro Lys
    50                  55

<210> SEQ ID NO 15
<211> LENGTH: 58
<212> TYPE: PRT
<213> ORGANISM: Artificial Sequence
<220> FEATURE:
<223> OTHER INFORMATION: Artificially synthesized Ig binding protein cs27 as scaffold

<400> SEQUENCE: 15

```
Ile Ala Ala Lys Phe Asp Glu Ala Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Gln Lys Leu Asn Asp Ser Gln Ala Pro Lys
    50                  55
```

<210> SEQ ID NO 16
<211> LENGTH: 58
<212> TYPE: PRT
<213> ORGANISM: Artificial Sequence
<220> FEATURE:
<223> OTHER INFORMATION: Artificially synthesized Ig binding protein C27 as scaffold

<400> SEQUENCE: 16

```
Asn Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55
```

<210> SEQ ID NO 17
<211> LENGTH: 116
<212> TYPE: PRT
<213> ORGANISM: Artificial Sequence
<220> FEATURE:
<223> OTHER INFORMATION: Artificially synthesized spike protein binding protein 212860

<400> SEQUENCE: 17

```
Ile Ala Ala Lys Phe Asp Glu Ala Gln Gln Tyr Ala Phe Tyr Lys Ile
1               5                   10                  15

Leu His Leu Trp Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Arg Lys Leu Asn Thr Ser Gln Ala Pro Lys Ile Ala Ala Lys Phe Asp
    50                  55                  60

Glu Ala Gln Tyr Ala Ala Phe Leu Glu Ile Gln His Leu Pro Asn Leu
65                  70                  75                  80

Thr Glu Glu Gln Arg Gln Ala Phe Ile Val Ser Leu Ala Asp Asp Pro
                85                  90                  95

Ser Val Ser Leu Glu Val Leu Gly Glu Ala Gln Lys Leu Asn Asp Ser
            100                 105                 110

Gln Ala Pro Lys
        115
```

<210> SEQ ID NO 18
<211> LENGTH: 116
<212> TYPE: PRT
<213> ORGANISM: Artificial Sequence
<220> FEATURE:
<223> OTHER INFORMATION: Artificially synthesized spike protein binding protein 212728

<400> SEQUENCE: 18

```
Ile Ala Ala Lys Phe Asp Glu Ala Gln Leu Ala Ala Phe Glu Glu Ile
1               5                   10                  15

Arg His Leu Pro Asn Leu Thr Glu Glu Gln Arg Glu Ala Phe Ile Thr
            20                  25                  30

Ser Leu Tyr Asp Asp Pro Ser Val Ser Leu Glu Val Leu Gly Glu Ala
        35                  40                  45

Gln Lys Leu Asn Asp Ser Gln Ala Pro Lys Ile Ala Ala Lys Phe Asp
    50                  55                  60

Glu Ala Gln Gln Ala Ala Phe Tyr Glu Ile Leu His Leu Pro Asn Pro
65                  70                  75                  80

Thr Glu Trp Gln Arg Asn Tyr Phe Ile Gln Gln Leu Arg Asp Asp Pro
                85                  90                  95

Ser Val Ser Leu Ala Val Leu Gly Arg Ala Gln Val Leu Asn Asp Ser
            100                 105                 110

Gln Ala Pro Lys
        115
```

<210> SEQ ID NO 19
<211> LENGTH: 116
<212> TYPE: PRT
<213> ORGANISM: Artificial Sequence
<220> FEATURE:
<223> OTHER INFORMATION: Artificially synthesized spike protein binding protein 212522

<400> SEQUENCE: 19

```
Ile Ala Ala Lys Phe Asp Glu Ala Gln Gln Ala Ala Phe Tyr Glu Ile
1               5                   10                  15

Leu His Leu Pro Asn Leu Thr Glu Leu Gln Arg Asn Trp Phe Ile Gln
            20                  25                  30

Leu Leu Arg Asp Asp Pro Ser Val Ser Leu Gln Val Leu Gly His Ala
        35                  40                  45

Gln Tyr Leu Asn Asp Ser Gln Ala Pro Lys Ile Ala Ala Lys Phe Asp
    50                  55                  60

Glu Ala Gln Gln Tyr Ala Phe Tyr Gln Ile Leu His Leu His Asn Leu
65                  70                  75                  80

Thr Glu Glu Gln Arg Asn Ala Phe Ile Gln Ser Leu Arg Asp Asp Pro
                85                  90                  95

Ser Val Ser His Glu Val Leu Gly Glu Ala Lys Lys Leu Asn Glu Ser
            100                 105                 110

Gln Ala Pro Lys
        115
```

<210> SEQ ID NO 20
<211> LENGTH: 58
<212> TYPE: PRT
<213> ORGANISM: Artificial Sequence
<220> FEATURE:
<223> OTHER INFORMATION: Artificially synthesized SPike protein binding protein

```
<220> FEATURE:
<221> NAME/KEY: Xaa
<222> LOCATION: (14)..(14)
<220> FEATURE:
<221> NAME/KEY: Xaa
<222> LOCATION: (14)..(14)
<223> OTHER INFORMATION: Xaa may be any amino acid, in some embodiments
      Gln or Glu

<400> SEQUENCE: 20

Ile Ala Ala Lys Phe Asp Glu Ala Gln Leu Ala Ala Phe Xaa Glu Ile
1               5                   10                  15

Arg His Leu Pro Asn Leu Thr Glu Glu Gln Arg Glu Ala Phe Ile Thr
            20                  25                  30

Ser Leu Tyr Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 21
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 21

Ile Ala Ala Lys Phe Asp Glu Ala Gln Leu Ala Ala Phe Glu Glu Ile
1               5                   10                  15

Arg His Leu Pro Asn Leu Thr Glu Glu Gln Arg Glu Ala Phe Ile Thr
            20                  25                  30

Ser Leu Tyr Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 22
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 22

Ile Ala Ala Lys Phe Asp Glu Ala Gln Gln Ala Ala Phe Tyr Glu Ile
1               5                   10                  15

Leu His Leu Pro Asn Pro Thr Glu Trp Gln Arg Asn Tyr Phe Ile Gln
            20                  25                  30

Gln Leu Arg Asp Asp Pro Ser Val Ser Leu Ala Val Leu Gly Arg Ala
        35                  40                  45

Gln Val Leu Asn Asp Ser Gln Ala Pro Lys
    50                  55


<210> SEQ ID NO 23
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 23
```

```
Ile Ala Ala Lys Phe Asp Glu Ala Gln Tyr Ala Ala Phe Leu Glu Ile
1               5                   10                  15

Gln His Leu Pro Asn Leu Thr Glu Glu Gln Arg Gln Ala Phe Ile Val
            20                  25                  30

Ser Leu Ala Asp Asp Pro Ser Val Ser Leu Glu Val Leu Gly Glu Ala
        35                  40                  45

Gln Lys Leu Asn Asp Ser Gln Ala Pro Lys
    50                  55


<210> SEQ ID NO 24
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 24

Ile Ala Ala Lys Phe Asp Glu Ala Gln Gln Ala Ala Phe Tyr Glu Ile
1               5                   10                  15

Leu His Leu Pro Asn Leu Thr Glu Leu Gln Arg Asn Trp Phe Ile Gln
            20                  25                  30

Leu Leu Arg Asp Asp Pro Ser Val Ser Leu Gln Val Leu Gly His Ala
        35                  40                  45

Gln Tyr Leu Asn Asp Ser Gln Ala Pro Lys
    50                  55


<210> SEQ ID NO 25
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 25

Ile Ala Ala Lys Phe Asp Glu Ala Gln Gln Tyr Ala Phe Tyr Gln Ile
1               5                   10                  15

Leu His Leu His Asn Leu Thr Glu Glu Gln Arg Asn Ala Phe Ile Gln
            20                  25                  30

Ser Leu Arg Asp Asp Pro Ser Val Ser His Glu Val Leu Gly Glu Ala
        35                  40                  45

Lys Lys Leu Asn Glu Ser Gln Ala Pro Lys
    50                  55


<210> SEQ ID NO 26
<211> LENGTH: 58
<212> TYPE: PRT
<213> ORGANISM: Artificial Sequence
<220> FEATURE:
<223> OTHER INFORMATION: Artificially synthesized Spike protein binding
      protein

<400> SEQUENCE: 26

Ile Ala Ala Lys Phe Asp Glu Ala Gln Gln Trp Ala Phe Tyr Glu Ile
1               5                   10                  15

Leu His Leu Glu Asn Leu Thr Glu Glu Gln Arg Asn Ala Phe Ile Gln
            20                  25                  30

Ser Leu Arg Asp Asp Pro Ser Val Ser Arg Glu Val Leu Gly Glu Ala
        35                  40                  45
```

Thr Lys Leu Asn Thr Ser Gln Ala Pro Lys
    50                  55

<210> SEQ ID NO 27
<211> LENGTH: 56
<212> TYPE: PRT
<213> ORGANISM: Artificial Sequence
<220> FEATURE:
<223> OTHER INFORMATION: Artificially synthesized Spike binding protein 212434 Ndel2

<400> SEQUENCE: 27

Ala Val Leu Asp Ile Ala Gln His Ser Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Lys Glu Val Leu Gly Glu Ala Gln Lys
        35                  40                  45

Leu Asn Asp Ser Gln Ala Pro Lys
    50                  55

<210> SEQ ID NO 28
<211> LENGTH: 56
<212> TYPE: PRT
<213> ORGANISM: Artificial Sequence
<220> FEATURE:
<223> OTHER INFORMATION: Artificially synthesized spike binding protein 212896

<400> SEQUENCE: 28

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys
    50                  55

<210> SEQ ID NO 29
<211> LENGTH: 231
<212> TYPE: PRT
<213> ORGANISM: Artificial Sequence
<220> FEATURE:
<223> OTHER INFORMATION: Artificially synthesized fusion protein 212895 (fusion of 212434 with (PAdelFc)3)

<400> SEQUENCE: 29

Ala Val Leu Asp Ile Ala Gln His Ser Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Lys Glu Val Leu Gly Glu Ala Gln Lys
        35                  40                  45

Leu Asn Asp Ser Gln Ala Pro Lys Ile Ala Ala Gln His Asp Lys Ile
    50                  55                  60

Gln Gln Ala Ala Asp Lys Glu Ile Leu His Leu Pro Asn Leu Thr Glu
65                  70                  75                  80

Glu Gln Arg Asn Lys Phe Arg Gln Ser Leu Arg Asp Asp Pro Ser Val
                85                  90                  95

Ser Ala Glu Ile Leu Ala Glu Ala Lys Lys Leu Asn Asp Ala Gln Ala

```
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Cys
225                 230


<210> SEQ ID NO 30
<211> LENGTH: 231
<212> TYPE: PRT
<213> ORGANISM: Artificial Sequence
<220> FEATURE:
<223> OTHER INFORMATION: Artificially synthesized fusion protein 212896
      (fusion of 212896 with (PAdelFc)3)

<400> SEQUENCE: 30

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Gln His Asp Lys Ile
    50                  55                  60

Gln Gln Ala Ala Asp Lys Glu Ile Leu His Leu Pro Asn Leu Thr Glu
65                  70                  75                  80

Glu Gln Arg Asn Lys Phe Arg Gln Ser Leu Arg Asp Asp Pro Ser Val
                85                  90                  95

Ser Ala Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220
```

```
Asp Ala Gln Ala Pro Lys Cys
225                 230


<210> SEQ ID NO 31
<211> LENGTH: 365
<212> TYPE: PRT
<213> ORGANISM: Artificial Sequence
<220> FEATURE:
<223> OTHER INFORMATION: Artificially synthesized fusion protein 212897
      (fusion of 212434 dimer with (PAdelFc)4)

<400> SEQUENCE: 31

Ala Val Leu Asp Ile Ala Gln His Ser Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Lys Glu Val Leu Gly Glu Ala Gln Lys
        35                  40                  45

Leu Asn Asp Ser Gln Ala Pro Lys Gln Ala Pro Lys Val Asp Ala Lys
    50                  55                  60

Phe Asp Gln Ala Pro Lys Val Asp Ala Lys Phe Asp Ala Val Leu Asp
65                  70                  75                  80

Ile Ala Gln His Ser Ala Thr Glu Glu Ile Trp Trp Leu Pro Asn Leu
                85                  90                  95

Thr Lys Gln Gln Lys Val Trp Phe Ile Met Ser Leu Thr Gln Asp Pro
            100                 105                 110

Ser Val Ser Lys Glu Val Leu Gly Glu Ala Gln Lys Leu Asn Asp Ser
        115                 120                 125

Gln Ala Pro Lys Ile Ala Ala Gln His Asp Lys Ile Gln Gln Ala Ala
    130                 135                 140

Asp Lys Glu Ile Leu His Leu Pro Asn Leu Thr Glu Glu Gln Arg Asn
145                 150                 155                 160

Lys Phe Arg Gln Ser Leu Arg Asp Asp Pro Ser Val Ser Ala Glu Ile
                165                 170                 175

Leu Ala Glu Ala Lys Lys Leu Asn Asp Ala Gln Ala Pro Lys Ile Ala
            180                 185                 190

Ala Gln His Asp Lys Ile Gln Gln Ala Ala Asp Lys Glu Ile Leu His
        195                 200                 205

Leu Pro Asn Leu Thr Glu Glu Gln Arg Asn Lys Phe Arg Gln Ser Leu
    210                 215                 220

Arg Asp Asp Pro Ser Val Ser Ala Glu Ile Leu Ala Glu Ala Lys Lys
225                 230                 235                 240

Leu Asn Asp Ala Gln Ala Pro Lys Ile Ala Ala Gln His Asp Lys Ile
                245                 250                 255

Gln Gln Ala Ala Asp Lys Glu Ile Leu His Leu Pro Asn Leu Thr Glu
            260                 265                 270

Glu Gln Arg Asn Lys Phe Arg Gln Ser Leu Arg Asp Asp Pro Ser Val
        275                 280                 285

Ser Ala Glu Ile Leu Ala Glu Ala Lys Lys Leu Asn Asp Ala Gln Ala
    290                 295                 300

Pro Lys Ile Ala Ala Gln His Asp Lys Ile Gln Gln Ala Ala Asp Lys
305                 310                 315                 320

Glu Ile Leu His Leu Pro Asn Leu Thr Glu Glu Gln Arg Asn Lys Phe
                325                 330                 335

Arg Gln Ser Leu Arg Asp Asp Pro Ser Val Ser Ala Glu Ile Leu Ala
            340                 345                 350
```

```
Glu Ala Lys Lys Leu Asn Asp Ala Gln Ala Pro Lys Cys
        355                 360                 365
```

<210> SEQ ID NO 32
<211> LENGTH: 230
<212> TYPE: PRT
<213> ORGANISM: Artificial Sequence
<220> FEATURE:
<223> OTHER INFORMATION: Artificially synthesized fusion protein 213147 (213103 with (PAdelFc)2)

<400> SEQUENCE: 32

```
Ala Lys Phe Asp Glu Ala Gln Gln Trp Ala Phe Tyr Glu Ile Leu His
1               5                   10                  15

Leu Glu Asn Leu Thr Glu Glu Gln Arg Asn Ala Phe Ile Gln Ser Leu
            20                  25                  30

Arg Asp Asp Pro Ser Val Ser Arg Glu Val Leu Gly Glu Ala Thr Lys
        35                  40                  45

Leu Asn Thr Ser Gln Ala Pro Lys Ile Ala Ala Lys Phe Asp Glu Ala
    50                  55                  60

Gln Leu Ala Ala Phe Gln Glu Ile Arg His Leu Pro Asn Leu Thr Glu
65                  70                  75                  80

Glu Gln Arg Glu Ala Phe Ile Thr Ser Leu Tyr Asp Asp Pro Ser Val
                85                  90                  95

Ser Leu Glu Val Leu Gly Glu Ala Gln Lys Leu Asn Asp Ser Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys
225                 230
```

<210> SEQ ID NO 33
<211> LENGTH: 230
<212> TYPE: PRT
<213> ORGANISM: Artificial Sequence
<220> FEATURE:
<223> OTHER INFORMATION: Artificially synthesized fusion protein 213152 (212728 with (PAdelFc)2)

<400> SEQUENCE: 33

```
Ala Lys Phe Asp Glu Ala Gln Leu Ala Ala Phe Glu Glu Ile Arg His
1               5                   10                  15

Leu Pro Asn Leu Thr Glu Glu Gln Arg Glu Ala Phe Ile Thr Ser Leu
            20                  25                  30

Tyr Asp Asp Pro Ser Val Ser Leu Glu Val Leu Gly Glu Ala Gln Lys
        35                  40                  45
```

```
Leu Asn Asp Ser Gln Ala Pro Lys Ile Ala Ala Lys Phe Asp Glu Ala
    50                  55                  60

Gln Gln Ala Ala Phe Tyr Glu Ile Leu His Leu Pro Asn Pro Thr Glu
65                  70                  75                  80

Trp Gln Arg Asn Tyr Phe Ile Gln Gln Leu Arg Asp Asp Pro Ser Val
                85                  90                  95

Ser Leu Ala Val Leu Gly Arg Ala Gln Val Leu Asn Asp Ser Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys
225                 230
```

<210> SEQ ID NO 34
<211> LENGTH: 114
<212> TYPE: PRT
<213> ORGANISM: Artificial Sequence
<220> FEATURE:
<223> OTHER INFORMATION: Artificially synthesized spike binding protein
      213103 Ndel2

<400> SEQUENCE: 34

```
Ala Lys Phe Asp Glu Ala Gln Gln Trp Ala Phe Tyr Glu Ile Leu His
1               5                   10                  15

Leu Glu Asn Leu Thr Glu Glu Gln Arg Asn Ala Phe Ile Gln Ser Leu
            20                  25                  30

Arg Asp Asp Pro Ser Val Ser Arg Glu Val Leu Gly Glu Ala Thr Lys
        35                  40                  45

Leu Asn Thr Ser Gln Ala Pro Lys Ile Ala Ala Lys Phe Asp Glu Ala
    50                  55                  60

Gln Leu Ala Ala Phe Gln Glu Ile Arg His Leu Pro Asn Leu Thr Glu
65                  70                  75                  80

Glu Gln Arg Glu Ala Phe Ile Thr Ser Leu Tyr Asp Asp Pro Ser Val
                85                  90                  95

Ser Leu Glu Val Leu Gly Glu Ala Gln Lys Leu Asn Asp Ser Gln Ala
            100                 105                 110

Pro Lys
```

<210> SEQ ID NO 35
<211> LENGTH: 114
<212> TYPE: PRT
<213> ORGANISM: Artificial Sequence
<220> FEATURE:
<223> OTHER INFORMATION: Artificially synthesized spike binding protein
      212728 Ndel2

<400> SEQUENCE: 35

```
Ala Lys Phe Asp Glu Ala Gln Leu Ala Ala Phe Glu Glu Ile Arg His
1               5                   10                  15

Leu Pro Asn Leu Thr Glu Glu Gln Arg Glu Ala Phe Ile Thr Ser Leu
            20                  25                  30

Tyr Asp Asp Pro Ser Val Ser Leu Glu Val Leu Gly Glu Ala Gln Lys
        35                  40                  45

Leu Asn Asp Ser Gln Ala Pro Lys Ile Ala Ala Lys Phe Asp Glu Ala
    50                  55                  60

Gln Gln Ala Ala Phe Tyr Glu Ile Leu His Leu Pro Asn Pro Thr Glu
65                  70                  75                  80

Trp Gln Arg Asn Tyr Phe Ile Gln Gln Leu Arg Asp Asp Pro Ser Val
                85                  90                  95

Ser Leu Ala Val Leu Gly Arg Ala Gln Val Leu Asn Asp Ser Gln Ala
            100                 105                 110

Pro Lys
```

<210> SEQ ID NO 36
<211> LENGTH: 116
<212> TYPE: PRT
<213> ORGANISM: Artificial Sequence
<220> FEATURE:
<223> OTHER INFORMATION: Artificially synthesized spike binding protein 212880 (SEQ37+SEQ3)

<400> SEQUENCE: 36

```
Ile Ala Ala Lys Phe Asp Glu Ala Gln Gln Leu Ala Phe Tyr Leu Ile
1               5                   10                  15

Leu His Leu Ile Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
        35                  40                  45

Tyr Lys Leu Asn Leu Ser Gln Ala Pro Lys Ile Ala Ala Lys Phe Asp
    50                  55                  60

Glu Ala Gln Leu Ala Ala Phe Gln Glu Ile Arg His Leu Pro Asn Leu
65                  70                  75                  80

Thr Glu Glu Gln Arg Glu Ala Phe Ile Thr Ser Leu Tyr Asp Asp Pro
                85                  90                  95

Ser Val Ser Leu Glu Val Leu Gly Glu Ala Gln Lys Leu Asn Asp Ser
            100                 105                 110

Gln Ala Pro Lys
        115
```

<210> SEQ ID NO 37
<211> LENGTH: 58
<212> TYPE: PRT
<213> ORGANISM: Artificial Sequence
<220> FEATURE:
<223> OTHER INFORMATION: Artificially synthesized spike binding protein 212880 monomer

<400> SEQUENCE: 37

```
Ile Ala Ala Lys Phe Asp Glu Ala Gln Gln Leu Ala Phe Tyr Leu Ile
1               5                   10                  15

Leu His Leu Ile Asn Leu Thr Glu Glu Gln Arg Asn Ala Phe Ile Gln
            20                  25                  30

Ser Leu Arg Asp Asp Pro Ser Val Ser Leu Glu Val Leu Gly Glu Ala
```

```
        35                  40                  45

Tyr Lys Leu Asn Leu Ser Gln Ala Pro Lys
    50                  55


<210> SEQ ID NO 38
<211> LENGTH: 172
<212> TYPE: PRT
<213> ORGANISM: Artificial Sequence
<220> FEATURE:
<223> OTHER INFORMATION: Artificially synthesized fusion protein of
      SEQ28 with (PAdelFc)2

<400> SEQUENCE: 38

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Gln His Asp Lys Ile
    50                  55                  60

Gln Gln Ala Ala Asp Lys Glu Ile Leu His Leu Pro Asn Leu Thr Glu
65                  70                  75                  80

Glu Gln Arg Asn Lys Phe Arg Gln Ser Leu Arg Asp Asp Pro Ser Val
                85                  90                  95

Ser Ala Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys
                165                 170


<210> SEQ ID NO 39
<211> LENGTH: 230
<212> TYPE: PRT
<213> ORGANISM: Artificial Sequence
<220> FEATURE:
<223> OTHER INFORMATION: Artificially synthesized fusion protein of
      SEQ28-PAdelFc-SEQ28-PAdelFc

<400> SEQUENCE: 39

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Gln His Asp Lys Ile
    50                  55                  60

Gln Gln Ala Ala Asp Lys Glu Ile Leu His Leu Pro Asn Leu Thr Glu
65                  70                  75                  80

Glu Gln Arg Asn Lys Phe Arg Gln Ser Leu Arg Asp Asp Pro Ser Val
                85                  90                  95

Ser Ala Glu Ile Leu Ala Glu Ala Lys Lys Leu Asn Asp Ala Gln Ala
```

```
            100                 105                 110

Pro Lys Ile Ala Ala Val Leu Asp Ile Asp Gln His Ala Ala Thr Glu
        115                 120                 125

Glu Ile Trp Trp Leu Pro Asn Leu Thr Lys Gln Gln Lys Val Trp Phe
    130                 135                 140

Ile Met Ser Leu Thr Gln Asp Pro Ser Val Ser Leu Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys
225                 230
```

<210> SEQ ID NO 40
<211> LENGTH: 56
<212> TYPE: PRT
<213> ORGANISM: Artificial Sequence
<220> FEATURE:
<223> OTHER INFORMATION: Artificially synthesized spike protein binding protein

<400> SEQUENCE: 40

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Val Leu Gly Glu Ala Arg Lys
        35                  40                  45

Leu Asn Thr Ser Gln Ala Pro Lys
    50                  55
```

<210> SEQ ID NO 41
<211> LENGTH: 56
<212> TYPE: PRT
<213> ORGANISM: Artificial Sequence
<220> FEATURE:
<223> OTHER INFORMATION: Artificially synthesized spike binding protein 217800-1

<400> SEQUENCE: 41

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys
    50                  55
```

<210> SEQ ID NO 42
<211> LENGTH: 58
<212> TYPE: PRT
<213> ORGANISM: Artificial Sequence
<220> FEATURE:
<223> OTHER INFORMATION: Artificially synthesized spike protein binding protein 217800-2

<400> SEQUENCE: 42

Ile Ala Ala Lys Phe Asp Glu Ala Gln Tyr Ala Ala Phe Leu Glu Ile
1 5 10 15

Val His Leu Pro Asn Leu Thr Glu Glu Gln Arg Gln Ala Phe Ile Ala
20 25 30

Ser Leu Trp Asp Asp Pro Ser Val Ser Leu Glu Ile Leu Ala Glu Ala
35 40 45

Lys Lys Leu Asn Asp Ala Gln Ala Pro Lys
50 55

<210> SEQ ID NO 43
<211> LENGTH: 114
<212> TYPE: PRT
<213> ORGANISM: Artificial Sequence
<220> FEATURE:
<223> OTHER INFORMATION: Artificially synthesized spike protein binding protein 217800

<400> SEQUENCE: 43

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Ile Leu Ala Glu Ala Arg Lys
35 40 45

Leu Asn Thr Ala Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys

<210> SEQ ID NO 44
<211> LENGTH: 114
<212> TYPE: PRT
<213> ORGANISM: Artificial Sequence
<220> FEATURE:
<223> OTHER INFORMATION: Artificially synthesized spike protein binding protein 217798

<400> SEQUENCE: 44

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Val Leu Gly Glu Ala Arg Lys
35 40 45

Leu Asn Thr Ser Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys

<210> SEQ ID NO 45
<211> LENGTH: 114
<212> TYPE: PRT
<213> ORGANISM: Artificial Sequence
<220> FEATURE:
<223> OTHER INFORMATION: Artificially synthesized spike protein binding protein (SEQ2 plus SEQ3)

<400> SEQUENCE: 45

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Val Leu Gly Glu Ala Arg Lys
35 40 45

Leu Asn Thr Ser Gln Ala Pro Lys Ile Ala Ala Lys Phe Asp Glu Ala
50 55 60

Gln Leu Ala Ala Phe Gln Glu Ile Arg His Leu Pro Asn Leu Thr Glu
65 70 75 80

Glu Gln Arg Glu Ala Phe Ile Thr Ser Leu Tyr Asp Asp Pro Ser Val
85 90 95

Ser Leu Glu Val Leu Gly Glu Ala Gln Lys Leu Asn Asp Ser Gln Ala
100 105 110

Pro Lys

<210> SEQ ID NO 46
<211> LENGTH: 230
<212> TYPE: PRT
<213> ORGANISM: Artificial Sequence
<220> FEATURE:
<223> OTHER INFORMATION: Artificially synthesized spike protein binding protein (217800 tetramer)

<400> SEQUENCE: 46

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Ile Leu Ala Glu Ala Arg Lys
35 40 45

Leu Asn Thr Ala Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys Ile Ala Ala Lys Phe Asp Glu Ala Gln Gln Tyr Ala Phe Tyr
115 120 125

Lys Ile Leu His Leu Trp Asn Leu Thr Glu Glu Gln Arg Asn Ala Phe
130 135 140

Ile Gln Ser Leu Arg Asp Asp Pro Ser Val Ser Leu Glu Ile Leu Ala
145 150 155 160

```
Glu Ala Arg Lys Leu Asn Thr Ala Gln Ala Pro Lys Ile Ala Ala Lys
                165                 170                 175

Phe Asp Glu Ala Gln Tyr Ala Ala Phe Leu Glu Ile Val His Leu Pro
            180                 185                 190

Asn Leu Thr Glu Glu Gln Arg Gln Ala Phe Ile Ala Ser Leu Trp Asp
        195                 200                 205

Asp Pro Ser Val Ser Leu Glu Ile Leu Ala Glu Ala Lys Lys Leu Asn
    210                 215                 220

Asp Ala Gln Ala Pro Lys
225                 230


<210> SEQ ID NO 47
<211> LENGTH: 347
<212> TYPE: PRT
<213> ORGANISM: Artificial Sequence
<220> FEATURE:
<223> OTHER INFORMATION: Artificially synthesized 212361 trimer (217797)

<400> SEQUENCE: 47

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Val Leu Gly Glu Ala Arg Lys
        35                  40                  45

Leu Asn Thr Ser Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Val Leu Gly Glu Ala Gln Lys Leu Asn Asp Ser Gln Ala
            100                 105                 110

Pro Lys Ile Ala Ala Lys Phe Asp Glu Ala Gln Gln Tyr Ala Phe Tyr
        115                 120                 125

Lys Ile Leu His Leu Trp Asn Leu Thr Glu Glu Gln Arg Asn Ala Phe
    130                 135                 140

Ile Gln Ser Leu Arg Asp Asp Pro Ser Val Ser Leu Glu Val Leu Gly
145                 150                 155                 160

Glu Ala Arg Lys Leu Asn Thr Ser Gln Ala Pro Lys Ile Ala Ala Lys
                165                 170                 175

Phe Asp Glu Ala Gln Tyr Ala Ala Phe Leu Glu Ile Val His Leu Pro
            180                 185                 190

Asn Leu Thr Glu Glu Gln Arg Gln Ala Phe Ile Ala Ser Leu Trp Asp
        195                 200                 205

Asp Pro Ser Val Ser Leu Glu Val Leu Gly Glu Ala Gln Lys Leu Asn
    210                 215                 220

Asp Ser Gln Ala Pro Lys Ile Ala Ala Lys Phe Asp Glu Ala Gln Gln
225                 230                 235                 240

Tyr Ala Phe Tyr Lys Ile Leu His Leu Trp Asn Leu Thr Glu Glu Gln
                245                 250                 255

Arg Asn Ala Phe Ile Gln Ser Leu Arg Asp Asp Pro Ser Val Ser Leu
            260                 265                 270

Glu Val Leu Gly Glu Ala Arg Lys Leu Asn Thr Ser Gln Ala Pro Lys
        275                 280                 285
```

Ile Ala Ala Lys Phe Asp Glu Ala Gln Tyr Ala Ala Phe Leu Glu Ile
290 295 300

Val His Leu Pro Asn Leu Thr Glu Glu Gln Arg Gln Ala Phe Ile Ala
305 310 315 320

Ser Leu Trp Asp Asp Pro Ser Val Ser Leu Glu Val Leu Gly Glu Ala
325 330 335

Gln Lys Leu Asn Asp Ser Gln Ala Pro Lys Cys
340 345

<210> SEQ ID NO 48
<211> LENGTH: 231
<212> TYPE: PRT
<213> ORGANISM: Artificial Sequence
<220> FEATURE:
<223> OTHER INFORMATION: Artificially synthesized Fusion protein 217238 (212361 fused to (PAdelFc)2)

<400> SEQUENCE: 48

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Val Leu Gly Glu Ala Arg Lys
35 40 45

Leu Asn Thr Ser Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Val Leu Gly Glu Ala Gln Lys Leu Asn Asp Ser Gln Ala
100 105 110

Pro Lys Ile Ala Ala Gln His Asp Lys Ile Gln Gln Ala Ala Asp Lys
115 120 125

Glu Ile Leu His Leu Pro Asn Leu Thr Glu Glu Gln Arg Asn Lys Phe
130 135 140

Arg Gln Ser Leu Arg Asp Asp Pro Ser Val Ser Ala Glu Ile Leu Ala
145 150 155 160

Glu Ala Lys Lys Leu Asn Asp Ala Gln Ala Pro Lys Ile Ala Ala Gln
165 170 175

His Asp Lys Ile Gln Gln Ala Ala Asp Lys Glu Ile Leu His Leu Pro
180 185 190

Asn Leu Thr Glu Glu Gln Arg Asn Lys Phe Arg Gln Ser Leu Arg Asp
195 200 205

Asp Pro Ser Val Ser Ala Glu Ile Leu Ala Glu Ala Lys Lys Leu Asn
210 215 220

Asp Ala Gln Ala Pro Lys Cys
225 230

<210> SEQ ID NO 49
<211> LENGTH: 231
<212> TYPE: PRT
<213> ORGANISM: Artificial Sequence
<220> FEATURE:
<223> OTHER INFORMATION: Artificially synthesized Fusion protein 218898

<400> SEQUENCE: 49

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Val Leu Gly Glu Ala Arg Lys
35 40 45

Leu Asn Thr Ser Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys Ile Ala Ala Gln His Asp Lys Ile Gln Gln Ala Ala Asp Lys
115 120 125

Glu Ile Leu His Leu Pro Asn Leu Thr Glu Glu Gln Arg Asn Lys Phe
130 135 140

Arg Gln Ser Leu Arg Asp Asp Pro Ser Val Ser Ala Glu Ile Leu Ala
145 150 155 160

Glu Ala Lys Lys Leu Asn Asp Ala Gln Ala Pro Lys Ile Ala Ala Gln
165 170 175

His Asp Lys Ile Gln Gln Ala Ala Asp Lys Glu Ile Leu His Leu Pro
180 185 190

Asn Leu Thr Glu Glu Gln Arg Asn Lys Phe Arg Gln Ser Leu Arg Asp
195 200 205

Asp Pro Ser Val Ser Ala Glu Ile Leu Ala Glu Ala Lys Lys Leu Asn
210 215 220

Asp Ala Gln Ala Pro Lys Cys
225 230

<210> SEQ ID NO 50
<211> LENGTH: 347
<212> TYPE: PRT
<213> ORGANISM: Artificial Sequence
<220> FEATURE:
<223> OTHER INFORMATION: Artificially synthesized Fusion protein 217799

<400> SEQUENCE: 50

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Val Leu Gly Glu Ala Arg Lys
35 40 45

Leu Asn Thr Ser Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys Ile Ala Ala Lys Phe Asp Glu Ala Gln Gln Tyr Ala Phe Tyr
115 120 125

```
Lys Ile Leu His Leu Trp Asn Leu Thr Glu Glu Gln Arg Asn Ala Phe
    130                 135                 140

Ile Gln Ser Leu Arg Asp Asp Pro Ser Val Ser Leu Glu Val Leu Gly
145                 150                 155                 160

Glu Ala Arg Lys Leu Asn Thr Ser Gln Ala Pro Lys Ile Ala Ala Lys
                165                 170                 175

Phe Asp Glu Ala Gln Tyr Ala Ala Phe Leu Glu Ile Val His Leu Pro
            180                 185                 190

Asn Leu Thr Glu Glu Gln Arg Gln Ala Phe Ile Ala Ser Leu Trp Asp
        195                 200                 205

Asp Pro Ser Val Ser Leu Glu Ile Leu Ala Glu Ala Lys Lys Leu Asn
    210                 215                 220

Asp Ala Gln Ala Pro Lys Ile Ala Ala Gln His Asp Lys Ile Gln Gln
225                 230                 235                 240

Ala Ala Asp Lys Glu Ile Leu His Leu Pro Asn Leu Thr Glu Glu Gln
                245                 250                 255

Arg Asn Lys Phe Arg Gln Ser Leu Arg Asp Asp Pro Ser Val Ser Ala
            260                 265                 270

Glu Ile Leu Ala Glu Ala Lys Lys Leu Asn Asp Ala Gln Ala Pro Lys
        275                 280                 285

Ile Ala Ala Gln His Asp Lys Ile Gln Gln Ala Ala Asp Lys Glu Ile
    290                 295                 300

Leu His Leu Pro Asn Leu Thr Glu Glu Gln Arg Asn Lys Phe Arg Gln
305                 310                 315                 320

Ser Leu Arg Asp Asp Pro Ser Val Ser Ala Glu Ile Leu Ala Glu Ala
                325                 330                 335

Lys Lys Leu Asn Asp Ala Gln Ala Pro Lys Cys
            340                 345
```

<210> SEQ ID NO 51
<211> LENGTH: 231
<212> TYPE: PRT
<213> ORGANISM: Artificial Sequence
<220> FEATURE:
<223> OTHER INFORMATION: Artificially synthesized Fusion protein 217800

<400> SEQUENCE: 51

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140
```

```
Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Cys
225                 230


<210> SEQ ID NO 52
<211> LENGTH: 231
<212> TYPE: PRT
<213> ORGANISM: Artificial Sequence
<220> FEATURE:
<223> OTHER INFORMATION: Artificially synthesized Fusion protein
      SEQ28xSEQ43xPAdelFc

<400> SEQUENCE: 52

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Lys Phe Asp Glu Ala
    50                  55                  60

Gln Gln Tyr Ala Phe Tyr Lys Ile Leu His Leu Trp Asn Leu Thr Glu
65                  70                  75                  80

Glu Gln Arg Asn Ala Phe Ile Gln Ser Leu Arg Asp Asp Pro Ser Val
                85                  90                  95

Ser Leu Glu Ile Leu Ala Glu Ala Arg Lys Leu Asn Thr Ala Gln Ala
            100                 105                 110

Pro Lys Ile Ala Ala Lys Phe Asp Glu Ala Gln Tyr Ala Ala Phe Leu
        115                 120                 125

Glu Ile Val His Leu Pro Asn Leu Thr Glu Glu Gln Arg Gln Ala Phe
    130                 135                 140

Ile Ala Ser Leu Trp Asp Asp Pro Ser Val Ser Leu Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Cys
225                 230


<210> SEQ ID NO 53
<211> LENGTH: 231
<212> TYPE: PRT
<213> ORGANISM: Artificial Sequence
```

<220> FEATURE:
<223> OTHER INFORMATION: Artificially synthesized Fusion protein (SEQ43xSEQ28xPAdelFc)

<400> SEQUENCE: 53

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Val Leu Asp Ile Asp Gln His Ala Ala Thr Glu
        115                 120                 125

Glu Ile Trp Trp Leu Pro Asn Leu Thr Lys Gln Gln Lys Val Trp Phe
    130                 135                 140

Ile Met Ser Leu Thr Gln Asp Pro Ser Val Ser Leu Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Cys
225                 230
```

<210> SEQ ID NO 54
<211> LENGTH: 288
<212> TYPE: PRT
<213> ORGANISM: Artificial Sequence
<220> FEATURE:
<223> OTHER INFORMATION: Artificially synthesized Fusion protein (217800 dimer x PAdelFc)

<400> SEQUENCE: 54

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95
```

Ser Leu Glu Ile Leu Ala Glu Ala Lys Lys Leu Asn Asp Ala Gln Ala
100 105 110

Pro Lys Ile Ala Ala Lys Phe Asp Glu Ala Gln Gln Tyr Ala Phe Tyr
115 120 125

Lys Ile Leu His Leu Trp Asn Leu Thr Glu Glu Gln Arg Asn Ala Phe
130 135 140

Ile Gln Ser Leu Arg Asp Asp Pro Ser Val Ser Leu Glu Ile Leu Ala
145 150 155 160

Glu Ala Arg Lys Leu Asn Thr Ala Gln Ala Pro Lys Ile Ala Ala Lys
165 170 175

Phe Asp Glu Ala Gln Tyr Ala Ala Phe Leu Glu Ile Val His Leu Pro
180 185 190

Asn Leu Thr Glu Glu Gln Arg Gln Ala Phe Ile Ala Ser Leu Trp Asp
195 200 205

Asp Pro Ser Val Ser Leu Glu Ile Leu Ala Glu Ala Lys Lys Leu Asn
210 215 220

Asp Ala Gln Ala Pro Lys Ile Ala Ala Gln His Asp Lys Ile Gln Gln
225 230 235 240

Ala Ala Asp Lys Glu Ile Leu His Leu Pro Asn Leu Thr Glu Glu Gln
245 250 255

Arg Asn Lys Phe Arg Gln Ser Leu Arg Asp Asp Pro Ser Val Ser Ala
260 265 270

Glu Ile Leu Ala Glu Ala Lys Lys Leu Asn Asp Ala Gln Ala Pro Lys
275 280 285

<210> SEQ ID NO 55
<211> LENGTH: 346
<212> TYPE: PRT
<213> ORGANISM: Artificial Sequence
<220> FEATURE:
<223> OTHER INFORMATION: Artificially synthesized Fusion protein
217800 x PAdelFc

<400> SEQUENCE: 55

Ala Lys Phe Asp Glu Ala Gln Gln Tyr Ala Phe Tyr Lys Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Leu Glu Ile Leu Ala Glu Ala Arg Lys
35 40 45

Leu Asn Thr Ala Gln Ala Pro Lys Ile Ala Ala Lys Phe Asp Glu Ala
50 55 60

Gln Tyr Ala Ala Phe Leu Glu Ile Val His Leu Pro Asn Leu Thr Glu
65 70 75 80

Glu Gln Arg Gln Ala Phe Ile Ala Ser Leu Trp Asp Asp Pro Ser Val
85 90 95

Ser Leu Glu Ile Leu Ala Glu Ala Lys Lys Leu Asn Asp Ala Gln Ala
100 105 110

Pro Lys Ile Ala Ala Lys Phe Asp Glu Ala Gln Gln Tyr Ala Phe Tyr
115 120 125

Lys Ile Leu His Leu Trp Asn Leu Thr Glu Glu Gln Arg Asn Ala Phe
130 135 140

Ile Gln Ser Leu Arg Asp Asp Pro Ser Val Ser Leu Glu Ile Leu Ala
145 150 155 160

Glu Ala Arg Lys Leu Asn Thr Ala Gln Ala Pro Lys Ile Ala Ala Lys

```
                165                 170                 175

Phe Asp Glu Ala Gln Tyr Ala Ala Phe Leu Glu Ile Val His Leu Pro
            180                 185                 190

Asn Leu Thr Glu Glu Gln Arg Gln Ala Phe Ile Ala Ser Leu Trp Asp
        195                 200                 205

Asp Pro Ser Val Ser Leu Glu Ile Leu Ala Glu Ala Lys Lys Leu Asn
    210                 215                 220

Asp Ala Gln Ala Pro Lys Ile Ala Ala Gln His Asp Lys Ile Gln Gln
225                 230                 235                 240

Ala Ala Asp Lys Glu Ile Leu His Leu Pro Asn Leu Thr Glu Glu Gln
                245                 250                 255

Arg Asn Lys Phe Arg Gln Ser Leu Arg Asp Asp Pro Ser Val Ser Ala
            260                 265                 270

Glu Ile Leu Ala Glu Ala Lys Lys Leu Asn Asp Ala Gln Ala Pro Lys
        275                 280                 285

Ile Ala Ala Gln His Asp Lys Ile Gln Gln Ala Ala Asp Lys Glu Ile
    290                 295                 300

Leu His Leu Pro Asn Leu Thr Glu Glu Gln Arg Asn Lys Phe Arg Gln
305                 310                 315                 320

Ser Leu Arg Asp Asp Pro Ser Val Ser Ala Glu Ile Leu Ala Glu Ala
                325                 330                 335

Lys Lys Leu Asn Asp Ala Gln Ala Pro Lys
            340                 345


<210> SEQ ID NO 56
<211> LENGTH: 229
<212> TYPE: PRT
<213> ORGANISM: Artificial Sequence
<220> FEATURE:
<223> OTHER INFORMATION: Artificially synthesized Fusion protein 217382
      (212361 W20P) (no binding to spike protein)

<400> SEQUENCE: 56

Ala Lys Phe Asp Glu Ala Gln Gln Tyr Ala Phe Tyr Lys Ile Leu His
1               5                   10                  15

Leu Pro Asn Leu Thr Glu Glu Gln Arg Asn Ala Phe Ile Gln Ser Leu
            20                  25                  30

Arg Asp Asp Pro Ser Val Ser Leu Glu Val Leu Gly Glu Ala Arg Lys
        35                  40                  45

Leu Asn Thr Ser Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Val Leu Gly Glu Ala Gln Lys Leu Asn Asp Ser Gln Ala
            100                 105                 110

Pro Lys Ala Gln His Asp Lys Ile Gln Gln Ala Ala Asp Lys Glu Ile
        115                 120                 125

Leu His Leu Pro Asn Leu Thr Glu Glu Gln Arg Asn Lys Phe Arg Gln
    130                 135                 140

Ser Leu Arg Asp Asp Pro Ser Val Ser Ala Glu Ile Leu Ala Glu Ala
145                 150                 155                 160

Lys Lys Leu Asn Asp Ala Gln Ala Pro Lys Ile Ala Ala Gln His Asp
                165                 170                 175
```

```
Lys Ile Gln Gln Ala Ala Asp Lys Glu Ile Leu His Leu Pro Asn Leu
            180                 185                 190

Thr Glu Glu Gln Arg Asn Lys Phe Arg Gln Ser Leu Arg Asp Asp Pro
        195                 200                 205

Ser Val Ser Ala Glu Ile Leu Ala Glu Ala Lys Lys Leu Asn Asp Ala
    210                 215                 220

Gln Ala Pro Lys Cys
225
```

<210> SEQ ID NO 57
<211> LENGTH: 114
<212> TYPE: PRT
<213> ORGANISM: Artificial Sequence
<220> FEATURE:
<223> OTHER INFORMATION: Artificially synthesized Spike binding protein 212864 (LQRETY-group)

<400> SEQUENCE: 57

```
Ala Lys Phe Asp Glu Ala Gln Gln Gln Ala Phe Tyr Arg Ile Leu His
1               5                   10                  15

Leu Ile Asn Leu Thr Glu Glu Gln Arg Asn Ala Phe Ile Gln Ser Leu
            20                  25                  30

Arg Asp Asp Pro Ser Val Ser Thr Glu Val Leu Gly Glu Ala Gln Lys
        35                  40                  45

Leu Asn Thr Ser Gln Ala Pro Lys Ile Ala Ala Lys Phe Asp Glu Ala
    50                  55                  60

Gln Leu Ala Ala Phe Gln Glu Ile Arg His Leu Pro Asn Leu Thr Glu
65                  70                  75                  80

Glu Gln Arg Glu Ala Phe Ile Thr Ser Leu Tyr Asp Asp Pro Ser Val
                85                  90                  95

Ser Leu Glu Val Leu Gly Glu Ala Gln Lys Leu Asn Asp Ser Gln Ala
            100                 105                 110

Pro Lys
```

<210> SEQ ID NO 58
<211> LENGTH: 114
<212> TYPE: PRT
<213> ORGANISM: Artificial Sequence
<220> FEATURE:
<223> OTHER INFORMATION: Artificially synthesized Spike protein binding protein 213102 (LQRETY-group)

<400> SEQUENCE: 58

```
Ala Lys Phe Asp Glu Ala Gln Gln Ala Ala Phe Tyr Leu Ile Leu His
1               5                   10                  15

Leu His Asn Leu Thr Glu Glu Gln Arg Asn Ala Phe Ile Gln Ser Leu
            20                  25                  30

Arg Asp Asp Pro Ser Val Ser Tyr Glu Val Leu Gly Glu Ala Gln Lys
        35                  40                  45

Leu Asn Leu Ser Gln Ala Pro Lys Ile Ala Ala Lys Phe Asp Glu Ala
    50                  55                  60

Gln Leu Ala Ala Phe Gln Glu Ile Arg His Leu Pro Asn Leu Thr Glu
65                  70                  75                  80

Glu Gln Arg Glu Ala Phe Ile Thr Ser Leu Tyr Asp Asp Pro Ser Val
                85                  90                  95

Ser Leu Glu Val Leu Gly Glu Ala Gln Lys Leu Asn Asp Ser Gln Ala
            100                 105                 110

Pro Lys
```

<210> SEQ ID NO 59
<211> LENGTH: 114
<212> TYPE: PRT
<213> ORGANISM: Artificial Sequence
<220> FEATURE:
<223> OTHER INFORMATION: Artificially synthesized spike protein binding protein 213101 (LQRETY-group)

<400> SEQUENCE: 59

Ala Lys Phe Asp Glu Ala Gln Gln Gln Ala Phe Tyr His Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Thr Glu Val Leu Gly Glu Ala Glu Lys
35 40 45

Leu Asn Ile Ser Gln Ala Pro Lys Ile Ala Ala Lys Phe Asp Glu Ala
50 55 60

Gln Leu Ala Ala Phe Gln Glu Ile Arg His Leu Pro Asn Leu Thr Glu
65 70 75 80

Glu Gln Arg Glu Ala Phe Ile Thr Ser Leu Tyr Asp Asp Pro Ser Val
85 90 95

Ser Leu Glu Val Leu Gly Glu Ala Gln Lys Leu Asn Asp Ser Gln Ala
100 105 110

Pro Lys

<210> SEQ ID NO 60
<211> LENGTH: 114
<212> TYPE: PRT
<213> ORGANISM: Artificial Sequence
<220> FEATURE:
<223> OTHER INFORMATION: Artificially synthesized spike protein binding protein 212853 (LQRETY-group)

<400> SEQUENCE: 60

Ala Lys Phe Asp Glu Ala Gln Gln Tyr Ala Phe Tyr Trp Ile Leu His
1 5 10 15

Leu Trp Asn Leu Thr Glu Glu Gln Arg Asn Ala Phe Ile Gln Ser Leu
20 25 30

Arg Asp Asp Pro Ser Val Ser Trp Glu Val Leu Gly Glu Ala Tyr Lys
35 40 45

Leu Asn Leu Ser Gln Ala Pro Lys Ile Ala Ala Lys Phe Asp Glu Ala
50 55 60

Gln Leu Ala Ala Phe Gln Glu Ile Arg His Leu Pro Asn Leu Thr Glu
65 70 75 80

Glu Gln Arg Glu Ala Phe Ile Thr Ser Leu Tyr Asp Asp Pro Ser Val
85 90 95

Ser Leu Glu Val Leu Gly Glu Ala Gln Lys Leu Asn Asp Ser Gln Ala
100 105 110

Pro Lys

<210> SEQ ID NO 61
<211> LENGTH: 114
<212> TYPE: PRT
<213> ORGANISM: Artificial Sequence
<220> FEATURE:
<223> OTHER INFORMATION: Artificially synthesized spike protein binding protein 213100 (LQRETY group)

<400> SEQUENCE: 61

```
Ala Lys Phe Asp Glu Ala Gln Leu Ala Ala Phe Gln Glu Ile Arg His
1               5                   10                  15

Leu Pro Asn Leu Thr Glu Glu Gln Arg Glu Ala Phe Ile Thr Ser Leu
            20                  25                  30

Tyr Asp Asp Pro Ser Val Ser Leu Glu Val Leu Gly Glu Ala Gln Lys
        35                  40                  45

Leu Asn Asp Ser Gln Ala Pro Lys Ile Ala Ala Lys Phe Asp Glu Ala
    50                  55                  60

Gln Gln Ala Ala Phe Tyr Glu Ile Leu His Leu Pro Asn Leu Thr Glu
65                  70                  75                  80

Lys Gln Arg Asn His Phe Ile Gln Ile Leu Arg Asp Asp Pro Ser Val
                85                  90                  95

Ser Leu Arg Val Leu Gly Tyr Ala Gln His Leu Asn Asp Ser Gln Ala
            100                 105                 110

Pro Lys


<210> SEQ ID NO 62
<211> LENGTH: 114
<212> TYPE: PRT
<213> ORGANISM: Artificial Sequence
<220> FEATURE:
<223> OTHER INFORMATION: Artificially synthesized spike protein binding
      protein 213099 (LQRETY-group)

<400> SEQUENCE: 62

Ala Lys Phe Asp Glu Ala Gln Leu Ala Ala Phe Gln Glu Ile Arg His
1               5                   10                  15

Leu Pro Asn Leu Thr Glu Glu Gln Arg Glu Ala Phe Ile Thr Ser Leu
            20                  25                  30

Tyr Asp Asp Pro Ser Val Ser Leu Glu Val Leu Gly Glu Ala Gln Lys
        35                  40                  45

Leu Asn Asp Ser Gln Ala Pro Lys Ile Ala Ala Lys Phe Asp Glu Ala
    50                  55                  60

Gln Gln Ala Ala Phe Tyr Glu Ile Leu His Leu Pro Asn Leu Thr Glu
65                  70                  75                  80

His Gln Arg Asn Ala Phe Ile Gln Trp Leu Arg Asp Asp Pro Ser Val
                85                  90                  95

Ser Leu Gln Val Leu Gly His Ala Gln Gln Leu Asn Asp Ser Gln Ala
            100                 105                 110

Pro Lys


<210> SEQ ID NO 63
<211> LENGTH: 114
<212> TYPE: PRT
<213> ORGANISM: Artificial Sequence
<220> FEATURE:
<223> OTHER INFORMATION: Artificially synthesized Spike protein binding
      protein SEQ28 dimer

<400> SEQUENCE: 63

Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Val Leu Asp Ile Asp
```

```
    50                  55                  60

Gln His Ala Ala Thr Glu Glu Ile Trp Trp Leu Pro Asn Leu Thr Lys
65                  70                  75                  80

Gln Gln Lys Val Trp Phe Ile Met Ser Leu Thr Gln Asp Pro Ser Val
                85                  90                  95

Ser Leu Glu Ile Leu Ala Glu Ala Lys Lys Leu Asn Asp Ala Gln Ala
            100                 105                 110

Pro Lys


<210> SEQ ID NO 64
<211> LENGTH: 114
<212> TYPE: PRT
<213> ORGANISM: Artificial Sequence
<220> FEATURE:
<223> OTHER INFORMATION: Artificially synthesized spike protein binding
      protein SEQ ID NO: 1dimer

<400> SEQUENCE: 64

Ala Val Leu Asp Ile Ala Gln His Ser Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Lys Glu Val Leu Gly Glu Ala Gln Lys
        35                  40                  45

Leu Asn Asp Ser Gln Ala Pro Lys Asn Ala Ala Val Leu Asp Ile Ala
    50                  55                  60

Gln His Ser Ala Thr Glu Glu Ile Trp Trp Leu Pro Asn Leu Thr Lys
65                  70                  75                  80

Gln Gln Lys Val Trp Phe Ile Met Ser Leu Thr Gln Asp Pro Ser Val
                85                  90                  95

Ser Lys Glu Val Leu Gly Glu Ala Gln Lys Leu Asn Asp Ser Gln Ala
            100                 105                 110

Pro Lys


<210> SEQ ID NO 65
<211> LENGTH: 58
<212> TYPE: PRT
<213> ORGANISM: Artificial Sequence
<220> FEATURE:
<223> OTHER INFORMATION: Artificially synthesized spike protein binding
      protein 434 consensus
<220> FEATURE:
<221> NAME/KEY: Xaa
<222> LOCATION: (8)..(8)
<223> OTHER INFORMATION: Xaa may be selected from A or D
<220> FEATURE:
<221> NAME/KEY: Xaa
<222> LOCATION: (11)..(11)
<223> OTHER INFORMATION: Xaa may be selected from S or A
<220> FEATURE:
<221> NAME/KEY: Xaa
<222> LOCATION: (42)..(42)
<223> OTHER INFORMATION: Xaa may be selected from K or L
<220> FEATURE:
<221> NAME/KEY: Xaa
<222> LOCATION: (44)..(44)
<223> OTHER INFORMATION: Xaa may be selected from V or I
<220> FEATURE:
<221> NAME/KEY: Xaa
<222> LOCATION: (46)..(46)
<223> OTHER INFORMATION: Xaa may be selected from G or A
<220> FEATURE:
<221> NAME/KEY: Xaa
<222> LOCATION: (49)..(49)
<223> OTHER INFORMATION: Xaa may be selected from Q or K
```

```
<220> FEATURE:
<221> NAME/KEY: Xaa
<222> LOCATION: (54)..(54)
<223> OTHER INFORMATION: Xaa may be selected from S or A

<400> SEQUENCE: 65

Asn Ala Ala Val Leu Asp Ile Xaa Gln His Xaa Ala Thr Glu Glu Ile
1               5                   10                  15

Trp Trp Leu Pro Asn Leu Thr Lys Gln Gln Lys Val Trp Phe Ile Met
            20                  25                  30

Ser Leu Thr Gln Asp Pro Ser Val Ser Xaa Glu Xaa Leu Xaa Glu Ala
        35                  40                  45

Xaa Lys Leu Asn Asp Xaa Gln Ala Pro Lys
    50                  55


<210> SEQ ID NO 66
<211> LENGTH: 114
<212> TYPE: PRT
<213> ORGANISM: Artificial Sequence
<220> FEATURE:
<223> OTHER INFORMATION: Artificially synthesized Spike protein binding
      protein dimer 212361del2N

<400> SEQUENCE: 66

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Val Leu Gly Glu Ala Arg Lys
        35                  40                  45

Leu Asn Thr Ser Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Val Leu Gly Glu Ala Gln Lys Leu Asn Asp Ser Gln Ala
            100                 105                 110

Pro Lys


<210> SEQ ID NO 67
<211> LENGTH: 114
<212> TYPE: PRT
<213> ORGANISM: Artificial Sequence
<220> FEATURE:
<223> OTHER INFORMATION: Artificially synthesized spike protein binding
      protein dimer 212335del2N

<400> SEQUENCE: 67

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Val Leu Gly Glu Ala Arg Lys
        35                  40                  45

Leu Asn Thr Ser Gln Ala Pro Lys Ile Ala Ala Lys Phe Asp Glu Ala
    50                  55                  60

Gln Tyr Ala Ala Phe Leu Glu Ile His His Leu Pro Asn Leu Thr Glu
65                  70                  75                  80
```

```
Glu Gln Arg His Ala Phe Ile Leu Ser Leu Tyr Asp Asp Pro Ser Val
                85                  90                  95

Ser Leu Glu Val Leu Gly Glu Ala Gln Lys Leu Asn Asp Ser Gln Ala
            100                 105                 110

Pro Lys


<210> SEQ ID NO 68
<211> LENGTH: 347
<212> TYPE: PRT
<213> ORGANISM: Artificial Sequence
<220> FEATURE:
<223> OTHER INFORMATION: Artificially synthesized fusion protein of
      SEQ43 x (PAdelFc)3 x SEQ28

<400> SEQUENCE: 68

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Ile Ala Ala Gln His Asp Lys Ile Gln Gln
225                 230                 235                 240

Ala Ala Asp Lys Glu Ile Leu His Leu Pro Asn Leu Thr Glu Glu Gln
                245                 250                 255

Arg Asn Lys Phe Arg Gln Ser Leu Arg Asp Asp Pro Ser Val Ser Ala
            260                 265                 270

Glu Ile Leu Ala Glu Ala Lys Lys Leu Asn Asp Ala Gln Ala Pro Lys
        275                 280                 285

Ile Ala Ala Val Leu Asp Ile Asp Gln His Ala Ala Thr Glu Glu Ile
    290                 295                 300

Trp Trp Leu Pro Asn Leu Thr Lys Gln Gln Lys Val Trp Phe Ile Met
305                 310                 315                 320
```

```
Ser Leu Thr Gln Asp Pro Ser Val Ser Leu Glu Ile Leu Ala Glu Ala
                325                 330                 335

Lys Lys Leu Asn Asp Ala Gln Ala Pro Lys Cys
            340                 345


<210> SEQ ID NO 69
<211> LENGTH: 289
<212> TYPE: PRT
<213> ORGANISM: Artificial Sequence
<220> FEATURE:
<223> OTHER INFORMATION: Artificially synthesized fusion protein of
      SEQ43 x (PAdelFc)2 x SEQ28

<400> SEQUENCE: 69

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Ile Ala Ala Val Leu Asp Ile Asp Gln His
225                 230                 235                 240

Ala Ala Thr Glu Glu Ile Trp Trp Leu Pro Asn Leu Thr Lys Gln Gln
                245                 250                 255

Lys Val Trp Phe Ile Met Ser Leu Thr Gln Asp Pro Ser Val Ser Leu
            260                 265                 270

Glu Ile Leu Ala Glu Ala Lys Lys Leu Asn Asp Ala Gln Ala Pro Lys
        275                 280                 285

Cys


<210> SEQ ID NO 70
<211> LENGTH: 231
<212> TYPE: PRT
<213> ORGANISM: Artificial Sequence
<220> FEATURE:
```

<223> OTHER INFORMATION: Artificially synthesized fusion protein of SEQ43 x (PAdelFc)1 x SEQ28

<400> SEQUENCE: 70

```
Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Gln His Asp Lys Ile Gln Gln Ala Ala Asp Lys
        115                 120                 125

Glu Ile Leu His Leu Pro Asn Leu Thr Glu Glu Gln Arg Asn Lys Phe
    130                 135                 140

Arg Gln Ser Leu Arg Asp Asp Pro Ser Val Ser Ala Glu Ile Leu Ala
145                 150                 155                 160

Glu Ala Lys Lys Leu Asn Asp Ala Gln Ala Pro Lys Ile Ala Ala Val
                165                 170                 175

Leu Asp Ile Asp Gln His Ala Ala Thr Glu Glu Ile Trp Trp Leu Pro
            180                 185                 190

Asn Leu Thr Lys Gln Gln Lys Val Trp Phe Ile Met Ser Leu Thr Gln
        195                 200                 205

Asp Pro Ser Val Ser Leu Glu Ile Leu Ala Glu Ala Lys Lys Leu Asn
    210                 215                 220

Asp Ala Gln Ala Pro Lys Cys
225                 230
```

<210> SEQ ID NO 71
<211> LENGTH: 289
<212> TYPE: PRT
<213> ORGANISM: Artificial Sequence
<220> FEATURE:
<223> OTHER INFORMATION: Artificially synthesized fusion protein of SEQ28 x SEQ43 x (PAdelFc)2

<400> SEQUENCE: 71

```
Ala Val Leu Asp Ile Asp Gln His Ala Ala Thr Glu Glu Ile Trp Trp
1               5                   10                  15

Leu Pro Asn Leu Thr Lys Gln Gln Lys Val Trp Phe Ile Met Ser Leu
            20                  25                  30

Thr Gln Asp Pro Ser Val Ser Leu Glu Ile Leu Ala Glu Ala Lys Lys
        35                  40                  45

Leu Asn Asp Ala Gln Ala Pro Lys Ile Ala Ala Lys Phe Asp Glu Ala
    50                  55                  60

Gln Gln Tyr Ala Phe Tyr Lys Ile Leu His Leu Trp Asn Leu Thr Glu
65                  70                  75                  80

Glu Gln Arg Asn Ala Phe Ile Gln Ser Leu Arg Asp Asp Pro Ser Val
                85                  90                  95
```

```
Ser Leu Glu Ile Leu Ala Glu Ala Arg Lys Leu Asn Thr Ala Gln Ala
            100                 105                 110

Pro Lys Ile Ala Ala Lys Phe Asp Glu Ala Gln Tyr Ala Ala Phe Leu
        115                 120                 125

Glu Ile Val His Leu Pro Asn Leu Thr Glu Glu Gln Arg Gln Ala Phe
    130                 135                 140

Ile Ala Ser Leu Trp Asp Asp Pro Ser Val Ser Leu Glu Ile Leu Ala
145                 150                 155                 160

Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Ile Ala Ala Gln His Asp Lys Ile Gln Gln
225                 230                 235                 240

Ala Ala Asp Lys Glu Ile Leu His Leu Pro Asn Leu Thr Glu Glu Gln
                245                 250                 255

Arg Asn Lys Phe Arg Gln Ser Leu Arg Asp Asp Pro Ser Val Ser Ala
            260                 265                 270

Glu Ile Leu Ala Glu Ala Lys Lys Leu Asn Asp Ala Gln Ala Pro Lys
        275                 280                 285

Cys


<210> SEQ ID NO 72
<211> LENGTH: 289
<212> TYPE: PRT
<213> ORGANISM: Artificial Sequence
<220> FEATURE:
<223> OTHER INFORMATION: Artificially synthesized fusion protein of
      SEQ43 x SEQ28 x (PAdelFc)2

<400> SEQUENCE: 72

Ala Lys Phe Asp Glu Ala Gln Gln Tyr Ala Phe Tyr Lys Ile Leu His
1               5                   10                  15

Leu Trp Asn Leu Thr Glu Glu Gln Arg Asn Ala Phe Ile Gln Ser Leu
            20                  25                  30

Arg Asp Asp Pro Ser Val Ser Leu Glu Ile Leu Ala Glu Ala Arg Lys
        35                  40                  45

Leu Asn Thr Ala Gln Ala Pro Lys Ile Ala Ala Lys Phe Asp Glu Ala
    50                  55                  60

Gln Tyr Ala Ala Phe Leu Glu Ile Val His Leu Pro Asn Leu Thr Glu
65                  70                  75                  80

Glu Gln Arg Gln Ala Phe Ile Ala Ser Leu Trp Asp Asp Pro Ser Val
                85                  90                  95

Ser Leu Glu Ile Leu Ala Glu Ala Lys Lys Leu Asn Asp Ala Gln Ala
            100                 105                 110

Pro Lys Ile Ala Ala Val Leu Asp Ile Asp Gln His Ala Ala Thr Glu
        115                 120                 125

Glu Ile Trp Trp Leu Pro Asn Leu Thr Lys Gln Gln Lys Val Trp Phe
    130                 135                 140

Ile Met Ser Leu Thr Gln Asp Pro Ser Val Ser Leu Glu Ile Leu Ala
145                 150                 155                 160
```

-continued

```
Glu Ala Lys Lys Leu Asn Asp Ala Gln Ala Pro Lys Ile Ala Ala Gln
                165                 170                 175

His Asp Lys Ile Gln Gln Ala Ala Asp Lys Glu Ile Leu His Leu Pro
            180                 185                 190

Asn Leu Thr Glu Glu Gln Arg Asn Lys Phe Arg Gln Ser Leu Arg Asp
        195                 200                 205

Asp Pro Ser Val Ser Ala Glu Ile Leu Ala Glu Ala Lys Lys Leu Asn
    210                 215                 220

Asp Ala Gln Ala Pro Lys Ile Ala Ala Gln His Asp Lys Ile Gln Gln
225                 230                 235                 240

Ala Ala Asp Lys Glu Ile Leu His Leu Pro Asn Leu Thr Glu Glu Gln
                245                 250                 255

Arg Asn Lys Phe Arg Gln Ser Leu Arg Asp Asp Pro Ser Val Ser Ala
            260                 265                 270

Glu Ile Leu Ala Glu Ala Lys Lys Leu Asn Asp Ala Gln Ala Pro Lys
        275                 280                 285

Cys
```